(12) United States Patent
Aubry et al.

(10) Patent No.: US 10,087,165 B2
(45) Date of Patent: Oct. 2, 2018

(54) FLUOROQUINOLONES AND USE THEREOF TO TREAT BACTERIAL INFECTIONS

(71) Applicant: UNIVERSITÉ PIERRE ET MARIE CURIE—PARIS 6 (UPMC), Paris (FR)

(72) Inventors: Alexandra Aubry, Massy (FR); Guillaume Anquetin, Massy (FR)

(73) Assignee: Sorbonne Universite, Paris (FR)

( * ) Notice: Subject to any disclaimer, the term of this patent is extended or adjusted under 35 U.S.C. 154(b) by 0 days.

(21) Appl. No.: 15/319,620

(22) PCT Filed: Jun. 18, 2015

(86) PCT No.: PCT/EP2015/063752
§ 371 (c)(1),
(2) Date: Dec. 16, 2016

(87) PCT Pub. No.: WO2015/193454
PCT Pub. Date: Dec. 23, 2015

(65) Prior Publication Data
US 2017/0144992 A1 May 25, 2017

(30) Foreign Application Priority Data
Jun. 18, 2014 (EP) .................................... 14173040

(51) Int. Cl.
*C07D 401/10* (2006.01)
*A61K 31/496* (2006.01)

(52) U.S. Cl.
CPC .......... *C07D 401/10* (2013.01); *A61K 31/496* (2013.01)

(58) Field of Classification Search
CPC ............................ A61K 31/496; C07D 401/10
See application file for complete search history.

(56) References Cited

U.S. PATENT DOCUMENTS

| | | |
|---|---|---|
| 4,670,444 A | 6/1987 | Grohe et al. |
| 4,980,470 A | 12/1990 | Masuzawa et al. |
| 5,607,942 A | 3/1997 | Peterson et al. |

FOREIGN PATENT DOCUMENTS

| | | |
|---|---|---|
| EP | 0049355 A1 | 4/1982 |
| EP | 0113092 A1 | 7/1984 |
| EP | 0117473 A1 | 9/1984 |

OTHER PUBLICATIONS

Wolff, Manfred E., Burger's Medicinal Chemistry and Drug Discovery, Fifth Ed., vol. 1: Principles and Practice, John Wiley & Sons, 1995, 975.*
Banker, Gilbert S. et al., Modem Pharmaceutics, Marcel Dekker, New York, 1996.*
West, Anthony R., Solid State Chemistry and Its Applications, Wiley, New York, 1988, 358.*
Naz, et al., CoMFA and CoMSIA studies on a series of fluroquinolone derivatives for potential anti-inflammatory activity, Analytical Methods, 6(17), 6823-6831 (Jun. 9, 2014).*
Cormier, et al., Studies on the antimicrobial properties of N-acylated Ciprofloxacins, Bioorganic & Medicinal Chemistry Letters, 22(20), 6513-6520 (2012).*
Patent Cooperation Treaty, International Search Report for PCT/EP2015/063752, dated Jul. 22, 2015, 5 pages.
Patent Cooperation Treaty, Written Opinion of the International Searching Authority for PCT/EP2015/063752, dated Jul. 22, 2015, 5 pages.
Aubry et al., "*Mycobacterium tuberculois* DNA Gyrase: Integration with Quinolones and Correlation with Antimycobacterial Drug Activity," Apr. 2004, pp. 1281-1288, Antimicrobial Agents and Chemotherapy, vol. 48, No. 4.
Azema et al., "Synthesis of lipophilic dimeric C-7/C-7-linked ciprofloxacin and C-6/C-6-linked levofloxacin derivatives. Versatile in vitro biological evaluations of monomeric and dimeric fluoroquinolone derivatives as potential antitumor, antibacterial or antimycobacterial agents," 2011, pp. 6025-6038 European Journal of Medicinal Chemistry, vol. 46.
Bermejo et al., "Validation of a Biophysical Drug Absorption Model by the PATQSAR System," 1999, pp. 398-405, Journal of Pharmaceutical Sciences, vol. 88, No. 4.
Guillemin et al., "Correlation between Quinolone Susceptibility Patterns and Sequences in the A and B Subunits of DNA Gyrase in Mycobacteria," 1998, pp. 2084-2088, Antimicrobial Agents and Chemotherapy, vol. 42, No. 8.
Magiorakos et al., "Mutildrug-resistant, extensively drug-resistant and pandrug-resistant bacteria: an international expert proposal for interim standard definitions for acquired resistance," published May 2011, pp. 268-281, Clinical Microbiology and Infection, vol. 18.
Maruri et al, "A systematic review of gyrase mutations associated with fluoroquinolone-resistant *Mycrobacterium tuberculosis* and a proposed gyrase numbering system," 2012, pp. 819-831, Journal of Antimicrobial Chemotherapy, vol. 67.
Poissy et al., "Should Moxifloxacin be used for the Treatment of Extensively Drug-Resistant Tuberculois? An Answwer from a Murine Model," 2010, pp. 4765-4771, Antimicrobial Agents and Chemotherapy, vol. 54, No. 11.
Azema et al., "7-((4-Substituted) piperazin-1yl) derivatives of ciprofloxacin: Synthesis and in vitro biological evaluation as potential antitumor agents," 2009, pp. 5396-5407, Bioorganic & Medicinal Chemistry, vol. 17.
Christophe et al., "High Content Screening Identifies Decapreynl-Phosphoribose 2' Epimerase as a Target for Intracellular Antimycobacterial Inhibitors," 2009, p. E1000645, Plos Pahogens, vol. 5 No. 10.

(Continued)

Primary Examiner — Erich A Leeser
(74) Attorney, Agent, or Firm — Heslin Rothenberg Farley & Mesiti P.C.

(57) ABSTRACT

The present invention relates to novel fluoroquinolones, pharmaceutical compositions or medicament containing them and use thereof to treat bacterial infection.

12 Claims, 2 Drawing Sheets

(56) References Cited

OTHER PUBLICATIONS

Haemers et al., "Influence of N Substitution on Antimycobacterial Activity of Ciprofloxin," 1990, pp. 496-497, Antimicrobial Agents and Chemotherapy, vol. 34, No. 3.

* cited by examiner

FLUOROQUINOLONES AND USE THEREOF TO TREAT BACTERIAL INFECTIONS

CROSS REFERENCE TO RELATED APPLICATIONS

This application is a national stage filing under section 371 of International Application No. PCT/EP2015/063752, filed on Jun. 18, 2015, published in English on Dec. 23, 2015, as WO2015/193454A1 and which claims priority to European Application No. 14173040.8, filed on Jun. 18, 2014, the entire disclosure of these applications being hereby incorporated herein by reference.

FIELD OF INVENTION

The present invention relates to compounds of the class of fluoroquinolone possessing a piperazine moiety substituted by a long alkyl chain including their pharmaceutically acceptable salts, solvates or prodrugs. The compounds of the invention are useful in the treatment of an infection caused by bacteria.

BACKGROUND OF INVENTION

Bacterial infections are responsible for diseases or syndromes such as urinary tract infection, skin and soft tissue infection, sexually transmitted infection, tetanus, typhoid, tuberculosis, cholera, syphilis, pneumonia or *salmonella*. Despite the high number and the diversity of antibacterial agents, bacterial infections are a main cause of death worldwide, especially in developing countries. Moreover, the continuous appearance of drug-resistant bacteria is worrying both in developed and developing countries.

The over-prescription of antibiotics seems to be one of the main reasons of the appearance of resistances. However, other factors such as the use of antibiotics in animal husbandry and the increasing number of antibacterial agents in cleaning products are also responsible for the appearance of resistance. Moreover, even without exposure to antibiotics, DNA mutations and acquisition of extra chromosomic DNA naturally occur in bacteria potentially leading to resistance.

Depending on their degree of resistance, drug-resistant bacteria are classified in three groups: multidrug-resistant (MDR), extensively drug-resistant (XDR) and pandrug-resistant (PDR) (Magiorakos, A.-P. et al, *Clinical Microbiology and Infection*, 2012, pp. 268-281). There is thus a need to develop antibiotics active against wild type of bacteria but also against the different classes of drug-resistant bacteria. Moreover, any bacteria that survive exposure to an antibiotic will replicate and produce resistance offspring and antibiotics have thus to possess a maximal capability of bacterial eradication.

Quinolones form a large class of antibiotics developed in the 60s possessing activities against a broad scope of bacteria. The addition of a fluorine atom on the aromatic ring led to the discovery, in the 70s, of fluoroquinolones. These molecules possess improved pharmacokinetic properties compared to quinolones such as good oral absorption, good tissue penetration and relatively long duration of activity. Fluoroquinolones such as ciprofloxacin (U.S. Pat. No. 4,670,444, EP0049355), enrofloxacin (U.S. Pat. No. 4,670,444, EP0049355), gatifloxacin (U.S. Pat. No. 4,980,470) and moxifloxacin (U.S. Pat. No. 5,607,942) are currently used to treat various types of bacterial infections that is as initial treatment or second-line therapy.

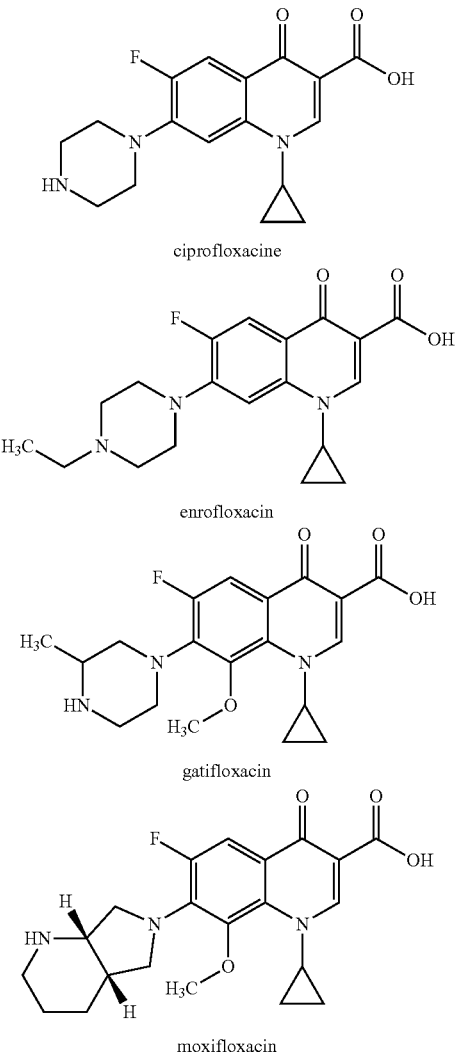

ciprofloxacine enrofloxacin gatifloxacin moxifloxacin

The mechanism of action of fluoroquinolone in bacteria consists in inhibiting the bacterial enzyme DNA gyrase necessary for DNA replication and resistance to fluoroquinolone mainly comes from mutation on DNA gyrase.

Therefore, even if fluoroquinolones allow to treat a large scope of bacterial infections and possess good pharmacokinetics properties, these molecules suffer from the appearance of high resistance.

There is thus a need to develop new compounds active against wild-type of bacteria but also against drug-resistant bacteria that is MDR, XDR or PDR. Such compounds have to be capable of overcoming the resistance mechanisms developed by bacteria against currently used antibiotics and have to possess a maximal capability of bacterial eradication while exhibiting a low toxicity.

The present invention relates to compounds of the class of fluoroquinolones possessing a piperazine moiety substituted by a long alkyl chain. The compounds of the invention possess an improved bactericidal activity compared to currently used fluoroquinolones against wild-type bacteria but also against drug-resistant bacteria.

SUMMARY

According to a one embodiment, the compounds of the invention have the general Formula I:

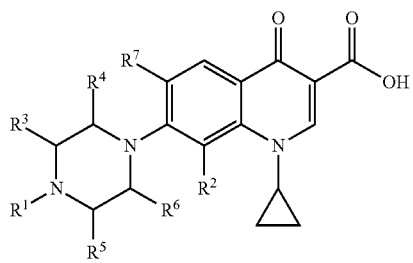

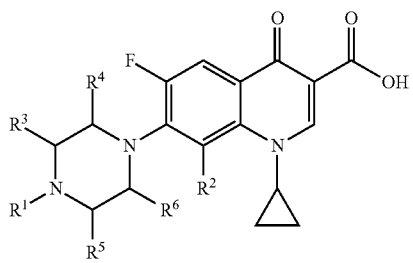

and pharmaceutically acceptable salts, solvates and prodrugs thereof, wherein:

R¹ represents a saturated or unsaturated, substituted or unsubstituted, branched or unbranched alkyl group comprising 4 to 20 carbons atoms, preferably 5 to 16, more preferably 5, 6, 7, 8, 9, 10, 11, 12, 13, 14, 15 or 16 carbons, when the alkyl group is substituted, the substituent is selected in the group comprising halo, hydroxyl, oxo, nitro, amido, carboxy, amino, cyano, alkoxy, haloalkoxy, or haloalkyl, R² represents a substituent selected from the group comprising hydrogen, alkyl, alkene, alkyne, cycloalkyl, aryl, halo, hydroxyl, oxo, nitro, amido, carboxy, amino, cyano, alkoxy, haloalkoxy, or haloalkyl, preferably R² represents a substituent selected from the group comprising hydrogen, methyl, methoxy, ethoxy, chloro, fluoro, more preferably R² is hydrogen or methoxy, even more preferably R² is a methoxy group, R³, R⁴, R⁵ and R⁶ may be identical or different and each represents a substituent selected from hydrogen, alkyl, alkene, alkyne, cycloalkyl, aryl, halo, hydroxyl, oxo, nitro, amido, carboxy, amino, cyano, alkoxy, haloalkoxy, or haloalkyl, preferably R³, R⁴, R⁵ and R⁶ are identical and represent each a hydrogen, R⁷ represents a substituent selected from hydrogen, alkyl, alkene, alkyne, cycloalkyl, aryl, halo, hydroxyl, oxo, nitro, amido, carboxy, amino, cyano, alkoxy, haloalkoxy, or haloalkyl, preferably R⁷ represents a hydrogen, —NH₂ or fluoro, with the condition that the compounds of formula I are not:

7-(4-butylpiperazin-1-yl)-1-cyclopropyl-6-fluoro-4-oxo-1,4-dihydroquinoline-3-carboxylic acid,
1-cyclopropyl-6-fluoro-7-(4-heptylpiperazin-1-yl)-4-oxo-1,4-dihydroquinoline-3-carboxylic acid,
7-(4-butyl-3-methylpiperazin-1-yl)-1-cyclopropyl-6-fluoro-4-oxo-1,4-dihydroquinoline-3-carboxylic acid,
1-cyclopropyl-6-fluoro-7-(4-hexyl-3-methylpiperazin-1-yl)-4-oxo-1,4-dihydroquinoline-3-carboxylic acid,
1-cyclopropyl-6-fluoro-7-(4-(4-hydroxybutyl)piperazin-1-yl)-4-oxo-1,4-dihydroquinoline-3-carboxylic acid, with the condition that when R² is a hydrogen and R⁷ is a fluorine, R³, R⁴, R⁵ and R⁶ are not a methyl group.

According to another embodiment, the compounds of the invention have the general formula II corresponding to the general formula I wherein R⁷ is a fluorine:

and pharmaceutically acceptable salts, solvates and prodrugs thereof.

According to another embodiment, the compounds of the invention have the general formula III corresponding to compounds of general formula II wherein R³, R⁴, R⁵ and R⁶ are identical and represent a hydrogen atom:

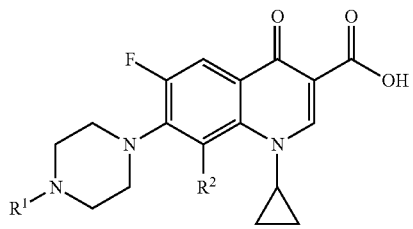

and pharmaceutically acceptable salts, solvates and prodrugs thereof.

In a preferred embodiment, the compounds of the invention are selected in a group comprising 1-cyclopropyl-6-fluoro-4-oxo-7-(4-pentylpiperazin-1-yl)-1,4-dihydroquinoline-3-carboxylic acid, 1-cyclopropyl-6-fluoro-7-(4-hexylpiperazin-1-yl)-4-oxo-1,4-dihydroquinoline-3-carboxylic acid, 1-cyclopropyl-6-fluoro-7-(4-octylpiperazin-1-yl)-4-oxo-1,4-dihydroquinoline-3-carboxylic acid, 1-cyclopropyl-6-fluoro-7-(4-nonylpiperazin-1-yl)-4-oxo-1,4-dihydroquinoline-3-carboxylic acid, 1-cyclopropyl-7-(4-decylpiperazin-1-yl)-6-fluoro-4-oxo-1,4-dihydroquinoline-3-carboxylic acid, 1-cyclopropyl-6-fluoro-4-oxo-7-(4-undecylpiperazin-1-yl)-1,4-dihydroquinoline-3-carboxylic acid, 1-cyclopropyl-7-(4-dodecylpiperazin-1-yl)-6-fluoro-4-oxo-1,4-dihydroquinoline-3-carboxylic acid, 1-cyclopropyl-6-fluoro-4-oxo-7-(4-tridecylpiperazin-1-yl)-1,4-dihydroquinoline-3-carboxylic acid, 1-cyclopropyl-6-fluoro-4-oxo-7-(4-tetradecylpiperazin-1-yl)-1,4-dihydroquinoline-3-carboxylic acid, 1-cyclopropyl-6-fluoro-4-oxo-7-(4-pentadecylpiperazin-1-yl)-1,4-dihydroquinoline-3-carboxylic acid, 1-cyclopropyl-6-fluoro-7-(4-hexadecylpiperazin-1-yl)-4-oxo-1,4-dihydroquinoline-3-carboxylic acid, 1-cyclopropyl-6-fluoro-8-methoxy-4-oxo-7-(4-pentylpiperazin-1-yl)-1,4-dihydroquinoline-3-carboxylic acid, 1-cyclopropyl-6-fluoro-7-(4-hexylpiperazin-1-yl)-8-methoxy-4-oxo-1,4-dihydroquinoline-3-carboxylic acid, 1-cyclopropyl-6-fluoro-7-(4-heptylpiperazin-1-yl)-8-methoxy-4-oxo-1,4-dihydroquinoline-3-carboxylic acid, 1-cyclopropyl-6-fluoro-8-methoxy-7-(4-octylpiperazin-1-yl)-4-oxo-1,4-dihydroquinoline-3-carboxylic acid, 1-cyclopropyl-6-fluoro-8-methoxy-7-(4-nonylpiperazin-1-yl)-4-oxo-1,4-dihydroquinoline-3-carboxylic acid, 1-cyclopropyl-7-(4-decylpiperazin-1-yl)-6-fluoro-8-methoxy-4-oxo-1,4-dihydroquinoline-3-carboxylic acid, 1-cyclopropyl-6- fluoro-8-methoxy-4-oxo-7-(4-undecylpiperazin-1-yl)-1,4-dihydroquinoline-3-carboxylic acid, 1-cyclopropyl-7-(4-dodecylpiperazin-1-yl)-6-fluoro-8-methoxy-4-oxo-1,4-dihydroquinoline-3-carboxylic acid, 1-cyclopropyl-6-fluoro-8-methoxy-4-oxo-7-(4-tridecylpiperazin-1-yl)-1,4-dihydroquinoline-3-carboxylic acid, 1-cyclopropyl-6-fluoro-8-methoxy-4-oxo-7-(4-tetradecylpiperazin-1-yl)-1,4-dihydroquinoline-3-carboxylic acid, 1-cyclopropyl-6-fluoro-8-methoxy-4-oxo-7-(4-pentadecylpiperazin-1-yl)-1,4-dihydroquinoline-3-carboxylic acid, 1-cyclopropyl-6-fluoro-7-(4-hexadecylpiperazin-1-yl)-8-methoxy-4-oxo-1,4-dihydroquinoline-3-carboxylic acid, and pharmaceutically acceptable salts, solvates and prodrugs thereof.

According to another embodiment, the present invention relates to a pharmaceutical composition comprising at least one compound of the invention, or a pharmaceutically acceptable salt, solvate or prodrug thereof, and at least one pharmaceutically acceptable carrier, diluent, excipient and/or adjuvant.

According to one embodiment, the present invention also concerns a medicament comprising at least one compound of the invention, or a pharmaceutically acceptable solvate thereof.

According to one embodiment, the pharmaceutically acceptable carrier, diluent, excipient and/or adjuvant is selected from Ethanol 5%, Glycerin 15%, Polyethylene glycol 300 50%, Polyethylene glycol 400 9%, Polysorbate 80 0.4%, Propylene glycol 68%, 2-hydroxypropyl-cyclodextrin 20%, Methyl cellulose 0.5% and corn oil. In one embodiment, the pharmaceutically acceptable carrier, diluent, excipient and/or adjuvant is selected from Polysorbate 80 0.4% or corn oil.

According to another embodiment, the pharmaceutical composition or medicament of the invention, further comprises a therapeutic agent and/or active ingredient.

According to one embodiment, the compound, the pharmaceutical composition or the medicament of the invention are useful in the treatment of a bacterial infection.

According to another embodiment, the compound, pharmaceutical composition or medicament of the invention are useful in the treatment of a bacterial infection, wherein the bacterial infection is caused by a bacteria of the genus selected in the group comprising *Mycobacterium* such as tuberculosis or *leprae*; Gram positive bacteria such as *Streptococcus, Staphylococcus* or *Bacillus*; enterobacteriaceae such as *Escherichia, Klebsiella, Enterobacter, Proteus, Serratia, Shigella, Citrobacter, Salmonella* or *Yersinia*, non-fermenting Gram negative bacilli such as *Pseudomonas, Alcaligenes*, or *Acitenobacter*; anaerobes such as *Bacteroides, Fusobacterium, Eubacterium, Propionibacterium, Peptococcus, Clostridium, Peptostreptococcus*, or *Veillonella; Helicobacter pylori* and pathogens involved in sexually transmitted infections such as *Neisseria, Haemophilus, Chlamydia*, or *Mycoplasma*.

DEFINITIONS

In the present invention, the following terms have the following meanings:

"aryl" refers to a polyunsaturated, aromatic hydrocarbyl group having a single ring (i.e. phenyl) or multiple aromatic rings fused together (e.g. naphtyl) or linked covalently, typically containing 5 to 12 atoms; preferably 6 to 10, wherein at least one ring is aromatic.

"aliphatic group" applies to any carbonated, acyclic or cyclic, saturated or unsaturated, branched or unbranched group, optionally substituted, excluding aromatic compounds. According to the invention, an aliphatic group preferably comprises 4 to 20 carbon atoms, preferably 5 to 16 carbon atoms, more preferably 5, 6, 7, 8, 9, 10, 11, 12, 13, 14, 15 or 16 carbons. According to one preferred embodiment of the invention, branched or unbranched aliphatic groups are selected from alkyl, alkenyl, alkynyl groups.

"alkyl" applies to any saturated linear or branched hydrocarbon chain, optionally substituted, comprising 4 to 20 carbon atoms, and preferably 5 to 16 carbon atoms; more preferably butyl, pentyl, hexyl, heptyl, octyl, nonyl, decyl, undecyl, dodecyl, tridecyl, tetradecyl, pentadecyl, hexadecyl.

"cycloalkyl" applies to a cyclic or polycyclic, optionally branched, substituted or unsubstituted alkyl group; preferably a cyclopropyl, cyclopentyl or cyclohexyl group.

"carboxy" refers to a —COOH group.

"alkenyl" applies to any linear or branched, optionally substituted hydrocarbon chain, carrying at least one double bond.

"alkynyl" applies to any linear or branched, optionally substituted hydrocarbon chain carrying at least one triple bond.

"alkoxy" applies to an O-alkyl group. One preferred alkoxy group for this invention is the methoxy group.

"aromatic group" applies to a mono- or polycyclic system with 6 to 12, carbon atoms possessing one or several aromatic rings (when there are two rings, the term used is a biaryl) among which are included the phenyl group, the biphenyl group, the 1-naphthyl group, the 2-naphthyl group, the anthracenyl group, the pyrenyl group, the tetrahydronaphthyl group, the indanyl group and the binaphthyl group. The term aromatic group also applies to any aromatic ring comprising at least one heteroatom selected from an oxygen, nitrogen or sulphur atom, among which are included quinoline, terpyridinyl, bipyridinyl, guanine, phenantroline, hydroxyquinoline. The aromatic group may be substituted by 1 to 3 substituents selected independently of each other from a group comprising a hydroxyl group, a linear or branched alkyl group comprising 1, 2, 3, 4, 5 or 6 carbon atoms, particularly methyl, ethyl, propyl, butyl, an alkoxy group or a halogen atom, particularly bromine, chlorine and iodine. When the aromatic group is substituted, it may be meta and/or para and/or ortho substituted.

"halo" refers to a fluoro, chloro, bromo, or iodo. One preferred halo group for this invention is the fluoro group.

"hydroxyl" refers to —OH.

"oxo" refers to a —C═O function.

"nitro" refers to —NO$_2$.

"cyano" refers to —CN.

"amino" refers to a —NH$_2$ group or any group derived from —NH$_2$ by substitution of one or several hydrogen atoms by an aliphatic or aromatic, substituted or unsubstituted organic group, wherein when the aliphatic or aromatic group is substituted, it is by one or several substituents, selected from the group comprising halo, hydroxyl, oxo, nitro, amido, carboxy, amino, cyano, haloalkoxy, haloalkyl. —NH$_2$ derivative groups are preferably alkylamino groups, in other words N-alkyl groups including the monoalkylamino and dialkylamino groups.

"amido" refers to a —NR—CO— function wherein R is H or alkyl.

"drug-resistant" refers to a bacteria strain resistant to at least one drug, said bacteria being multidrug-resistant, extensively drug-resistant or pandrug-resistant.

"multidrug-resistant" refers to a bacteria strain resistant to more than one antimicrobial agent, preferably resistant to at least one agent in three or more antimicrobial category.

"extensively drug-resistant" is equivalent to extremely drug resistant and refers to a bacteria strain resistant to at least one agent in all but two or fewer antimicrobial categories.

"pandrug-resistant" refers to a bacteria strain resistant to all agents in all antimicrobial categories.

"prodrug" refers to the pharmacologically acceptable derivatives of compounds of Formula I, II or III, such as for example amides or esters, whose in vivo biotransformation product generates the biologically active drug. Prodrugs are generally characterized by an increased bio-availability and are readily metabolized into biologically active compounds in vivo.

"solvate" refers to a compound of the invention that contains stoichiometric or sub-stoichiometric amounts of one or more pharmaceutically acceptable solvent molecule such as ethanol or water.

"treat" and "treatment" as used in the invention are meant to include alleviating, attenuating or abrogating a condition or disease and/or its attendant symptoms. "Treat" and "treatment" preferably mean that the bacterial infection is eradicated.

"pharmaceutically acceptable" refers to ingredients of a pharmaceutical composition which are compatible to each other and not deleterious for the patient.

"pharmaceutical carrier" refers to a vehicle or inert medium used as solvent or diluent in which the pharmaceutically active agent is formulated and/or administrated. Non-limiting examples of pharmaceutical carrier includes creams, gels, lotions, solutions, liposomes.

DETAILED DESCRIPTION

The invention relates to compounds of general Formula I:

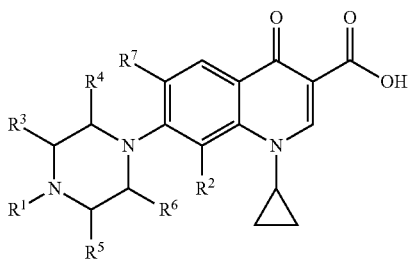

and pharmaceutically acceptable salts, solvates and prodrugs thereof, wherein:

$R^1$ represents a saturated or unsaturated, substituted or unsubstituted, branched or unbranched alkyl group comprising 4 to 20 carbons atoms, preferably 5 to 16, more preferably 5, 6, 7, 8, 9, 10, 11, 12, 13, 14, 15 or 16 carbons, when the alkyl group is substituted, the substituent is selected in the group comprising halo, hydroxyl, oxo, nitro, amido, carboxy, amino, cyano, alkoxy, haloalkoxy, or haloalkyl, $R^2$ represents a substituent selected from the group comprising hydrogen, alkyl, alkene, alkyne, cycloalkyl, aryl, halo, hydroxyl, oxo, nitro, amido, carboxy, amino, cyano, alkoxy, haloalkoxy, or haloalkyl, preferably $R^2$ represents a substituent selected from the group comprising hydrogen, methyl, methoxy, ethoxy, chloro, fluoro, more preferably $R^2$ is a hydrogen atom or methoxy group, even more preferably $R^2$ is a methoxy group, $R^3$, $R^4$, $R^5$ and $R^6$ may be identical or different and each represents a substituent selected from hydrogen, alkyl, alkene, alkyne, cycloalkyl, aryl, halo, hydroxyl, oxo, nitro, amido, carboxy, amino, cyano, alkoxy, haloalkoxy, or haloalkyl, preferably $R^3$, $R^4$, $R^5$ and $R^6$ are identical and represent each a hydrogen atom, $R^7$ represents a substituent selected from hydrogen, alkyl, alkene, alkyne, cycloalkyl, aryl, halo, hydroxyl, oxo, nitro, amido, carboxy, amino, cyano, alkoxy, haloalkoxy, or haloalkyl, preferably $R^7$ represents a hydrogen, —NH$_2$ or fluoro, with the condition that the compounds of Formula I are not:
7-(4-butylpiperazin-1-yl)-1-cyclopropyl-6-fluoro-4-oxo-1,4-dihydroquinoline-3-carboxylic acid,
1-cyclopropyl-6-fluoro-7-(4-heptylpiperazin-1-yl)-4-oxo-1,4-dihydroquinoline-3-carboxylic acid,
7-(4-butyl-3-methylpiperazin-1-yl)-1-cyclopropyl-6-fluoro-4-oxo-1,4-dihydroquinoline-3-carboxylic acid,
1-cyclopropyl-6-fluoro-7-(4-hexyl-3-methylpiperazin-1-yl)-4-oxo-1,4-dihydroquinoline-3-carboxylic acid,
1-cyclopropyl-6-fluoro-7-(4-(4-hydroxybutyl)piperazin-1-yl)-4-oxo-1,4-dihydroquinoline-3-carboxylic acid,
with the condition that when $R^2$ is a hydrogen and $R^7$ is a fluorine, $R^3$, $R^4$, $R^5$ and $R^6$ are not a methyl group.

According to an embodiment, the invention relates to compounds of general Formula I wherein when $R^2$, $R^3$, $R^4$, $R^5$ and $R^6$ are hydrogen and $R^7$ is a fluorine, $R^1$ is not a C1-C7 alkyl or $R^1$ is not an alkyl substituted by an oxo group. In one embodiment, the invention relates to compounds of general Formula I wherein when $R^2$, $R^3$, $R^4$, $R^5$ and $R^6$ are hydrogen and $R^7$ is a fluorine, $R^1$ is not a pentyl or an hexyl group or $R^1$ is not an alkyl substituted by an oxo group.

According to one embodiment, when $R^2$, $R^3$, $R^4$, $R^5$ and $R^6$ are hydrogen and $R^7$ is a fluorine, $R^1$ is not a pentyl or an hexyl group. In one embodiment, preferred compounds of general Formula I does not comprise 1-cyclopropyl-6-fluoro-4-oxo-7-(4-pentylpiperazin-1-yl)-1,4-dihydroquinoline-3-carboxylic acid. In one embodiment, preferred compounds of general Formula I does not comprise 1-cyclopropyl-6-fluoro-7-(4-hexylpiperazin-1-yl)-4-oxo-1,4-dihydroquinoline-3-carboxylic acid.

According to one embodiment, compounds of general Formula I does not comprise compounds wherein $R^1$ is an alkyl group substituted with at least one oxo function. In one embodiment, compounds of general Formula I does not comprise compounds wherein $R^1$ is an alkyl group substituted with only one oxo function.

According to one embodiment, when $R^2$, $R^3$, $R^4$, $R^5$ and $R^6$ are hydrogen and $R^7$ is a fluorine, $R^1$ is not an alkyl group substituted with an oxo function. In one embodiment, compounds of general Formula I does not comprise the following compounds:
7-(4-butyrylpiperazin-1-yl)-1-cyclopropyl-6-fluoro-4-oxo-1,4-dihydroquinoline-3-carboxylic acid;
1-cyclopropyl-6-fluoro-4-oxo-7-(4-pentanoylpiperazin-1-yl)-1,4-dihydroquinoline-3-carboxylic acid;
1-cyclopropyl-6-fluoro-7-(4-hexanoylpiperazin-1-yl)-4-oxo-1,4-dihydroquinoline-3-carboxylic acid;

1-cyclopropyl-6-fluoro-7-(4-heptanoylpiperazin-1-yl)-4-oxo-1,4-dihydroquinoline-3-carboxylic acid;
1-cyclopropyl-6-fluoro-7-(4-nonanoylpiperazin-1-yl)-4-oxo-1,4-dihydroquinoline-3-carboxylic acid;
1-cyclopropyl-7-(4-decanoylpiperazin-1-yl)-6-fluoro-4-oxo-1,4-dihydroquinoline-3-carboxylic acid;
1-cyclopropyl-7-(4-dodecanoylpiperazin-1-yl)-6-fluoro-4-oxo-1,4-dihydroquinoline-3-carboxylic acid;
1-cyclopropyl-6-fluoro-4-oxo-7-(4-tetradecanoylpiperazin-1-yl)-1,4-dihydroquinoline-3-carboxylic acid;
1-cyclopropyl-6-fluoro-4-oxo-7-(4-palmitoylpiperazin-1-yl)-1,4-dihydroquinoline-3-carboxylic acid;
1-cyclopropyl-6-fluoro-4-oxo-7-(4-(3-oxobutyl)piperazin-1-yl)-1,4-dihydroquinoline-3-carboxylic acid.

According to one embodiment, $R^1$ is not an alkyl group substituted by more than one substituent selected in the group comprising halo, hydroxyl, oxo, nitro, amido, carboxy, amino, cyano, alkoxy, haloalkoxy, or haloalkyl. In one embodiment, $R^1$ is not an alkyl group substituted by more than one substituent selected in the group comprising halo, hydroxyl, nitro, amido, carboxy, amino, cyano, alkoxy, haloalkoxy, or haloalkyl. In one embodiment, $R^1$ is not an alkyl group substituted by both a carboxy and an oxo group. In one embodiment, $R^1$ is not an alkyl group substituted by both an oxo and an amino group.

According to an embodiment, preferred compounds of general Formula I are those wherein:
$R^1$ represents a saturated or unsaturated, substituted or unsubstituted, branched or unbranched alkyl group comprising 4 to 20 carbons atoms, preferably 5 to 16, more preferably 5, 6, 7, 8, 9, 10, 11, 12, 13, 14, 15 or 16 carbons, when the alkyl group is substituted, the substituent is selected in the group comprising halo, hydroxyl, nitro, amido, carboxy, amino, cyano, alkoxy, haloalkoxy, or haloalkyl, and
$R^2$, $R^3$, $R^4$, $R^5$, $R^6$ and $R^7$ are as defined above.

According to an embodiment, preferred compounds of general Formula I are those wherein:
$R^1$ represents a saturated or unsaturated, substituted or unsubstituted, branched or unbranched alkyl group comprising 8 to 12 carbons atoms, preferably 8, 9, 10, 11, 12 carbons, more preferably comprising 8, 9 or 10 carbons atoms, when the alkyl group is substituted, the substituent is selected in the group comprising halo, hydroxyl, oxo, nitro, amido, carboxy, amino, cyano, alkoxy, haloalkoxy, or haloalkyl, and
$R^2$, $R^3$, $R^4$, $R^5$, $R^6$ and $R^7$ are as defined above.

In one embodiment, preferred compounds of general Formula I are those wherein $R^1$ is octyl, nonyl, decyl, undecyl or dodecyl group; preferably $R^1$ is octyl, nonyl or decyl group.

According to an embodiment, preferred compounds of general Formula I are those wherein:
$R^1$ represents a saturated or unsaturated, substituted or unsubstituted, branched or unbranched alkyl group comprising 7 to 12 carbons atoms, preferably 7, 8, 9, 10, 11, 12 carbons, more preferably comprising 7, 8, 9 or 10 carbons atoms, when the alkyl group is substituted, the substituent is selected in the group comprising halo, hydroxyl, oxo, nitro, amido, carboxy, amino, cyano, alkoxy, haloalkoxy, or haloalkyl, and
$R^2$, $R^3$, $R^4$, $R^5$, $R^6$ and $R^7$ are as defined above.

In one embodiment, preferred compounds of general Formula I are those wherein $R^1$ is heptyl, octyl, nonyl, decyl, undecyl or dodecyl group; preferably $R^1$ is heptyl, octyl, nonyl or decyl group.

According to an embodiment, the invention relates to compounds of general Formula II:

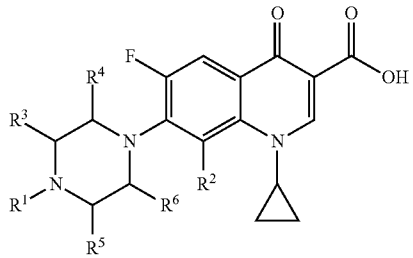

and pharmaceutically acceptable salts, solvates or prodrugs thereof, corresponding to the compounds of Formula I wherein $R^7$ is a fluorine atom.

According to another embodiment, the invention relates to compounds of general Formula III:

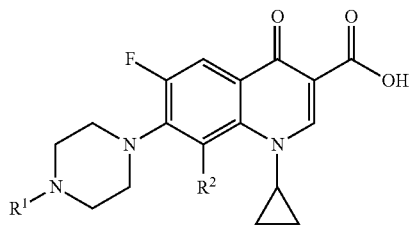

and pharmaceutically acceptable salts, solvates or prodrugs thereof, corresponding to compounds of general Formula II wherein $R^3$, $R^4$, $R^5$, $R^6$ are identical and represent a hydrogen atom.

In a preferred embodiment, the invention relates to compounds of general Formula III:

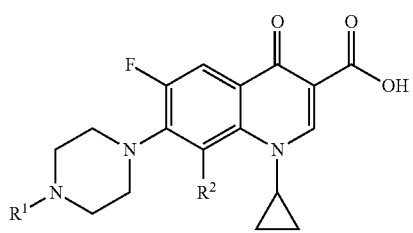

and pharmaceutically acceptable salts, solvates or prodrugs thereof, wherein $R^2$ is a hydrogen atom or methoxy group, even more preferably $R^2$ is a methoxy group and $R^1$ is as defined above.

According to an embodiment, preferred compounds of general Formula III are those wherein:
$R^2$ is methoxy group, and
$R^1$ represents a saturated or unsaturated, substituted or unsubstituted, branched or unbranched alkyl group comprising 8 to 12 carbons atoms, preferably 8, 9, 10, 11, 12 carbons, more preferably comprising 8, 9 or 10 carbons atoms, when the alkyl group is substituted, the substituent is selected in the group comprising halo, hydroxyl, oxo, nitro, amido, carboxy, amino, cyano, alkoxy, haloalkoxy, or haloalkyl.

In a preferred embodiment, preferred compounds of general Formula III are those wherein $R^2$ is methoxy group and $R^1$ is octyl, nonyl, decyl, undecyl or dodecyl group; preferably $R^2$ is methoxy group and $R^1$ is octyl, nonyl or decyl group.

According to an embodiment, preferred compounds of general Formula III are those wherein:
- $R^2$ is methoxy group, and
- $R^1$ represents a saturated or unsaturated, substituted or unsubstituted, branched or unbranched alkyl group comprising 7 to 12 carbons atoms, preferably 7, 8, 9, 10, 11, 12 carbons, more preferably comprising 7, 8, 9 or 10 carbons atoms, when the alkyl group is substituted, the substituent is selected in the group comprising halo, hydroxyl, oxo, nitro, amido, carboxy, amino, cyano, alkoxy, haloalkoxy, or haloalkyl.

In a preferred embodiment, preferred compounds of general Formula III are those wherein $R^2$ is methoxy group and $R^1$ is heptyl, octyl, nonyl, decyl, undecyl or dodecyl group; preferably $R^2$ is methoxy group and $R^1$ is heptyl, octyl, nonyl or decyl group.

In a preferred embodiment, the compounds of the invention are those listed in table 1:

TABLE 1

| Cpd no | Structure and chemical name |
|---|---|
| 1 (Quin 15) | 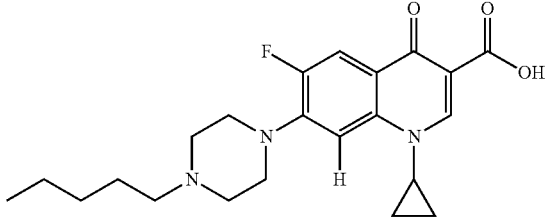 [SMILES: CCCCCN1CCN(c2cc3c(cc2F)c(=O)c(C(=O)O)cn3C2CC2)CC1] 1-cyclopropyl-6-fluoro-4-oxo-7-(4-pentylpiperazin-1-yl)-1,4-dihydroquinoline-3-carboxylic acid |
| 2 | 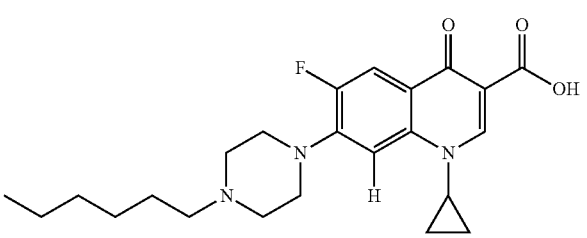 [SMILES: CCCCCCN1CCN(c2cc3c(cc2F)c(=O)c(C(=O)O)cn3C2CC2)CC1] 1-cyclopropyl-6-fluoro-7-(4-hexylpiperazin-1-yl)-4-oxo-1,4-dihydroquinoline-3-carboxylic acid |
| 3 | 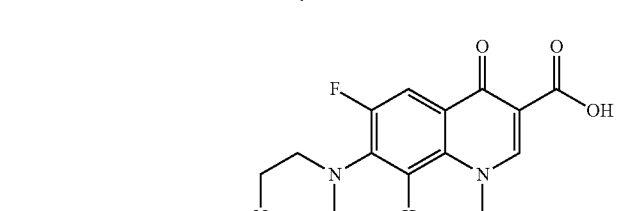 1-cyclopropyl-6-fluoro-7-(4-heptylpiperazin-1-yl)-4-oxo-1,4-dihydroquinoline-3-carboxylic acid |
| 4 (Quin 16) | 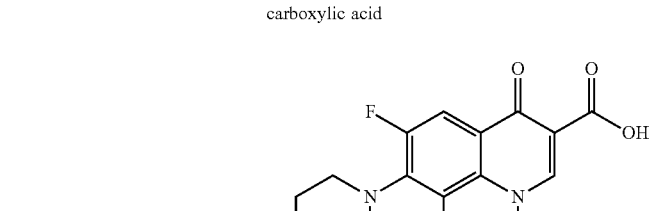 1-cyclopropyl-6-fluoro-7-(4-octylpiperazin-1-yl)-4-oxo-1,4-dihydroquinoline-3-carboxylic acid |

TABLE 1-continued

| Cpd no | Structure and chemical name |
|---|---|
| 5 | 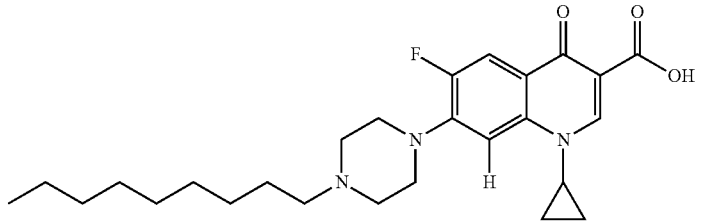 [SMILES: CCCCCCCCCN1CCN(c2cc3c(cc2F)c(=O)c(C(=O)O)cn3C2CC2)CC1]<br>1-cyclopropyl-6-fluoro-7-(4-nonylpiperazin-1-yl)-4-oxo-1,4-dihydroquinoline-3-carboxylic acid |
| 6 (Quin 9) | 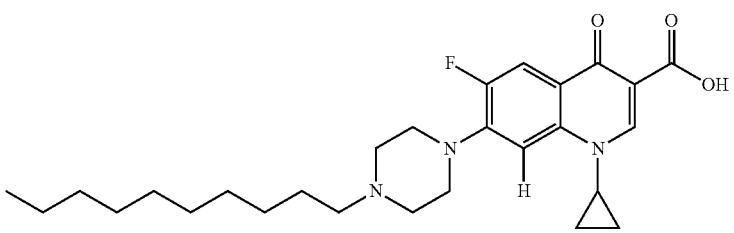 [SMILES: CCCCCCCCCCN1CCN(c2cc3c(cc2F)c(=O)c(C(=O)O)cn3C2CC2)CC1]<br>1-cyclopropyl-7-(4-decylpiperazin-1-yl)-6-fluoro-4-oxo-1,4-dihydroquinoline-3-carboxylic acid |
| 7 | 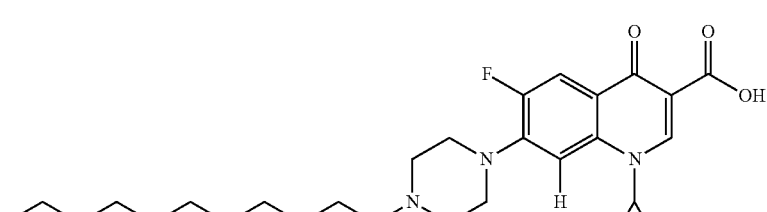<br>1-cyclopropyl-6-fluoro-4-oxo-7-(4-undecylpiperazin-1-yl)-1,4-dihydroquinoline-3-carboxylic acid |
| 8 | 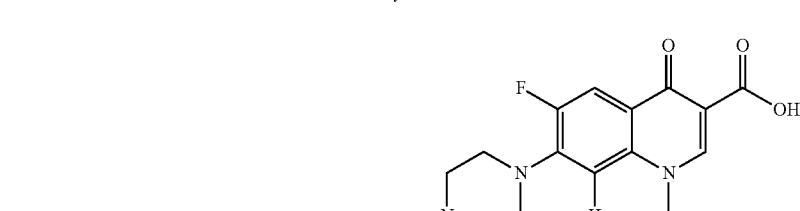<br>1-cyclopropyl-7-(4-dodecylpiperazin-1-yl)-6-fluoro-4-oxo-1,4-dihydroquinoline-3-carboxylic acid |
| 9 | 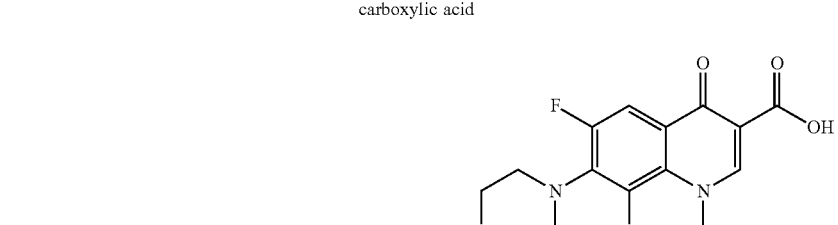<br>1-cyclopropyl-6-fluoro-4-oxo-7-(4-tridecylpiperazin-1-yl)-1,4-dihydroquinoline-3-carboxylic acid |

TABLE 1-continued

| Cpd no | Structure and chemical name |
|---|---|
| 10 | 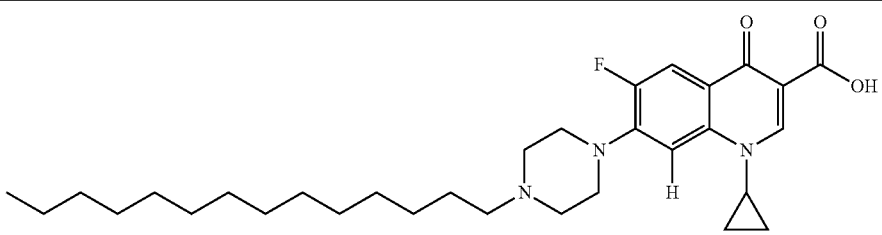
1-cyclopropyl-6-fluoro-4-oxo-7-(4-tetradecylpiperazin-1-yl)-1,4-dihydroquinoline-3-carboxylic acid |
| 11 | 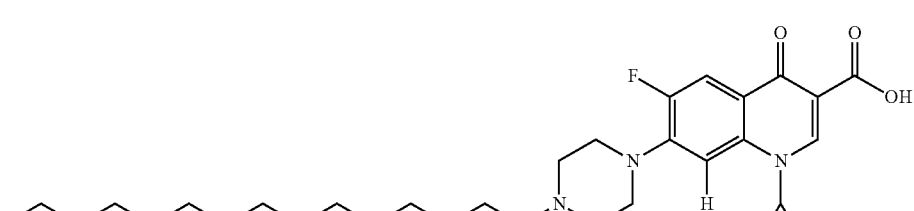
1-cyclopropyl-6-fluoro-4-oxo-7-(4-pentadecylpiperazin-1-yl)-1,4-dihydroquinoline-3-carboxylic acid |
| 12 (Quin 10) | 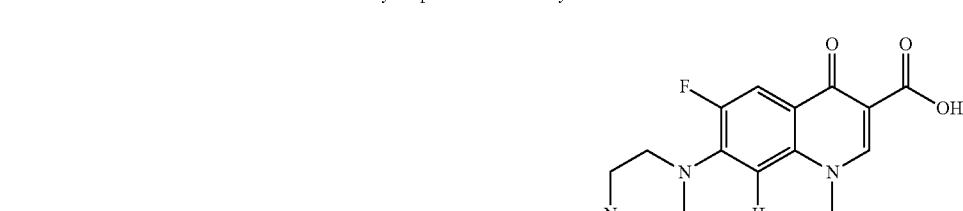
1-cyclopropyl-6-fluoro-7-(4-hexadecylpiperazin-1-yl)-4-oxo-1,4-dihydroquinoline-3-carboxylic acid |
| 13 (Quin 17) | 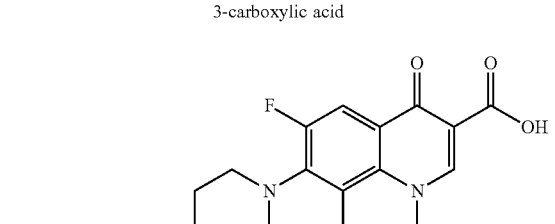
1-cyclopropyl-6-fluoro-8-methoxy-4-oxo-7-(4-pentylpiperazin-1-yl)-1,4-dihydroquinoline-3-carboxylic acid |
| 14 | 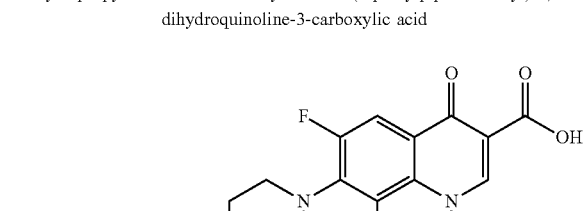
1-cyclopropyl-6-fluoro-7-(4-hexylpiperazin-1-yl)-8-methoxy-4-oxo-1,4-dihydroquinoline-3-carboxylic acid |

TABLE 1-continued

| Cpd no | Structure and chemical name |
|---|---|
| 15 | 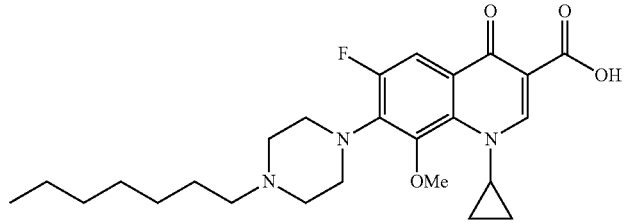 [SMILES: CCCCCCCN1CCN(c2c(F)cc3c(=O)c(C(=O)O)cn(C4CC4)c3c2OC)CC1]<br>1-cyclopropyl-6-fluoro-7-(4-heptylpiperazin-1-yl)-8-methoxy-4-oxo-1,4-dihydroquinoline-3-carboxylic acid |
| 16<br>(Quin 18) | 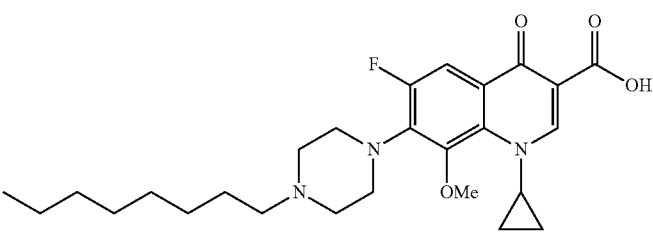 [SMILES: CCCCCCCCN1CCN(c2c(F)cc3c(=O)c(C(=O)O)cn(C4CC4)c3c2OC)CC1]<br>1-cyclopropyl-6-fluoro-8-methoxy-7-(4-octylpiperazin-1-yl)-4-oxo-1,4-dihydroquinoline-3-carboxylic acid |
| 17 | 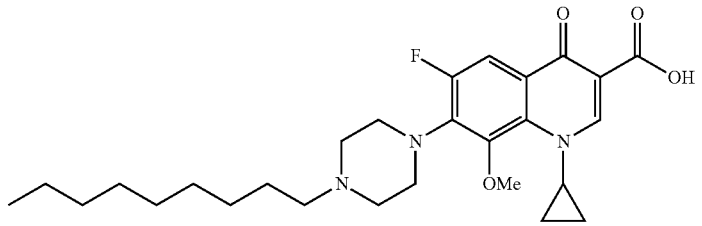 [SMILES: CCCCCCCCCN1CCN(c2c(F)cc3c(=O)c(C(=O)O)cn(C4CC4)c3c2OC)CC1]<br>1-cyclopropyl-6-fluoro-8-methoxy-7-(4-nonylpiperazin-1-yl)-4-oxo-1,4-dihydroquinoline-3-carboxylic acid |
| 18<br>(Quin 19) | 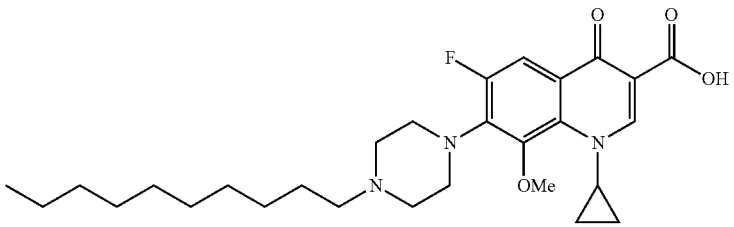 [SMILES: CCCCCCCCCCN1CCN(c2c(F)cc3c(=O)c(C(=O)O)cn(C4CC4)c3c2OC)CC1]<br>1-cyclopropyl-7-(4-decylpiperazin-1-yl)-6-fluoro-8-methoxy-4-oxo-1,4-dihydroquinoline-3-carboxylic acid |
| 19 | 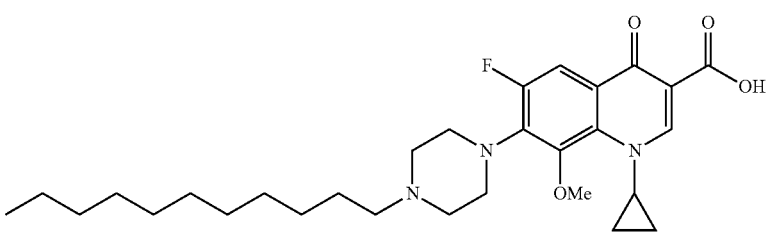 [SMILES: CCCCCCCCCCCN1CCN(c2c(F)cc3c(=O)c(C(=O)O)cn(C4CC4)c3c2OC)CC1]<br>1-cyclopropyl-6-fluoro-8-methoxy-4-oxo-7-(4-undecylpiperazin-1-yl)-1,4-dihydroquinoline-3-carboxylic acid |

TABLE 1-continued

| Cpd no | Structure and chemical name |
|---|---|
| 20 | 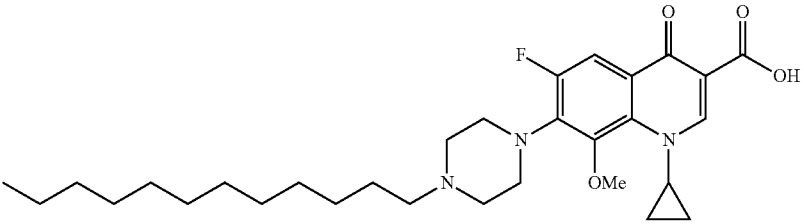 [SMILES: CCCCCCCCCCCCN1CCN(c2c(F)cc3c(=O)c(C(=O)O)cn(C4CC4)c3c2OC)CC1]<br>1-cyclopropyl-7-(4-dodecylpiperazin-1-yl)-6-fluoro-8-methoxy-4-oxo-1,4-dihydroquinoline-3-carboxylic acid |
| 21 | 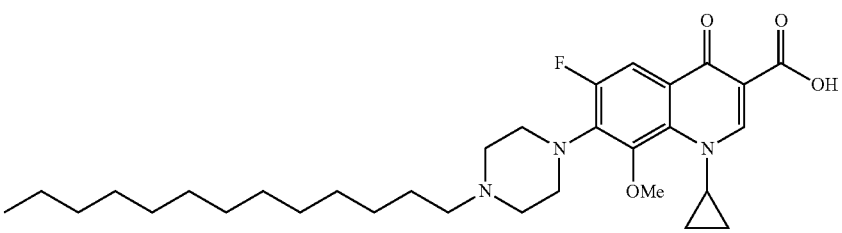 [SMILES: CCCCCCCCCCCCCN1CCN(c2c(F)cc3c(=O)c(C(=O)O)cn(C4CC4)c3c2OC)CC1]<br>1-cyclopropyl-6-fluoro-8-methoxy-4-oxo-7-(4-tridecylpiperazin-1-yl)-1,4-dihydroquinoline-3-carboxylic acid |
| 22 | 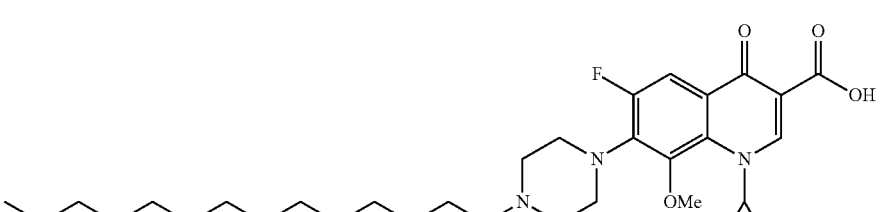<br>1-cyclopropyl-6-fluoro-8-methoxy-4-oxo-7-(4-tetradecylpiperazin-1-yl)-1,4-dihydroquinoline-3-carboxylic acid |
| 23 | 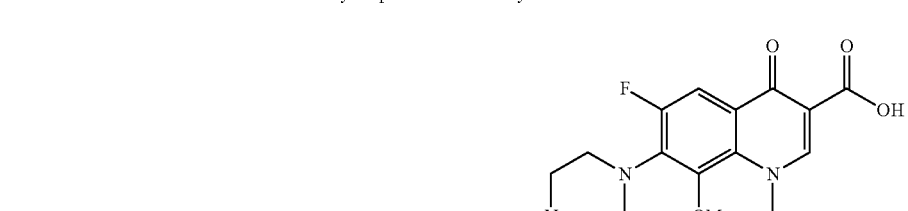<br>1-cyclopropyl-6-fluoro-8-methoxy-4-oxo-7-(4-pentadecylpiperazin-1-yl)-1,4-dihydroquinoline-3-carboxylic acid |
| 24 (Quin 20) | 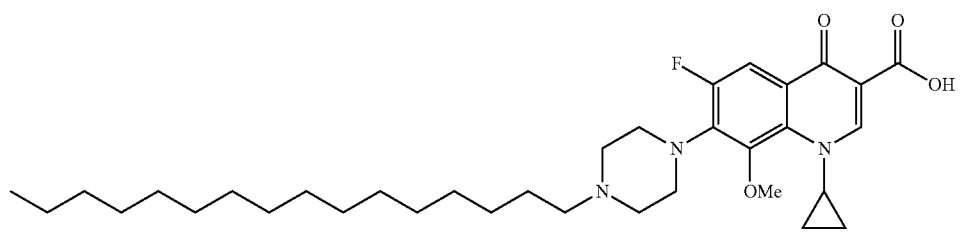 [SMILES: CCCCCCCCCCCCCCCCN1CCN(c2c(F)cc3c(=O)c(C(=O)O)cn(C4CC4)c3c2OC)CC1]<br>1-cyclopropyl-6-fluoro-7-(4-hexadecylpiperazin-1-yl)-8-methoxy-4-oxo-1,4-dihydroquinoline-3-carboxylic acid |

TABLE 1-continued

| Cpd no | Structure and chemical name |
|---|---|
| 25 | 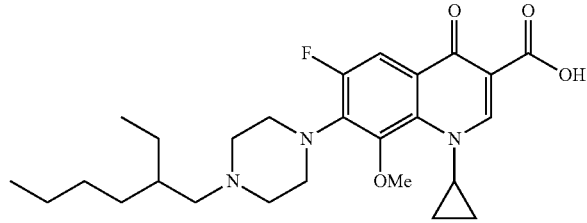 [SMILES: CCCCC(CC)CN1CCN(c2c(F)cc3c(=O)c(C(=O)O)cn(C4CC4)c3c2OC)CC1]<br>1-cyclopropyl-6-fluoro-7-(4-(2-ethylhexyl)piperazin-1-yl)-8-methoxy-4-oxo-1,4-dihydroquinoline-3-carboxylic acid |
| 26 | 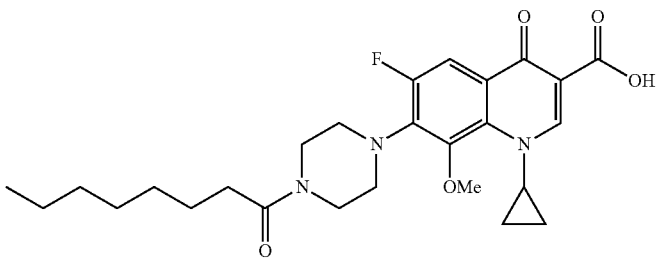 [SMILES: CCCCCCCC(=O)N1CCN(c2c(F)cc3c(=O)c(C(=O)O)cn(C4CC4)c3c2OC)CC1]<br>1-cyclopropyl-6-fluoro-7-(4-octanoylpiperazin-1-yl)-8-methoxy-4-oxo-1,4-dihydroquinoline-3-carboxylic acid |

According to a more preferred embodiment, the compounds of the invention are selected in the group comprising 1-cyclopropyl-6-fluoro-8-methoxy-4-oxo-7-(4-pentylpiperazin-1-yl)-1,4-dihydroquinoline-3-carboxylic acid (Quin 17), 1-cyclopropyl-6-fluoro-8-methoxy-7-(4-octylpiperazin-1-yl)-4-oxo-1,4-dihydroquinoline-3-carboxylic acid (Quin 18), 1-cyclopropyl-7-(4-decylpiperazin-1-yl)-6-fluoro-8-methoxy-4-oxo-1,4-dihydroquinoline-3-carboxylic acid (Quin 19) and 1-cyclopropyl-6-fluoro-7-(4-hexadecylpiperazin-1-yl)-8-methoxy-4-oxo-1,4-dihydroquinoline-3-carboxylic acid (Quin 20).

In another embodiment, the present invention relates to a pharmaceutical composition comprising at least one compound of the invention or a pharmaceutically acceptable salt, solvate or prodrug thereof, and at least one pharmaceutically acceptable carrier, diluent, excipient and/or adjuvant. The invention also covers a pharmaceutical composition which contains, in addition to at least one compound of the invention, or a pharmaceutically acceptable salt, solvate or prodrug thereof as active ingredient, additional therapeutic agents and/or active ingredients.

According to another embodiment, the present invention relates to a medicament comprising at least one compound of the invention or a pharmaceutically acceptable salt, solvate or prodrug thereof.

In another embodiment, the medicament of the invention comprises in addition to at least one compound of the invention, or a pharmaceutically acceptable salt, solvate or prodrug thereof as active ingredients, additional therapeutic agents and/or active ingredients.

Examples of additional therapeutic agents and/or active ingredients include, but are not limited to, fluoroquinolones such as ciprofloxacin, enrofloxacin, gatifloxacin, moxifloxacin, ofloxacin, levofloxacin and sparfloxacin.

According to one embodiment, the compounds having the general Formula III are synthesized according to the pathway described in scheme 1, starting from a fluoroquinolone as precursor by substitution of the fluorine atom in position 7 by a piperazine. Addition of a long alkyl chain in position 4 of the piperazine group provides the final compounds of general Formula III:

Scheme 1: Synthesis of compounds of general formula III

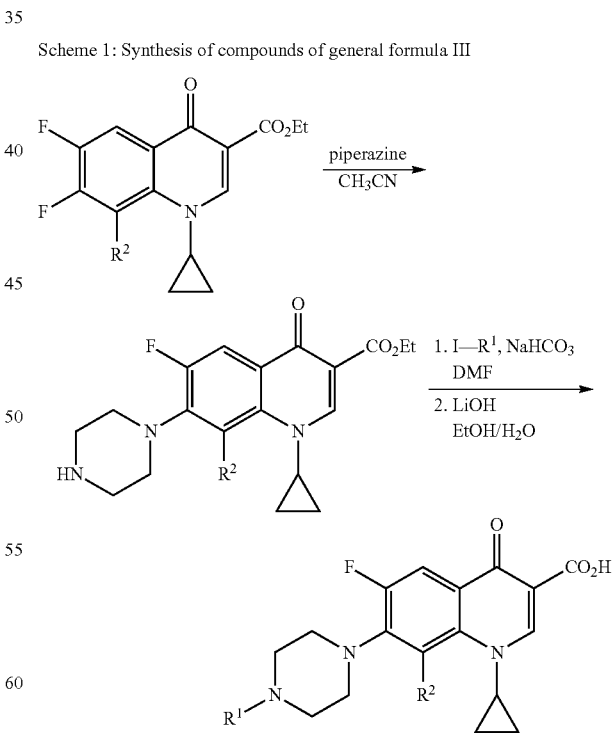

According to an embodiment of the invention, the compounds have the general Formula III wherein $R^2$ is a hydrogen atom and are prepared according to the following pathway starting from 2,4,5-trifluorobenzoic acid:

Scheme 2: Synthesis of compounds of general formula III wherein R² = H

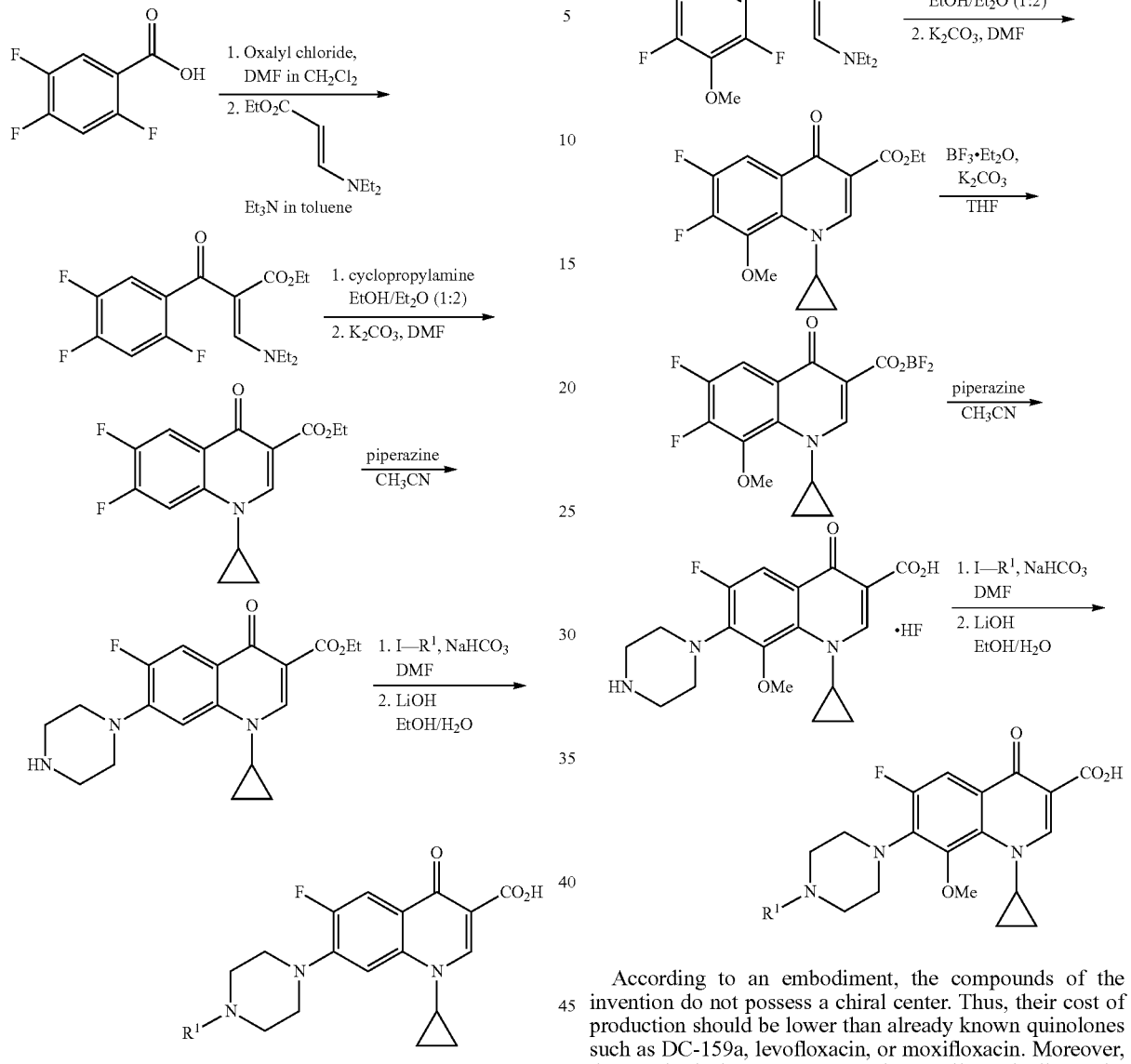

According to another embodiment, the compounds have the general Formula III wherein $R^2$ is a methoxy group and are prepared according to the following pathway starting from 2,4,5-trifluoro-3-methoxy-benzoic acid:

Scheme 3: Synthesis of compounds of general formula III wherein R² = OMe

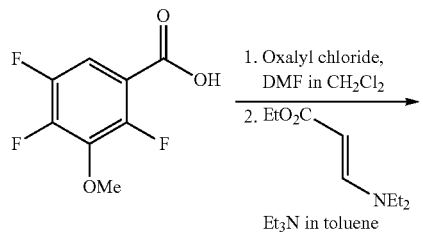

According to an embodiment, the compounds of the invention do not possess a chiral center. Thus, their cost of production should be lower than already known quinolones such as DC-159a, levofloxacin, or moxifloxacin. Moreover, the synthesis is convergent and versatile and allows the preparation of various compounds.

The present invention also relates to the treatment of bacterial infections. Molecules of the family of quinolones and fluoroquinolones are active against a broad scope of bacteria. The mechanism by which quinolones and fluoroquinolones eradicate bacteria is by the inhibition of type II topoisomerases i.e. DNA gyrase (active as a complex of GyrA and GyrB) and DNA topoisomerase IV. Mutations on type II topoisomerase are thus the main way by which bacteria develop resistances to quinolones and fluoroquinolones. In the particular case of *Mycobacterium tuberculosis*, DNA gyrase is the sole type II topoisomerase and is thus the only target of quinolones and fluoroquinolones. Strains of *Mycobacterium tuberculosis* which are resistant to quinolones and fluoroquinolones thus mainly possess at least one mutation in GyrA and/or GyrB subunits of DNA gyrase. Interestingly and without being linked by any theory, the compounds of the present invention inhibit the growth of bacteria whereas they only weakly inhibit DNA gyrase at low concentration.

Without willing to be linked by any theory, the compounds of the invention may inhibit the growth of bacteria by an original mechanism which does not involve DNA gyrase or a mechanism which involves DNA gyrase and another pathway or cellular target.

According to an embodiment, the compounds, the pharmaceutical composition and the medicament of the invention are useful for the treatment of a bacterial infection.

In another embodiment, the compounds of the invention are useful for the treatment of infection caused by at least one bacteria that is a Gram negative or Gram positive bacteria.

Certain bacteria such as *Salmonella, Legionella* and *Mycobacterium*, especially *Mycobacteria tuberculosis* possess the ability to stay alive in macrophages. In one embodiment, the compounds of the invention are able to penetrate into macrophages and have bactericidal activity there.

According to one embodiment, the compounds of the invention are useful for the treatment of bacterial infection caused by at least one bacteria of the genus selected in the group comprising but not limited to *Mycobacterium* such as tuberculosis or *leprae*; Gram positive bacteria such as *Streptococcus, Staphylococcus* or *Bacillus*; enterobacteriaceae such as *Escherichia, Klebsiella, Enterobacter, Proteus, Serratia, Shigella, Citrobacter, Salmonella* or *Yersinia*, non-fermenting Gram negative bacilli such as *Pseudomonas, Alcaligenes*, or *Acitenobacter*; anaerobes such as *Bacteroides, Fusobacterium, Eubacterium, Propionibacterium, Peptococcus, Clostridium, Peptostreptococcus*, or *Veillonella; Helicobacter pylori* and pathogens involved in sexually transmitted infections such as *Neisseria, Haemophilus, Chlamydia*, or *Mycoplasma*.

According to one embodiment, the compounds of the invention are useful for the treatment of bacterial infection caused by at least one bacteria selected in the group comprising but not limited to *Mycobacterium leprae, Mycobacterium tuberculosis* complex such as *Mycobacterium tuberculosis* and non tuberculous mycobacteria such as *Mycobacterium chelonae, Mycobacterium avium, Mycobacterium abscessus, Mycobacterium fortuitum, Mycobacterium malmoense, Mycobacterium gordonae, Mycobacterium terrae, Mycobacterium nonchromogenicium, Mycobacterium simiae, Mycobacterium scrofulaceum, Mycobacterium phlei, Mycobacterium xenopi, Mycobacterium marinum*, or *Mycobacterium ulcerans*; Gram positive bacteria such as *Staphylococcus aureus, Streptococcus pneumoniae, Enterococcus faecalis, Bacillus anthracis, Staphylococcus epidermidis*, or *Streptococcus pyogenes*; enterobacteriaceae such as *Escherichia coli, Klebsiella pneumonia, Enterobacter aerogenes, Enterobacter cloacae, Proteus vulgaris, Shigella flexneri, Serratia marcescens, Citrobacter freundii, Yersinia enterocolitica*, or *Salmonella enteritidis*; non-fermenting Gram negative bacilli such as *Pseudomonas aeruginosa, Acitenobacter baumannii, Burkholderia cepacia*, or *Stenotrophomonas maltophilia*; anaerobes such as *Bacteroides fragilis, Bacteroides distasonis, Bacteroides thetaiotaomicron, Bacteroide vulgatus, Fusobacterium mortiferum, Fusobacterium necrophorum, Fusobacterium varium, Eubacterium lentum, Propionibacterium acens, Clostridium difficile, Clostridium perfringens, Clostridium ramosum, Peptostreptococcus anaerobius, Peptostreptococcus micros*, or *Veillonella parvula; Helicobacter pylori* and pathogens involved in sexually transmitted infections such as *Neisseria gonorrhaeae, Haemophulis ducreyi, Chlamydia trachomatis*, or *Mycoplasma genitallium*.

According to one embodiment, the compounds of the invention are useful for the treatment of bacterial infection caused by at least one bacteria selected in the group comprising but not limited to *Mycobacterium leprae, Mycobacterium tuberculosis* complex such as *Mycobacterium tuberculosis* and non tuberculous mycobacteria such as *Mycobacterium chelonae, Mycobacterium avium* and *avium* complex, *Mycobacterium abscessus, Mycobacterium fortuitum, Mycobacterium malmoense, Mycobacterium gordonae, Mycobacterium terrae, Mycobacterium nonchromogenicium, Mycobacterium simiae, Mycobacterium scrofulaceum, Mycobacterium phlei, Mycobacterium kansasii, Mycobacterium xenopi, Mycobacterium marinum*, or *Mycobacterium ulcerans*; Gram positive bacteria such as *Staphylococcus aureus, Streptococcus pneumoniae, Enterococcus faecalis, Bacillus anthracis, Staphylococcus epidermidis*, or *Streptococcus pyogenes*; enterobacteriaceae such as *Escherichia coli, Klebsiella pneumonia, Enterobacter aerogenes, Enterobacter cloacae, Proteus vulgaris, Shigella flexneri, Serratia marcescens, Citrobacter freundii, Yersinia enterocolitica*, or *Salmonella enteritidis*; non-fermenting Gram negative bacilli such as *Pseudomonas aeruginosa, Acitenobacter baumannii, Burkholderia cepacia*, or *Stenotrophomonas maltophilia*; anaerobes such as *Bacteroides fragilis, Bacteroides distasonis, Bacteroides thetaiotaomicron, Bacteroide vulgatus, Fusobacterium mortiferum, Fusobacterium necrophorum, Fusobacterium varium, Eubacterium lentum, Propionibacterium acens, Clostridium difficile, Clostridium perfringens, Clostridium ramosum, Peptostreptococcus anaerobius, Peptostreptococcus micros*, or *Veillonella parvula; Helicobacter pylori* and pathogens involved in sexually transmitted infections such as *Neisseria gonorrhaeae, Haemophulis ducreyi, Chlamydia trachomatis*, or *Mycoplasma genitallium*.

In a preferred embodiment, the compounds of the invention are useful for the treatment of bacterial infections caused by *Mycobacterium tuberculosis* wild-type, but also MDR, XDR strains, and PDR strains.

According to one embodiment, the compounds of the invention are useful in the treatment of an infection caused by at least one multidrug-resistant, extensively drug-resistant or pandrug-resistant strain of a bacteria selected in the group comprising but not limited to *Mycobacterium leprae, Mycobacterium tuberculosis* complex such as *Mycobacterium tuberculosis* and non tuberculous mycobacteria such as *Mycobacterium chelonae, Mycobacterium avium, Mycobacterium abscessus, Mycobacterium fortuitum, Mycobacterium malmoense, Mycobacterium gordonae, Mycobacterium terrae, Mycobacterium nonchromogenicium, Mycobacterium simiae, Mycobacterium scrofulaceum, Mycobacterium phlei, Mycobacterium xenopi, Mycobacterium marinum*, or *Mycobacterium ulcerans*; Gram positive bacteria such as *Staphylococcus aureus, Streptococcus pneumoniae, Enterococcus faecalis, Bacillus anthracis, Staphylococcus epidermidis*, or *Streptococcus pyogenes*; enterobacteriaceae such as *Escherichia coli, Klebsiella pneumonia, Enterobacter aerogenes, Enterobacter cloacae, Proteus vulgaris, Shigella flexneri, Serratia marcescens, Citrobacter freundii, Yersinia enterocolitica*, or *Salmonella enteritidis*; non-fermenting Gram negative bacilli such as *Pseudomonas aeruginosa, Acitenobacter baumannii, Burkholderia cepacia*, or *Stenotrophomonas maltophilia*; anaerobes such as *Bacteroides fragilis, Bacteroides distasonis, Bacteroides thetaiotaomicron, Bacteroide vulgatus, Fusobacterium mortiferum, Fusobacterium necrophorum, Fusobacterium varium, Eubacterium lentum, Propionibacterium acens, Clostridium difficile, Clostridium perfringens, Clostridium ramosum, Peptostreptococcus anaerobius, Peptostreptococcus micros*, or *Veillonella parvula; Helicobacter*

*pylori* and pathogens involved in sexually transmitted infections such as *Neisseria gonorrhaeae, Haemophulis ducreyi, Chlamydia trachomatis*, or *Mycoplasma genitallium*.

According to one embodiment, the compounds of the invention are useful in the treatment of an infection caused by at least one multidrug-resistant, extensively drug-resistant or pandrug-resistant strain of a bacteria selected in the group comprising but not limited to *Mycobacterium leprae, Mycobacterium tuberculosis* complex such as *Mycobacterium tuberculosis* and non tuberculous mycobacteria such as *Mycobacterium chelonae, Mycobacterium avium* and *avium* complex, *Mycobacterium abscessus, Mycobacterium fortuitum, Mycobacterium malmoense, Mycobacterium gordonae, Mycobacterium terrae, Mycobacterium nonchromogenicium, Mycobacterium simiae, Mycobacterium scrofulaceum, Mycobacterium phlei, Mycobacterium kansasii, Mycobacterium xenopi, Mycobacterium marinum*, or *Mycobacterium ulcerans*; Gram positive bacteria such as *Staphylococcus aureus, Streptococcus pneumoniae, Enterococcus faecalis, Bacillus anthracis, Staphylococcus epidermidis*, or *Streptococcus pyogenes*; enterobacteriaceae such as *Escherichia coli, Klebsiella pneumonia, Enterobacter aerogenes, Enterobacter cloacae, Proteus vulgaris, Shigella flexneri, Serratia marcescens, Citrobacter freundii, Yersinia enterocolitica*, or *Salmonella enteritidis*; non-fermenting Gram negative bacilli such as *Pseudomonas aeruginosa, Acitenobacter baumannii, Burkholderia cepacia*, or *Stenotrophomonas maltophilia*; anaerobes such as *Bacteroides fragilis, Bacteroides distasonis, Bacteroides thetaiotaomicron, Bacteroide vulgatus, Fusobacterium mortiferum, Fusobacterium necrophorum, Fusobacterium varium, Eubacterium lentum, Propionibacterium acens, Clostridium difficile, Clostridium perfringens, Clostridium ramosum, Peptostreptococcus anaerobius, Peptostreptococcus micros*, or *Veillonella parvula; Helicobacter pylori* and pathogens involved in sexually transmitted infections such as *Neisseria gonorrhaeae, Haemophulis ducreyi, Chlamydia trachomatis*, or *Mycoplasma genitallium*.

According to one embodiment, the compounds of the invention are useful in the treatment of an infection caused by at least one multidrug-resistant, extensively drug-resistant or pandrug-resistant strain of a bacteria, said bacteria being preferably *Mycobacterium tuberculosis*.

According to another embodiment of the invention, the bacteria strain is fluoroquinolone-resistant mainly due to one or multiple mutation(s) in the GyrA subunit of the DNA gyrase, due to one or multiple mutation(s) in the GyrB subunit of the DNA gyrase, or due to multiple mutations in the GyrA and GyrB subunits of the DNA gyrase.

According to an embodiment, *Mycobacterium tuberculosis* is fluoroquinolone-resistant due to one mutation in the GyrA subunit of the DNA gyrase, said mutation being selected in a group comprising but not limited to D89N, D94A, D94N, D94G, D94H, D94F, D94Y, D94V, A74S, A90V, T80A, G88A, G88C, S91A, and S91P (Maruri et al., *J. Antimicrob. Chemother.*, 2012, p1-13).

According to an embodiment, *Mycobacterium tuberculosis* is fluoroquinolone-resistant due to one mutation in the GyrB subunit of the DNA gyrase, said mutation being selected in a group comprising but not limited to N538D, N538T, D500A, D500N, D500H, T539P, E540D, and E540V (Maruri et al., *J. Antimicrob. Chemother.*, 2012, p1-13).

According to another embodiment, *Mycobacterium tuberculosis* is fluoroquinolone-resistant due to multiple mutations in the GyrA subunit of the DNA gyrase, said multiple mutation being selected in the group comprising but not limited to A74S+D94G, T80A+A90E, T80A+A90G+D94G, G88A+A90V, G88A+D94T, A90V+G94A, A90V+P102H, A90V+S91P, A90V+D94N, A90V+D94G, S91P+D94G, S91P+D94G+G94A, D94A+D94Y, D94N+D94G, D94N+D94G+D94Y, and D94G+D94A (Maruri et al., *J. Antimicrob. Chemother.*, 2012, p1-13).

According to another embodiment, *Mycobacterium tuberculosis* is fluoroquinolone-resistant due to multiple mutations in the GyrA and GyrB subunits of the DNA gyrase, said multiple mutation being selected in a group comprising but not limited to A90V+T500P, D94A+D461N, D94G+N499K, D94G+N499T, and D94N+A504V (Maruri et al., *J. Antimicrob. Chemother.*, 2012, p1-13).

According to one embodiment, the compounds of the invention are useful as initial treatment. According to another embodiment, the compounds of the invention are useful as second-line therapy.

The present invention also relates to a method for treating a bacterial infection in a subject in need thereof, said method comprising administering to the subject a therapeutically effective amount of at least one compound or composition of the invention as described here above.

Preferably, the subject is a warm-blooded animal, more preferably a human.

According to one embodiment, the compounds of the invention may be administered as part of a combination therapy. Thus, are included within the scope of the present invention embodiments comprising coadministration of, and compositions and medicaments which contain, in addition to a compound of the present invention, a pharmaceutically acceptable solvate thereof as active ingredient, additional therapeutic agents and/or active ingredients.

In the above-described embodiment combinations of the present invention, the compound of invention, a pharmaceutically acceptable solvate thereof and other therapeutic active agents may be administered in terms of dosage forms either separately or in conjunction with each other, and in terms of their time of administration, either serially or simultaneously. Thus, the administration of one component agent may be prior to, concurrent with, or subsequent to the administration of the other component agent(s).

Generally, for pharmaceutical use, the compounds of the invention may be formulated as a pharmaceutical preparation comprising at least one compound of the invention and at least one pharmaceutically acceptable carrier, diluent, excipient and/or adjuvant, and optionally one or more further pharmaceutically active compounds.

By means of non-limiting examples, such a formulation may be in a form suitable for oral administration, for parenteral administration (such as by intravenous, intramuscular or subcutaneous injection or intravenous infusion), for topical administration (including ocular), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is made to the latest edition of Remington's Pharmaceutical Sciences.

According to one embodiment, the compounds of the invention are administered per os (oral administration) or by intravenous means.

Some preferred, but non-limiting examples of such preparations include tablets, pills, powders, lozenges, sachets, cachets, elixirs, suspensions, emulsions, solutions, syrups, aerosols, ointments, cremes, lotions, soft and hard gelatin capsules, suppositories, drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other substances that are commonly used in pharmaceutical formulations, such as lubricating agents, wetting agents, emulsifying and suspending agents, dispersing agents, desintegrants, bulking agents, fillers, preserving agents, sweetening agents, flavoring agents, flow regulators, release agents, etc. The compositions may also be formulated so as to provide rapid, sustained or delayed release of the active compound(s) contained therein.

The pharmaceutical preparations of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use.

Usually, depending on the condition to be prevented or treated and the route of administration, the active compound of the invention will usually be administered between 0.001 to 200 mg per kilogram body weight, preferably between 1 and 160 mg per kilogram body weight, for example about 25, 50, 100, 150 mg per kilogram body weight of the patient per day, which may be administered as a single daily dose, divided over one or more daily doses, or essentially continuously, e.g. using a drip infusion.

According to one embodiment, the compound of invention is administered at a concentration ranging from 0 to 40 mg/ml; preferably at a concentration of 10 or 20 mg/ml.

According to one embodiment, the compound of invention is administered at a volume ranging from more than 0 to 100 ml/kg; preferably the volume of administration is 10 ml/kg.

EXAMPLES

The present invention is further illustrated by the following examples.

1. Synthesis of the Compounds of the Invention

Materials and Methods

All materials were obtained from commercial suppliers and used without further purification. Thin-layer chromatography was performed on TLC plastic sheets of silica gel 60F254 (layer thickness 0.2 mm) from Merck. Column chromatography purification was carried out on silica gel 60 (70-230 mesh ASTM, Merck). Melting points were determined either on a digital melting point apparatus (Electrothermal IA 8103) and are uncorrected or on a Kofler bench type WME (Wagner & Munz). IR, $^1$H, $^{19}$F and $^{13}$C NMR spectra confirmed the structures of all compounds. IR spectra were recorded on a Perkin Elmer Spectrum 100 FT-IR spectrometer and NMR spectra were recorded, using $CDCl_3$, $CD_3CN$, D20 or DMSO-$d_6$ as solvent, on a BRUKER AC 300 or 400 spectrometer at 300 or 400 MHz for $^1$H, 75 or 100 MHz for $^{13}$C and 282 or 377 MHz for $^{19}$F spectra. Chemical shifts (δ) were expressed in parts per million relative to the signal indirectly (i) to $CHCl_3$ (δ 7.27) for $^1$H and (ii) to $CDCl_3$ (δ 77.2) for $^{13}$C and directly (iii) to $CFCl_3$ (internal standard) (δ 0) for $^{19}$F. Chemical shifts are given in ppm and peak multiplicities are designated as follows: s, singlet; br s, broad singlet; d, doublet; dd, doublet of doublet; t, triplet; q, quadruplet; quint, quintuplet; m, multiplet. High resolution mass spectra (HRMS) were obtained from the "Service Central d'analyse de Solaize" (Centre Nationale de la Recherche Scientifique) and were recorded on a Waters spectrometer using electrospray ionization-TOF (ESI-TOF).

Results

Example 1:

Synthesis of the Precursor for the Preparation of Compounds of General Formula III Wherein $R^2$ is a Hydrogen Atom

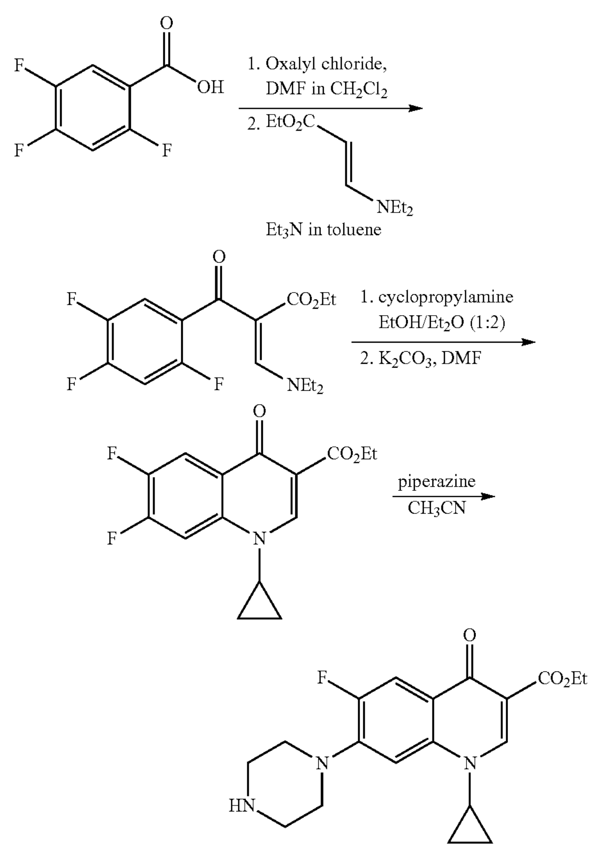

Ethyl α(Z)-[(diethylamino)methylene]-2,4,5-trifluoro-β-oxo-benzenepropanoate

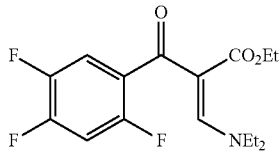

Figure 1:
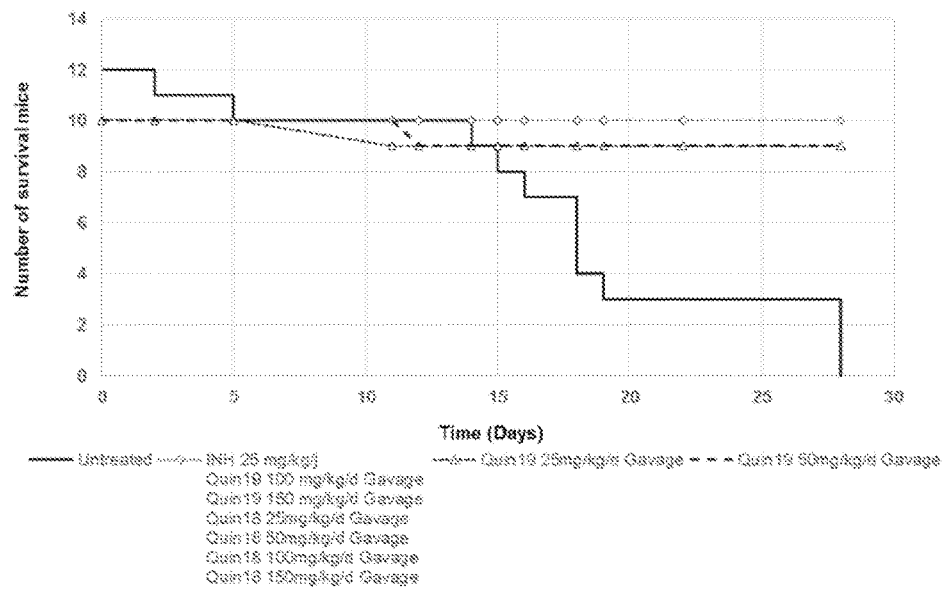
FIG. 1 is a graph showing the evolution of survival mice infected with wild-type *M. tuberculosis* strain H37rv and treated by gavage with Quin18 and Quin19.

An anhydrous CH$_2$Cl$_2$ solution (50 mL) of 2,4,5-trifluorobenzoic acid (3.49 g, 19.81 mmol), oxalyl chloride (2.18 mL, 25.75 mmol) and five drops of DMF was stirred for 24 h at room temperature. The reaction mixture was then subjected to concentrated evaporation under reduced pressure, solubilized in toluene (30 mL) and added dropwise to a toluene solution (20 mL) of triethylamine (8.26 mL, 59.43 mmol) and ethyl 3-(diethylamino)-2E-propenoate (4.40 g, 25.75 mmol). After 18 h of stirring at 90° C., the cooled reaction mixture was washed with water. The organic layer was dried over Na$_2$SO$_4$, filtered and evaporated. The crude residue was purified by flash chromatography on silica gel (95:5 to 60:40 hexane/AcOEt) to give Ethyl α(Z)-[(diethylamino)methylene]-2,4,5-trifluoro-β-oxo-benzenepropanoate (4.180 g, 12.7 mmol, 64% for the two steps) as a colourless oil.

1H NMR (400 MHz, CDCl$_3$, δ): 0.97 (t, 3H, OCH$_2$CH$_3$, $^3J_{H-H}$=7.1 Hz), 1.03 (br s, 3H, NCH$_2$CH$_3$), 1.33 (br s, 3H, NCH$_2$CH$_3$), 3.45 (br s, 4H, NCH$_2$CH$_3$), 3.98 (q, 2H, OCH$_2$CH$_3$, $^3J$=7.1 Hz), 6.87 (Td, 1H, H$_5$, $^3J_{H-F}$=9.7 Hz, $^4J_{H-F}$=6.3 Hz), 7.45 (m, 1H, H$_8$), 7.75 (s, 1H); 19F NMR (376 MHz, CDCl$_3$, δ): −115.6 (dd, F$_2$, $^5J_{F-F}$=15.5 Hz, $^4J_{F-F}$=5.3 Hz), −130.2 (br s, F$_4$); −142.8 (dd, F$_5$, $^3J_{F-F}$=21.5 Hz, $^5J_{F-F}$=15.5 Hz).

Preparation of 1-cyclopropyl-6,7-difluoro-4-oxo-1,4-dihydroquinoline-3-carboxylate ethyl ester

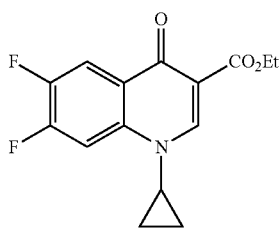 [SMILES: CCOC(=O)c1cn(C2CC2)c2cc(F)c(F)cc2c1=O]

Ethyl α(Z)-[(diethylamino)methylene]-2,4,5-trifluoro-β-oxo-benzenepropanoate (1.977 g, 6.10 mmol) in 1:2 EtOH/Et$_2$O (50 mL) was added to cyclopropylamine (0.98 mL, 10.40 mmol). After 3 h of stirring at room temperature, the reaction mixture was evaporated under reduced pressure. The oily residue was dissolved in DMF (40 mL) and K$_2$CO$_3$ (3.386 g, 24.4 mmol) was then added. After 16 h of stirring at 100° C., cold water (20 mL) was added. The yellow precipitate was filtered and dried affording 1-cyclopropyl-6,7-difluoro-4-oxo-1,4-dihydroquinoline-3-carboxylate ethyl ester (1.336 g, 4.56 mmol, 76%).

$^1$H NMR (400 MHz, CD$_3$CN, δ): 1.07 [m, 2H, CH$_2$(cPr)], 1.26-1.30 [m, 2H, CH$_2$(cPr)], 1.32 [t, 3H, OCH$_2$CH$_3$, $^3J_{H-H}$=7.1 Hz], 3.50 (tt, 1H, CH(cPr), $^3J_{H-H}$=6.9 Hz, $^3J_{H-H}$=3.8 Hz), 4.26 (q, 2H, OCH$_2$CH$_3$, $^3J_{H-H}$=7.1 Hz), 7.95 (dd, 1H, H$_5$, $^3J_{H-F}$=12.1 Hz, $^4J_{H-F}$=6.6 Hz), 7.95 (dd, 1H, H$_8$, $^3J_{H-F}$=10.8 Hz, $^4J_{H-F}$=8.8 Hz), 8.53 (s, 1H, H$_2$). $^{19}$F NMR (376 MHz, CD$_3$CN, δ): −131.1 and −142.4 (2d, 2F, F$_6$ and F$_7$, $^3J_{F-F}$=21.7 Hz); MP=181-182° C.

Preparation of 1-cyclopropyl-6-fluoro-4-oxo-7-(piperazin-1-yl)-1,4-dihydroquinoline-3-carboxylate ethyl ester

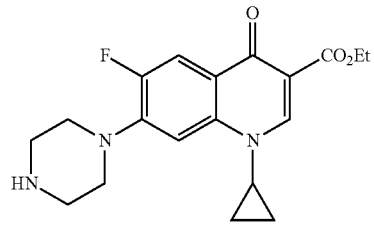 [SMILES: CCOC(=O)c1cn(C2CC2)c2cc(N3CCNCC3)c(F)cc2c1=O]

A solution of piperazine (387 mg, 4.50 mmol) and 1-cyclopropyl-6,7-difluoro-4-oxo-1,4-dihydroquinoline-3-carboxylate ethyl ester (600 mg, 2.05 mmol) in anhydrous CH$_3$CN (10 mL) was refluxed for one week. After evaporation under reduced pressure, the crude residue was partitioned in 1:1 CHCl$_3$/H$_2$O. The organic layer was washed with water, dried over Na$_2$SO$_4$, filtered and evaporated to afford 1-cyclopropyl-6-fluoro-4-oxo-7-(piperazin-1-yl)-1,4-dihydroquinoline-3-carboxylate ethyl ester (657 mg, 1.83 mmol, 89%) as a yellow powder.

1H NMR (400 MHz, CD$_3$CN, δ): 1.04-1.08 (m, 2H, CH$_2$(cPr)), 1.26-1.29 (m, 2H, CH$_2$(cPr)), 1.32 (t, 3H, CH$_3$, $^3J_{H-H}$=7.1 Hz), 2.96 (dd, 4H, H$_{1'}$, H$_{4'}$, $^3J_{H-H}$=3.9 Hz, 5.9 Hz), 3.19 (dd, 4H, H$_{2'}$, H$_{3'}$, $^3J_{H-H}$=3.9 Hz, 5.9 Hz), 3.50 (tt, 1H, CH(cPr), $^3J_{H-H}$=3.7 Hz, 7.0 Hz), 4.25 (q, 2H, CH$_2$, $^3J_{H-H}$=7.1 Hz), 7.42 (d, 1H, H$_8$, $^4J_{H-F}$=7.4 Hz), 7.83 (d, 1H, H$_5$, $^3J_{H-F}$=13.7 Hz), 8.47 (s, 1H, H$_2$). 19F NMR (376 MHz, CD$_3$CN, δ): −125.9 (s, 1F, F$_6$).

Example 2:

Synthesis of the Precursor for the Preparation of Compounds of General Formula III Wherein R$^2$ is a Methoxy Group

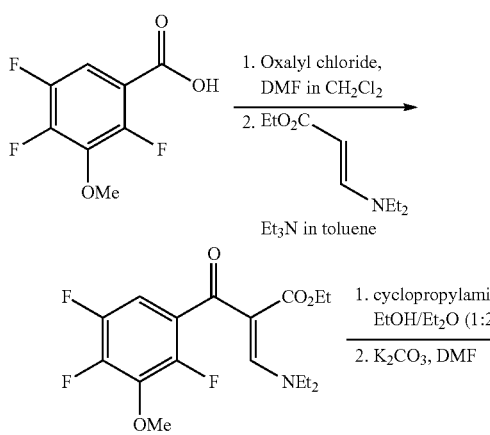

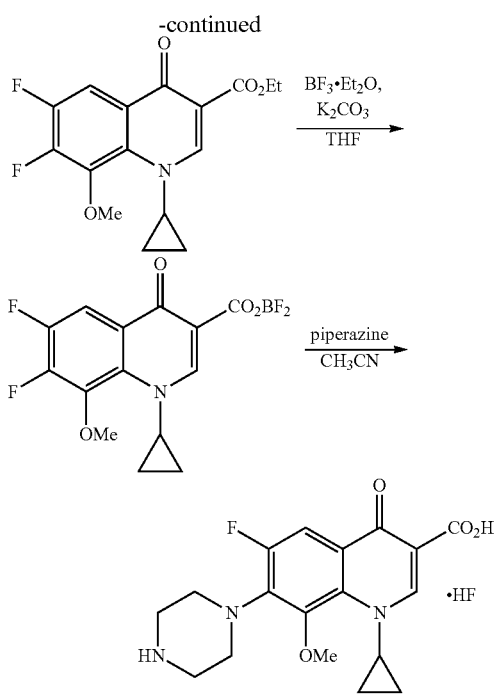

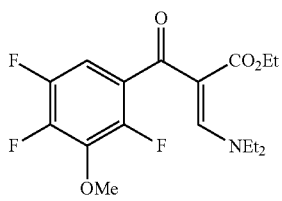

Preparation of Ethyl α(Z)-[(diethylamino)methylene]-2,4,5-trifluoro-3-methoxy-β-oxo-benzenepropanoate An anhydrous $CH_2Cl_2$ solution (30 mL) of 2,4,5-trifluoro-3-methoxy-benzoic acid (1.36 g, 6.60 mmol), oxalyl chloride (0.80 mL, 9.17 mmol) and five drops of DMF was stirred for 24 h at room temperature. The reaction mixture was then subjected to concentrated evaporation under reduced pressure, solubilized in toluene (15 mL) and added dropwise to a toluene solution (15 mL) of triethylamine (3 mL, 16.5 mmol) and ethyl 3-(diethylamino)-2E-propenoate (1.29 g, 7.54 mmol). After 5 h of stirring at 90° C., the cooled reaction mixture was washed with water. The organic layer was dried over $Na_2SO_4$, filtered and evaporated. The crude residue was purified by flash chromatography on silica gel (95:5 to 60:40 hexane/AcOEt) to give Ethyl α(Z)-[(diethylamino)methylene]-2,4,5-trifluoro-3-methoxy-β-oxo-benzenepropanoate (1.88 g, 5.22 mmol, 79% for the two steps) as a colourless oil.

1H NMR (400 MHz, $CDCl_3$, δ): 0.77 (t, 3H, $OCH_2CH_3$, $^3J$=7.1 Hz), 0.84 (br s, 3H, $NCH_2CH_3$), 1.08 (br s, 3H, $NCH_2CH_3$), 3.25 (br s, 4H, $NCH_2CH_3$), 3.76 (q, 2H, $OCH_2CH_3$, $3J$=7.1 Hz), 3.78 (s, 3H, $OCH_3$), 6.87 (ddd, 1H, HAr, $^3J_{H-F}$=10.1 Hz, $^4J_{H-F}$=8.5 Hz, $^4J_{H-F}$=6.0 Hz), 7.53 (s, 1H); 19F NMR (376 MHz, $CDCl_3$, δ): -135.1 (dd, $F_2$, $^5J_{F-F}$=13.8 Hz, $^4J_{F-F}$=7.6 Hz), -141.5 (dd, $F_5$, $^3J_{F-F}$=20.6 Hz, $^5J_{F-F}$=13.7 Hz), -149.2 (br d, $F_4$, $^3J_{F-F}$=6.5 Hz); 13C NMR (100 MHz, $CDCl_3$, δ): 10.8, 14.2, 13.4, 45.0, 53.8, 59.4, 61.5, 101.6, 109.5, 126.2, 137.1, 145.1, 146.6, 149.1, 154.4, 167.3, 184.5.

Preparation of 1-cyclopropyl-6,7-difluoro-8-methoxy-4-oxo-1,4-dihydroquinoline-3-carboxylate ethyl ester

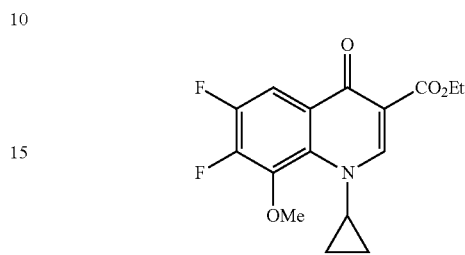

Ethyl α(Z)-[(diethylamino)methylene]-2,4,5-trifluoro-3-methoxy-β-oxo-benzenepropanoate (850 mg, 2.37 mmol) in 1:2 $EtOH/Et_2O$ (20 mL) was added to cyclopropylamine (0.38 mL, 5.48 mmol). After 3 h of stirring at room temperature, the reaction mixture was evaporated under reduced pressure. The oily residue was dissolved in DMF (10 mL) and $K_2CO_3$ (1.32 g, 9.57 mmol) was then added. After 5 h of stirring at 100° C., cold water (5 mL) was added. The yellow precipitate was filtered and dried affording 1-cyclopropyl-6,7-difluoro-8-methoxy-4-oxo-1,4-dihydroquinoline-3-carboxylate ethyl ester (627 mg, 1.94 mmol, 82%).

$^1$H NMR (400 MHz, $CDCl_3$, δ): 1.04 and 1.19 [2m, 4H, $CH_2$(cPr)], 1.37 (t, 3H, $OCH_2CH_3$, $^3J_{H-H}$=7.1 Hz), 3.97 (tt, 1H, CH(cPr), $^3J_{H-H}$=7.5 Hz, $^3J_{H-H}$=3.7 Hz), 4.07 (d, 3H, OCH3, $^5J_{H-H}$=1.9 Hz), 4.35 (q, 2H, $OCH_2CH_3$, $^3J_{H-H}$=7.1 Hz), 7.97 (dd, 1H, $H_5$, $^3J_{H-F}$=10.0 Hz, $^4J_{H-F}$=8.8 Hz), 8.56 (s, 1H, $H_2$). $^{19}$F NMR (376 MHz, $CDCl_3$, δ): -136.9 and -145.1 (2d, 2F, $F_6$ and $F_7$, $^3J_{F-F}$=21.3 Hz); $^{13}$C NMR (100 MHz, $CDCl_3$, δ): 9.2 [$CH_2$(cPr)], 14.5 ($OCH_2CH_3$), 39.8 [CH(cPr)], 61.1 ($OCH_2CH_3$), 62.9 (d, $OCH_3$, $^4J_{C-F}$=7.7 Hz), 108.7 (dd, $C_5$, $^2J_{C-F}$=18.7 Hz, $^3J_{C-F}$=1.1 Hz), 110.1 ($C_3$), 126.1 (dd, Cm, $^3J_{C-F}$=5.9 Hz, $^4J_{C-F}$=1.8 Hz), 131.6 (dd, $C_9$, $^3J_{C-F}$=3.7 Hz, $^4J_{C-F}$=2.2 Hz), 140.4 (d, $C_8$, $^2J_{C-F}$=12.1 Hz), 148.2 (dd, $C_7$, $^1J_{C-F}$=253.7 Hz, $^2J_{C-F}$=15.6 Hz), 149.2 (dd, $C_6$, $J_{C-F}$=251.4 Hz, $^2J_{C-F}$=12.4 Hz), 150.7 ($C_2$), 165.2 [C(O)O], 172.3 ($C_4$). MP=183-184° C.

Preparation of 1-Cyclopropyl-6,7-difluoro-1,4-dihydro-8-methoxy-4-oxo-3-quinoline-carboxylato-O3,O4)difluoro-boron

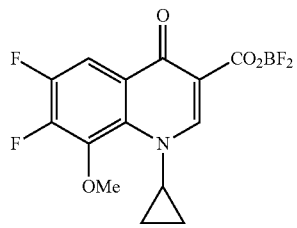

To a solution of 1-cyclopropyl-6,7-difluoro-8-methoxy-4-oxo-1,4-dihydroquinoline-3-carboxylate ethyl ester (621 mg, 1.92 mmol) and $K_2CO_3$ (305 mg, 2.21 mmol) in anhydrous THF (20 mL), $BF_3.Et_2O$ (0.4 mL, 3.18 mmol)

was added dropwise over five minutes. After refluxing for 96 h, the clear reaction mixture was diluted Et$_2$O (40 mL), the resulting mixture was filtered off and washed with Et$_2$O. The crude white solid obtained was solubilized in CH$_3$CN and filtered. The crude solid was solubilized again in CH$_3$CN and filtered. The filtrates were combined and evaporated to afford 1-cyclopropyl-6,7-difluoro-1,4-dihydro-8-methoxy-4-oxo-3-quinoline-carboxylato-O3,O4) difluoro-boron as a white solid (514 mg, 1.50 mmol, 78%).

$^1$H NMR (400 MHz, CD$_3$CN, δ): 1.25-1.37 [m, 4H, 2CH$_2$(cPr)], 4.19 (d, 3H, OCH$_3$, $^5J_{H-F}$=2.4 Hz), 4.48 (tt, 1H, CH(cPr), $^3J_{H-H}$=7.3 Hz, $^3J_{H-H}$=3.8 Hz), 8.17 (dd, 1H, H$_5$, $^3J_{H-F}$=9.8 Hz, $^4J_{H-F}$=8.1 Hz), 9.17 (s, 1H, H$_2$); $^{19}$F NMR (376 MHz, CD$_3$CN, δ): −131.7 and −139.0 (2d, 2F, F$_6$ and F$_7$, $^3J_{F-F}$=19.9 Hz), −144.0 (s, 0.5F, $^{10}$BF$_2$), −144.1 (s, 2.4F, $^{11}$BF$_2$); MS (+ESI) m/z: [M+Na]$^+$ calcd for C$_{14}$H$_{10}$BF$_4$NO$_4$: 343.06; found: 344.2; Mp=221-223° C.

Preparation of 1-cyclopropyl-6-fluoro-8-methoxy-4-oxo-7-(piperazin-1-yl)-1,4-dihydroquinoline-3-carboxylic acid

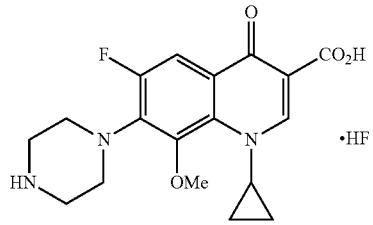

A solution of piperazine (450 mg, 5.2 mmol) and 1-cyclopropyl-6,7-difluoro-1,4-dihydro-8-methoxy-4-oxo-3-quinoline-carboxylato-O3,O4)difluoro-boron (650 mg, 1.89 mmol) in anhydrous CH$_3$CN (25 mL) was refluxed for 96 hours. The solid was washed with CH$_3$CN and Et$_2$O to give 1-cyclopropyl-6-fluoro-8-methoxy-4-oxo-7-(piperazin-1-yl)-1,4-dihydroquinoline-3-carboxylic acid (550 mg, 1.44 mmol, 76%) as a beige solid.

$^1$H NMR (400 MHz, D20/CD$_3$CN:4/1, δ): 0.89 (m, 2H, CH$_2$(cPr)), 1.08 (m, 2H, CH$_2$(cPr)), 3.30 (m, 4H, H$_{1'}$, H$_{4'}$), 3.52 (m, 4H, H$_{2'}$, H$_{3'}$), 3.74 (s, 3H, OCH$_3$), 4.03 (m, 1H, CH(cPr)), 7.68 (d, 1H, H$_5$, =12.1 Hz), 8.59 (s, 1H, H$_2$). $^{19}$F NMR (376 MHz, CD$_3$CN, δ): −121.6 (bs, 1F, F$^-$), −122.2 (s, 1F, F$_6$). MP=191-193° C.

Example 3:

Preparation of Compounds of General Formula III Wherein R$^2$=H

Preparation of 1-cyclopropyl-6-fluoro-4-oxo-7-(4-pentylpiperazin-1-yl)-1,4-dihydroquinoline-3-carboxylic acid (Quin 15)

To a solution of 1-cyclopropyl-6-fluoro-4-oxo-7-(piperazin-1-yl)-1,4-dihydroquinoline-3-carboxylate ethyl ester (63 mg, 0.18 mmol) in dry DMF (18 mL) were added 1-iodopentane (760 mg, 3.8 mmol) and NaHCO$_3$ (150 mg, 1.8 mmol). The reaction mixture was stirred at room temperature for 20 hours and concentrated under reduced pressure. The obtained oily residue was taken up into DCM (40 mL). The organic layer was washed with water (20 mL), dried over anhydrous MgSO$_4$ and concentrated in vacuo to furnish 1-cyclopropyl-6-fluoro-4-oxo-7-(4-pentylpiperazin-1-yl)-1,4-dihydroquinoline-3-carboxylate ethyl ester (65 mg, 86%) as a pale yellow powder. This product was sufficiently pure for the further reaction.

1-cyclopropyl-6-fluoro-4-oxo-7-(4-pentylpiperazin-1-yl)-1,4-dihydroquinoline-3-carboxylate ethyl ester (65 mg, 0.15 mmol) was dissolved in an EtOH/H$_2$O (5/2) mixture (21 mL) and LiOH was then added (30 mg, 1.25 mmol). The reaction mixture was stirred at room temperature for 20 hours and then acidified until pH 1 with HCl$_{aq}$ 3 N. EtOH was removed under reduced pressure and the aqueous layer was extracted with DCM (40 mL). The organic layer was washed with saturated aqueous NaHCO$_3$ solution (20 mL), dried over anhydrous MgSO$_4$ and then concentrated in vacuo to yield 1-cyclopropyl-6-fluoro-4-oxo-7-(4-pentylpiperazin-1-yl)-1,4-dihydroquinoline-3-carboxylic acid (48 mg, 80%) as a white powder.

$^1$H NMR (400 MHz, CDCl$_3$, δ): 14.78 (broad s, 1H, CO$_2$H), 8.73 (s, 1H, H$_2$), 7.90 (d, $^3J_{H-F}$=12.6 Hz, 1H, H$_5$), 7.41 (d, $^4J_{H-F}$=7.0 Hz, 1H, H$_8$), 3.79 (broad s, 4H, H$_{2'}$ and H$_{3'}$), 3.55 (m, 1H, CH(cPr)), 3.54 (broad s, 4H, H$_{1'}$ and H$_{4'}$), 3.02 (m, 2H, NCH$_2$CH$_2$CH$_2$), 1.94 (broad s, 2H, NCH$_2$CH$_2$CH$_2$), 1.47-1.37 (m, 6H, CH$_2$(cPr), NCH$_2$CH$_2$CH$_2$CH$_2$), 1.28-1.19 (m, 2H, CH$_2$(cPr)), 0.94 (t, $^3J_{H-H}$=6.7 Hz, 3H, CH$_3$). $^{19}$F NMR (376 MHz, CDCl$_3$, δ): −121.9 (s, F$_6$). $^{13}$C NMR (100 MHz, CDCl$_3$, δ): 177.1 (d, J=2.6 Hz, C$_4$), 166.7 (s, CO$_2$H), 153.5 (d, J=250.6 Hz, C$_6$), 147.9 (s, C$_2$), 144.3 (d, J=10.4 Hz, C$_7$), 139.0 (s, C$_9$), 121.0 (d, J=8.0 Hz, C$_{10}$), 112.6 (d, J=23.1 Hz, C$_5$), 108.4 (s, C$_3$), 106.1 (d, J=2.3 Hz, C$_8$), 58.0 (s, NCH$_2$CH$_2$CH$_2$), 51.9 (s, C$_{1'}$ and C$_{4'}$), 46.9 (s, C$_{2'}$ and C$_{3'}$), 35.6 (s, CH(cPr)), 29.0 (s, CH$_2$), 23.6 (s, CH$_2$), 22.3 (s, CH$_2$), 13.9 (s, CH$_3$), 8.5 (s, 2CH$_2$(cPr)). IR (neat): v=3433, 2956, 2933, 2872, 1729, 1630, 1505, 1471, 1390, 1337, 1302, 1266, 1099, 979, 944, 892, 831, 805, 733 cm$^{-1}$; HRMS (+ESI) m/z: [M+Na]$^+$ calcd for C$_{22}$H$_{29}$FN$_3$O$_3$: 402.2194, found: 402.2192.

The compounds of reference Quin 16, Quin 9, and Quin 10 were prepared in the same manner than the compound of reference Quin 15, using corresponding starting materials.

Preparation of 1-cyclopropyl-6-fluoro-7-(4-octylpiperazin-1-yl)-4-oxo-1,4-dihydroquinoline-3-carboxylic acid (Quin 16)

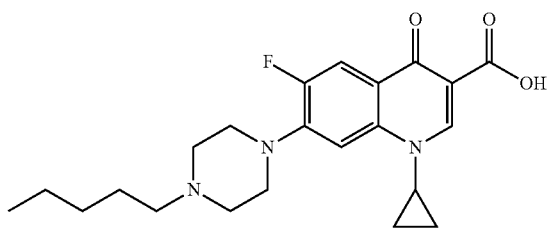 [SMILES: CCCCCN1CCN(c2cc3c(cc2F)c(=O)c(C(=O)O)cn3C2CC2)CC1]

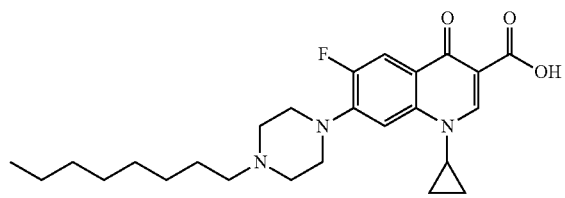 [SMILES: CCCCCCCCN1CCN(c2cc3c(cc2F)c(=O)c(C(=O)O)cn3C2CC2)CC1]

1-cyclopropyl-6-fluoro-7-(4-octylpiperazin-1-yl)-4-oxo-1,4-dihydroquinoline-3-carboxylate ethyl ester was synthesized (70 mg, 87%, pale yellow powder) according to reference Quin 15, starting from 1-cyclopropyl-6-fluoro-4-oxo-7-(piperazin-1-yl)-1,4-dihydroquinoline-3-carboxylate ethyl ester (63 mg, 0.18 mmol), 1-iodooctane (133 mg, 0.55 mmol) and NaHCO$_3$ (80 mg, 0.95 mmol) in dry DMF (15 mL). This product was sufficiently pure for the further reaction.

1-cyclopropyl-6-fluoro-7-(4-octylpiperazin-1-yl)-4-oxo-1,4-dihydroquinoline-3-carboxylic acid (45 mg, 68%, white powder) was obtained according to Quin 15, starting from 1-cyclopropyl-6-fluoro-7-(4-octylpiperazin-1-yl)-4-oxo-1,4-dihydroquinoline-3-carboxylate ethyl ester (70 mg, 0.15 mmol) and LiOH (40 mg, 1.67 mmol) in an EtOH/H$_2$O (5/2) mixture (21 mL).

$^1$H NMR (400 MHz, CDCl$_3$, δ): 15.02 (broad s, 1H, CO$_2$H), 8.71 (s, 1H, H$_2$), 7.94 (d, $^3J_{H-F}$=13.1 Hz, 1H, H$_5$), 7.34 (d, $^4J_{H-F}$=7.1 Hz, 1H, H$_8$), 3.55 (broad s, 1H, CH(cPr)), 3.36 (broad s, 4H, H$_{2'}$ and H$_{3'}$), 2.67 (broad s, 4H, H$_{1'}$ and H$_{4'}$), 2.42 (m, 2H, NCH$_2$CH$_2$CH$_2$), 1.58-1.48 (m, 2H, NCH$_2$CH$_2$CH$_2$), 1.42-1.21 (m, 12H, CH$_2$(cPr), 5CH$_2$), 1.15-1.21 (m, 2H, CH$_2$(cPr)), 0.87 (t, $^3J_{H-H}$=6.8 Hz, 3H, CH$_3$). $^{19}$F NMR (376 MHz, CDCl$_3$, δ): −120.7 (s, F$_6$). $^{13}$C NMR (100 MHz, CDCl$_3$, δ): 177.2 (d, J=2.5 Hz, C$_4$), 167.1 (s, CO$_2$H), 153.8 (d, J=251.6 Hz, C$_6$), 147.4 (s, C$_2$), 146.1 (d, J=10.3 Hz, C$_7$), 139.2 (s, C$_9$), 119.8 (d, J=7.9 Hz, C$_{10}$), 112.4 (d, J=23.5 Hz, C$_5$), 108.2 (s, C$_3$), 104.9 (d, J=3.3 Hz, C$_8$), 58.8 (s, NCH$_2$CH$_2$CH$_2$), 53.0 (s, C$_{1'}$ and C$_{4'}$), 50.0 (s, C$_{2'}$ and C$_{3'}$), 35.4 (s, CH(cPr)), 31.9 (s, CH$_2$), 29.6 (s, CH$_2$), 29.4 (s, CH$_2$), 27.6 (s, CH$_2$), 26.9 (s, CH$_2$), 22.8 (s, CH$_2$), 14.2 (s, CH$_3$), 8.3 (s, 2CH$_2$(cPr)). IR (neat): v=2926, 2854, 2816, 2778, 1725, 1626, 1611, 1544, 1494, 1464, 1452, 1378, 1344, 1299, 1254, 1223, 1185, 1143, 1128, 1109, 1094, 1043, 1027, 1009, 991, 945, 890, 859, 833, 805, 778, 747, 706 cm$^{-1}$; HRMS (+ESI) m/z: [M+H]$^+$ calcd for C$_{25}$H$_{34}$FN$_3$O$_3$: 444.2663, found: 444.2668.

Preparation of 1-cyclopropyl-7-(4-decylpiperazin-1-yl)-6-fluoro-4-oxo-1,4-dihydroquinoline-3-carboxylic acid (Quin 9)

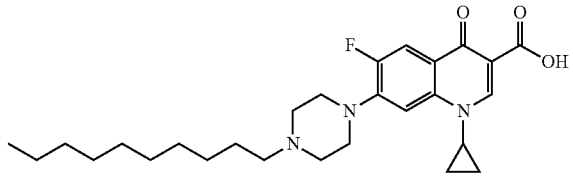 [SMILES: CCCCCCCCCCN1CCN(c2cc3c(cc2F)c(=O)c(C(=O)O)cn3C2CC2)CC1]

1-cyclopropyl-7-(4-decylpiperazin-1-yl)-6-fluoro-4-oxo-1,4-dihydroquinoline-3-carboxylate ethyl ester was synthesized (117 mg, 72%, beige powder) according to reference Quin 15, starting from 1-cyclopropyl-6-fluoro-4-oxo-7-(piperazin-1-yl)-1,4-dihydroquinoline-3-carboxylate ethyl ester (117 mg, 0.33 mmol), 1-iododecane (0.10 mL, 0.49 mmol) and NaHCO$_3$ (82 mg, 0.98 mmol). This product was sufficiently pure for the further reaction.

1-cyclopropyl-7-(4-decylpiperazin-1-yl)-6-fluoro-4-oxo-1,4-dihydroquinoline-3-carboxylic acid (52 mg, 92%, white powder) was obtained according to Quin 15, starting from 1-cyclopropyl-6-fluoro-7-(4-decylpiperazin-1-yl)-4-oxo-1,4-dihydroquinoline-3-carboxylate ethyl ester (60 mg, 0.12 mmol) and LiOH.H$_2$O (55 mg, 1.32 mmol) in 39 ml of 4:1 MeOH/H$_2$O.

$^1$H NMR (400 MHz, CDCl$_3$, δ): 15.03 (broad s, 1H, CO$_2$H), 8.78 (s, 1H, H$_2$), 8.03 (d, $^3J_{H-F}$=13.0 Hz, 1H, H$_5$), 7.36 (d, $^4J_{H-F}$=7.1 Hz, 1H, H$_8$), 3.53 (broad s, 1H, CH(cPr)), 3.38 (broad s, 4H, H$_{2'}$ and H$_{3'}$), 2.71 (broad s, 4H, H$_{1'}$ and H$_{4'}$), 2.45 (m, 2H, NCH$_2$CH$_2$CH$_2$), 1.60-1.49 (m, 2H, NCH$_2$CH$_2$CH$_2$), 1.42-1.16 (m, 18H, 2CH$_2$(cPr), 7CH$_2$), 0.88 (t, $^3J_{H-H}$=6.9 Hz, 3H, CH$_3$). $^{19}$F NMR (376 MHz, CDCl$_3$, δ): s, 1F, F$_6$). HRMS (+ESI) m/z: calcd for C$_{27}$H$_{39}$FN$_3$O$_3$: 472.2975; found 472.2965 [M+H]$^+$ IR (neat): 2928 (acide), 2853 (alkyl), 1625 (cetone), 1488 (C=C), 1413 (C=C), 1306 (C—N, C—C, C—O), 1254 (C—N, C—C, C—O). MP=209° C.

Preparation of 1-cyclopropyl-6-fluoro-7-(4-hexadecylpiperazin-1-yl)-4-oxo-1,4-dihydroquinoline-3-carboxylic acid (Quin 10)

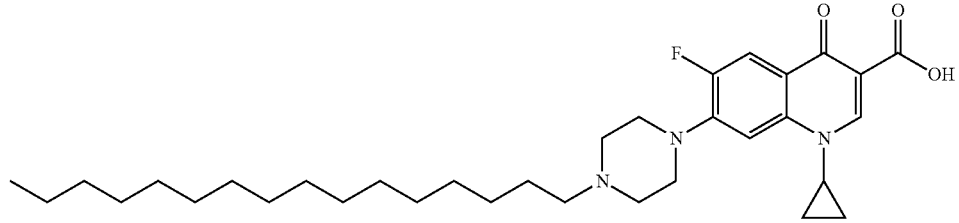 [SMILES: CCCCCCCCCCCCCCCCN1CCN(c2cc3c(cc2F)c(=O)c(C(=O)O)cn3C2CC2)CC1]

1-cyclopropyl-6-fluoro-7-(4-hexadecylpiperazin-1-yl)-4-oxo-1,4-dihydroquinoline-3-carboxylate ethyl ester was synthesized (146 mg, 90%, white solid) according to reference Quin 15, starting from 1-cyclopropyl-6-fluoro-4-oxo-7-(piperazin-1-yl)-1,4-dihydroquinoline-3-carboxylate ethyl ester (100 mg, 0.28 mmol), 1-iodohexadecane (147 mg, 0.42 mmol) and NaHCO$_3$ (70 mg, 0.84 mmol). This product was sufficiently pure for the further reaction.

1-cyclopropyl-6-fluoro-7-(4-hexadecylpiperazin-1-yl)-4-oxo-1,4-dihydroquinoline-3-carboxylate ethyl ester (60 mg, 0.1 mmol) and LiOH.H$_2$O (47 mg, 1.10 mmol) in 34 ml of 4:1MeOH/H$_2$O. The mixture was stirred at room temperature for 24 h and kept stirring for another 22 h at reflux. After acidification with glacial AcOH to pH 5-6, the solvent was evaporated to dryness, and a small amount of water was added. The suspension was filtered, and the solid was dried in vacuo to give the desired compound as a yellow powder (35 mg, 0.06 mmol, 61%).

$^1$H NMR (400 MHz, CDCl$_3$, δ): 15.03 (broad s, 1H, CO$_2$H), 8.78 (s, 1H, H$_2$), 8.03 (d, $^3J_{H-F}$=13.0 Hz, 1H, H$_5$), 7.36 (d, $^4J_{H-F}$=6.2 Hz, 1H, H$_8$), 3.54 (broad s, 1H, CH(cPr)), 3.36 (broad s, 4H, H$_{2'}$ and H$_{3'}$), 2.67 (broad s, 4H, H$_{1'}$ and H$_{4'}$), 2.42 (dd, $^3J_{H-H}$=7.8, 7.3 Hz, 2H, NCH$_2$CH$_2$CH$_2$), 1.60-1.49 (m, 2H, NCH$_2$CH$_2$CH$_2$), 1.42-1.15 (m, 30H, 2CH$_2$(cPr), 13CH$_2$), 0.88 (t, $^3J_{H-H}$=6.5 Hz, 3H, CH$_3$). $^{19}$F NMR (376 MHz, CDCl$_3$, δ): δ-120.7 (s, 1F, F$_6$). $^{13}$C NMR (100 MHz, CDCl$_3$, δ): δ 8.3 (s, CH$_2$(cPr)), 14.2 (s, CH$_3$), 22.8 (s, CH$_2$), 26.9 (s, NCH$_2$CH$_2$), 27.7, 29.5, 29.6, 29.7, 29.8, 32.0 (s, CH$_2$), 49.9 (d, C$_{2'}$ and C$_{3'}$, $^4J_{C-F}$=4.4 Hz), 50.9 (s, CH(cPr)), 52.9 (s, C$_{1'}$ and C$_{4'}$), 58.7 (s, NCH$_2$CH$_2$), 104.8 (d, C$_8$, $^3J_{C-F}$=2.9 Hz), 108.2 (s, C$_3$), 112.4 (d, C$_5$, $^2J_{C-F}$=23.3 Hz), 119.8 (d, C$_{10}$, $^3J_{C-F}$=6.3 Hz), 139.2 (s, C$_9$), 146.1 (d, C$_7$, $^2J_{C-F}$=11.2 Hz), 147.5 (s, C$_2$), 153.3 (d, C$_6$, $^1J_{C-F}$=249.7 Hz), 167.2 (s, C$_5$), 177.2 (s, C$_4$). HRMS (+ESI) m/z: calcd for C$_{33}$H$_{51}$FN$_3$O$_3$: 556.3914; found: 556.3891 [M+H]$^+$ IR (neat): 2916 (acide), 2850 (alkyl), 1742 (acide), 1626 (cetone), 1501 (C=C), 1464 (C=C), 1335 (C—N, C—C, C—O), 1254 (C—N, C—C, C—O), 1131 (C—N, C—C, C—O), 1029 (C—F). MP=150° C.

Example 4:

Preparation of Compounds of General Formula III Wherein R$^2$=OMe

Preparation of 1-cyclopropyl-6-fluoro-8-methoxy-4-oxo-7-(4-pentylpiperazin-1-yl)-1,4-dihydroquinoline-3-carboxylic acid (Quin 17)

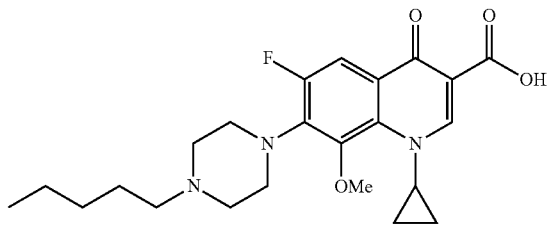 [SMILES: CCCCCN1CCN(c2c(F)cc3c(=O)c(C(=O)O)cn(C4CC4)c3c2OC)CC1]

To a suspension of 1-cyclopropyl-6-fluoro-8-methoxy-4-oxo-7-(piperazin-1-yl)-1,4-dihydroquinoline-3-carboxylic acid (65 mg, 0.17 mmol) in dry DMF (18 mL), were added 1-iodopentane (152 mg, 0.77 mmol) and NaHCO$_3$ (200 mg, 2.4 mmol). The reaction mixture was stirred at 40° C. for 40 hours and then concentrated under reduced pressure. The residue was taken up in DCM (40 mL) and the organic layer was washed with water (30 mL) and dried over anhydrous MgSO$_4$ to give a mixture of 1-cyclopropyl-6-fluoro-8-methoxy-4-oxo-7-(4-pentylpiperazin-1-yl)-1,4-dihydroquinoline-3-carboxylic acid and 1-cyclopropyl-6-fluoro-8-methoxy-4-oxo-7-(4-pentylpiperazin-1-yl)-1,4-dihydroquinoline-3-carboxylic pentyl ester (150 mg).

The latter mixture was dissolved in an EtOH/H$_2$O (5/2) mixture (21 mL) and LiOH (40 mg, 1.67 mmol) was then added. The reaction mixture was stirred overnight at room temperature and then acidified with HCl$_{aq}$ 1 N until pH 3. Ethanol was removed under reduced pressure and the aqueous layer was extracted with DCM (40 mL). The organic layer was washed with saturated aqueous NaHCO$_3$ solution (20 mL), dried over anhydrous MgSO$_4$ and concentrated in vacuo. The crude solid obtained was washed with Et$_2$O (3×5 mL) to yield 1-cyclopropyl-6-fluoro-8-methoxy-4-oxo-7-(4-pentylpiperazin-1-yl)-1,4-dihydroquinoline-3-carboxylic acid (25 mg, 34% over 2 steps) as a yellow powder.

$^1$H NMR (400 MHz, CD$_2$Cl$_2$, δ): 14.83 (broad s, 1H, CO$_2$H), 8.78 (s, 1H, H$_2$), 7.82 (d, $^3J_{H-F}$=12.4 Hz, 1H, H$_5$), 4.04 (m, 1H, CH(cPr)), 3.76 (s, 3H, OCH$_3$), 3.43 (broad s, 4H, H$_{2'}$ and H$_{3'}$), 2.58 (broad s, 4H, H$_{1'}$ and H$_{4'}$), 2.39 (m, 2H, NCH$_2$CH$_2$CH$_2$), 1.52 (m, 2H, NCH$_2$CH$_2$CH$_2$), 1.42-1.24 (m, 4H, NCH$_2$CH$_2$CH$_2$CH$_2$), 1.20 (q, J=6.8 Hz, 2H, CH$_2$(cPr)), 1.01-0.95 (m, 2H, CH$_2$(cPr)), 0.92 (t, $^3J_{H-H}$=6.9 Hz, 3H, CH$_3$). $^{19}$F NMR (376 MHz, CD$_2$Cl$_2$, δ): −120.1 (s, F$_6$). $^{13}$C NMR (75 MHz, CD$_2$Cl$_2$, δ): 177.5 (d, J=2.9 Hz, C$_4$), 166.9 (s, CO$_2$H), 156.7 (d, J=250.9 Hz, C$_6$), 150.3 (s, C$_2$), 145.9 (d, J=5.8 Hz, C$_8$), 140.1 (d, J=11.6 Hz, C$_7$), 134.6 (s, C$_9$), 121.9 (d, J=9.3 Hz, C$_{10}$), 108.0 (s, C$_3$), 107.9 (d, J=23.3 Hz, C$_5$), 62.8 (s, OCH$_3$), 59.2 (s, NCH$_2$CH$_2$CH$_2$), 54.3 (s, C$_{1'}$ and C$_{4'}$), 51.2 (d, J=4.6 Hz, C$_{2'}$ and C$_{3'}$), 41.0 (s, CH(cPr)), 30.1 (s, CH$_2$), 26.9 (s, NCH$_2$CH$_2$CH$_2$), 23.1 (s, CH$_2$), 14.3 (s, CH$_3$), 9.8 (s, 2CH$_2$(cPr)). IR (neat): v=3081, 2954, 2931, 2857, 2810, 2771, 1729, 1665, 1616, 1580, 1534, 1506, 1440, 1372, 1314, 1277, 1238, 1206, 1187, 1148, 1128, 1114, 1089, 1057, 1039, 1001, 958, 936, 888, 851, 821, 807, 776, 732, 709 cm$^{-1}$; HRMS (+ESI) m/z: [M+H]$^+$ calcd for C$_{23}$H$_{30}$FN$_3$O$_4$: 432.2299, found: 432.2311.

The compounds of reference Quin 18, Quin 19, and Quin 20, and compounds 15, 17, 19, 20 and 22, were prepared in the same manner than compound of reference Quin 17, using corresponding starting materials.

Preparation of 1-cyclopropyl-6-fluoro-8-methoxy-7-(4-heptylpiperazin-1-yl)-4-oxo-1,4-dihydroquinoline-3-carboxylic acid (compound 15)

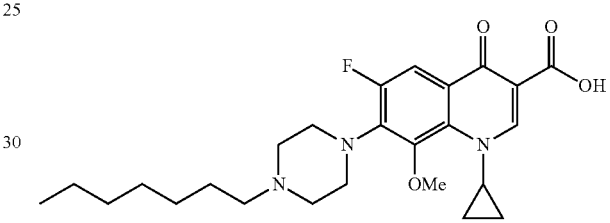

A mixture of 1-cyclopropyl-6-fluoro-8-methoxy-7-(4-heptylpiperazin-1-yl)-4-oxo-1,4-dihydroquinoline-3-carboxylic acid and 1-cyclopropyl-6-fluoro-8-methoxy-7-(4-heptylpiperazin-1-yl)-4-oxo-1,4-dihydroquinoline-3-carboxylate heptyl ester were obtained according to reference Quin 17, starting from 1-cyclopropyl-6-fluoro-8-methoxy-4-oxo-7-(piperazin-1-yl)-1,4-dihydroquinoline-3-carboxylic acid (2.370 g, 6.21 mmol), 1-iodoheptane (4.75 g, 21.2 mmol) and NaHCO$_3$ (3.69 g, 43.9 mmol) in dry DMF (450 mL). This product was sufficiently pure for the further reaction.

1-cyclopropyl-6-fluoro-8-methoxy-7-(4-heptylpiperazin-1-yl)-4-oxo-1,4-dihydroquinoline-3-carboxylic acid (1.03 g, 2.17 mmol, 35% over two steps, yellow powder) was obtained according to reference Quin 17, starting from the later mixture and LiOH (580 mg, 24.2 mmol) in an EtOH/H$_2$O (5/2) mixture (400 mL).

$^1$H NMR (400 MHz, CD$_2$Cl$_2$, δ): 14.77 (broad s, 1H, CO$_2$H), 8.77 (s, 1H, H$_2$), 7.80 (d, $^3J_{H-F}$=12.4 Hz, 1H, H$_5$), 4.04 (m, 1H, CH(cPr)), 3.77 (s, 3H, OCH$_3$), 3.43 (broad s, 4H, H$_{2'}$ and H$_{3'}$), 2.58 (broad s, 4H, H$_{1'}$ and H$_{4'}$), 2.39 (m, 2H, NCH$_2$CH$_2$CH$_2$), 1.50 (m, 2H, NCH$_2$CH$_2$CH$_2$), 1.42-1.24 (m, 8H, CH$_2$), 1.20 (q, J=6.9 Hz, 2H, CH$_2$(cPr)), 1.02-0.95 (m, 2H, CH$_2$(cPr)), 0.89 (t, $^3J_{H-H}$=6.8 Hz, 3H, CH$_3$). $^{13}$C NMR (100 MHz, CD$_2$Cl$_2$, δ): 177.1 (d, J=3.1 Hz, C$_4$), 166.9 (s, CO$_2$H), 157.8 (d, J=250.8 Hz, C$_6$), 154.5 (s, C$_2$), 145.4 (d, J=5.8 Hz, C$_8$), 139.5 (d, J=11.7 Hz, C$_7$), 134.1 (s, C$_9$), 121.9 (d, J=9.2 Hz, C$_{10}$), 108.4 (s, C$_3$), 107.9 (d, J=23.3 Hz, C$_5$), 62.7 (s, OCH$_3$), 59.1 (s, NCH$_2$CH$_2$CH$_2$), 53.9 (s, C$_{1'}$ and C$_{4'}$), 50.5 (d, J=4.6 Hz, C$_{2'}$ and C$_{3'}$), 40.6 (s, CH(cPr)), 31.9 (s, CH$_2$), 29.3 (s, CH$_2$), 29.0 (s, CH$_2$), 27.6 (s, CH$_2$), 27.2 (s, CH$_2$), 26.7 (s, CH$_2$), 22.7 (s, CH$_2$), 14.2 (s, CH$_3$), 9.7 (s, 2CH$_2$(cPr)). MP=157.2° C. Elemental Analysis: C=64.62%, H=7.52%, N=8.83%, calcd C=65.14%, H=7.47%, N=9.12%.

Preparation of 1-cyclopropyl-6-fluoro-8-methoxy-7-(4-octylpiperazin-1-yl)-4-oxo-1,4-dihydroquinoline-3-carboxylic acid (Quin 18)

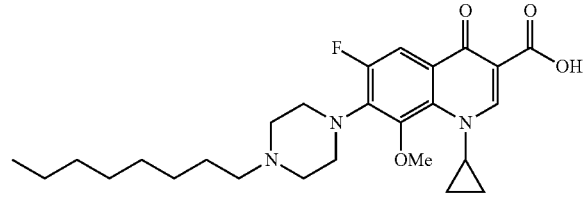 [SMILES: CCCCCCCCN1CCN(c2c(F)cc3c(=O)c(C(=O)O)cn(C4CC4)c3c2OC)CC1]

A mixture of 1-cyclopropyl-6-fluoro-8-methoxy-7-(4-octylpiperazin-1-yl)-4-oxo-1,4-dihydroquinoline-3-carboxylic acid and 1-cyclopropyl-6-fluoro-8-methoxy-7-(4-octylpiperazin-1-yl)-4-oxo-1,4-dihydroquinoline-3-carboxylate octyl ester (80 mg) were obtained according to reference Quin 17, starting from 1-cyclopropyl-6-fluoro-8-methoxy-4-oxo-7-(piperazin-1-yl)-1,4-dihydroquinoline-3-carboxylic acid (75 mg, 0.20 mmol), 1-iodooctane (133 mg, 0.55 mmol) and NaHCO$_3$ (100 mg, 1.20 mmol) in dry DMF (18 mL). This product was sufficiently pure for the further reaction.

1-cyclopropyl-6-fluoro-8-methoxy-7-(4-octylpiperazin-1-yl)-4-oxo-1,4-dihydroquinoline-3-carboxylic acid (30 mg, 32% over two steps, yellow powder) was obtained according to reference Quin 17, starting from the later mixture (80 mg) and LiOH (40 mg, 1.67 mmol) in an EtOH/H$_2$O (5/2) mixture (21 mL).

$^1$H NMR (400 MHz, CD$_2$Cl$_2$, δ): 14.77 (broad s, 1H, CO$_2$H), 8.77 (s, 1H, H$_2$), 7.80 (d, $^3J_{H-F}$=12.4 Hz, 1H, H$_5$), 4.04 (m, 1H, CH(cPr)), 3.77 (s, 3H, OCH$_3$), 3.43 (broad s, 4H, H$_2$, and H$_3$,), 2.58 (broad s, 4H, H$_1$, and H$_4$,), 2.39 (m, 2H, NCH$_2$CH$_2$CH$_2$), 1.50 (m, 2H, NCH$_2$CH$_2$CH$_2$), 1.42-1.24 (m, 10H, CH$_2$), 1.20 (q, J=6.9 Hz, 2H, CH$_2$(cPr)), 1.02-0.95 (m, 2H, CH$_2$(cPr)), 0.89 (t, $^3J_{H-H}$=6.8 Hz, 3H, CH$_3$). $^{19}$F NMR (376 MHz, CD$_2$Cl$_2$, δ): −120.1 (s, F$_6$). $^{13}$C NMR (100 MHz, CD$_2$Cl$_2$, δ): 177.5 (d, J=3.1 Hz, C$_4$), 166.8 (s, CO$_2$H), 156.7 (d, J=250.8 Hz, C$_6$), 150.3 (s, C$_2$), 145.9 (d, J=5.8 Hz, C$_8$), 140.1 (d, J=11.7 Hz, C$_7$), 134.6 (s, C$_9$), 121.9 (d, J=9.2 Hz, C$_{10}$), 108.0 (s, C$_3$), 107.9 (d, J=23.3 Hz, C$_5$), 62.8 (s, OCH$_3$), 59.3 (s, NCH$_2$CH$_2$CH$_2$), 54.3 (s, C$_1$, and C$_4$,), 51.2 (d, J=4.6 Hz, C$_2$, and C$_3$,), 41.0 (s, CH(cPr)), 32.3 (s, CH$_2$), 30.0 (s, CH$_2$), 29.7 (s, CH$_2$), 27.9 (s, CH$_2$), 27.2 (s, CH$_2$), 23.1 (s, CH$_2$), 14.3 (s, CH$_3$), 9.8 (s, 2CH$_2$(cPr)). IR (neat): v=3084, 2926, 2853, 2809, 2770, 1728, 1617, 1601, 1554, 1539, 1505, 1436, 1383, 1376, 1312, 1280, 1238, 1204, 1187, 1144, 1128, 1115, 1091, 1055, 1040, 1008, 993, 957, 934, 887, 831, 821, 805, 730, 710 cm$^{-1}$; HRMS (+ESI) m/z: [M+H]$^+$ calcd for C$_{26}$H$_{36}$FN$_3$O$_4$: 474.2769, found: 474.2765. Elemental Analysis: C=66.11%, H=7.78%, N=8.82%, calcd C=65.94%, H=7.66%, N=8.87%.

Preparation of 1-cyclopropyl-6-fluoro-8-methoxy-7-(4-nonylpiperazin-1-yl)-4-oxo-1,4-dihydroquinoline-3-carboxylic acid (compound 17)

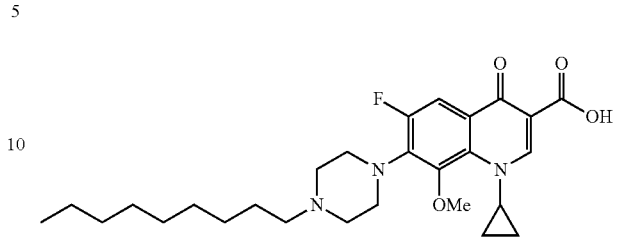

A mixture of 1-cyclopropyl-6-fluoro-8-methoxy-7-(4-nonylpiperazin-1-yl)-4-oxo-1,4-dihydroquinoline-3-carboxylic acid and 1-cyclopropyl-6-fluoro-8-methoxy-7-(4-nonylpiperazin-1-yl)-4-oxo-1,4-dihydroquinoline-3-carboxylate nonyl ester were obtained according to reference Quin 17, starting from 1-cyclopropyl-6-fluoro-8-methoxy-4-oxo-7-(piperazin-1-yl)-1,4-dihydroquinoline-3-carboxylic acid (2.04 g, 5.35 mmol), 1-iodononane (4.45 g, 17.5 mmol) and NaHCO$_3$ (3.04 g, 36.2 mmol) in dry DMF (450 mL). This product was sufficiently pure for the further reaction.

1-cyclopropyl-6-fluoro-8-methoxy-7-(4-nonylpiperazin-1-yl)-4-oxo-1,4-dihydroquinoline-3-carboxylic acid (1.02 g, 2.03 mmol, 38% over two steps, yellow powder) was obtained according to reference Quin 17, starting from the later mixture and LiOH (580 mg, 24.2 mmol) in an EtOH/H$_2$O (5/2) mixture (400 mL).

$^1$H NMR (400 MHz, CD$_2$Cl$_2$, δ): 14.77 (broad s, 1H, CO$_2$H), 8.77 (s, 1H, H$_2$), 7.80 (d, $^3J_{H-F}$=12.4 Hz, 1H, H$_5$), 4.04 (m, 1H, CH(cPr)), 3.77 (s, 3H, OCH$_3$), 3.43 (broad s, 4H, H$_2$, and H$_3$,), 2.58 (broad s, 4H, H$_1$, and H$_4$,), 2.39 (m, 2H, NCH$_2$CH$_2$CH$_2$), 1.50 (m, 2H, NCH$_2$CH$_2$CH$_2$), 1.42-1.24 (m, 12H, CH$_2$), 1.20 (q, J=6.9 Hz, 2H, CH$_2$(cPr)), 1.02-0.95 (m, 2H, CH$_2$(cPr)), 0.89 (t, $^3J_{H-H}$=6.8 Hz, 3H, CH$_3$). $^{13}$C NMR (100 MHz, CD$_2$Cl$_2$, δ): 177.1 (d, J=3.1 Hz, C$_4$), 166.9 (s, CO$_2$H), 157.9 (d, J=250.8 Hz, C$_6$), 154.5 (s, C$_2$), 145.3 (d, J=5.8 Hz, C$_8$), 139.7 (d, J=11.7 Hz, C$_7$), 134.0 (s, C$_9$), 121.6 (d, J=9.2 Hz, C$_{10}$), 108.2 (s, C$_3$), 107.9 (d, J=23.3 Hz, C$_5$), 62.6 (s, OCH$_3$), 59.1 (s, NCH$_2$CH$_2$CH$_2$), 54.0 (s, C$_1$, and C$_4$,), 50.8 (d, J=4.6 Hz, C$_2$, and C$_3$,), 40.6 (s, CH(cPr)), 32.0 (s, CH$_2$), 29.7 (s, CH$_2$), 29.6 (s, CH$_2$), 29.4 (s, CH$_2$), 27.7 (s, CH$_2$), 26.9 (s, CH$_2$), 25.5 (s, CH$_2$), 22.8 (s, CH$_2$), 14.2 (s, CH$_3$), 9.7 (s, 2CH$_2$(cPr)). MP=144.4° C. Elemental Analysis: C=66.36%, H=7.86%, N=8.50%, calcd C=66.51%, H=7.85%, N=8.62%.

Preparation of 1-cyclopropyl-7-(4-decylpiperazin-1-yl)-6-fluoro-8-methoxy-4-oxo-1,4-dihydroquinoline-3-carboxylic acid (Quin 19)

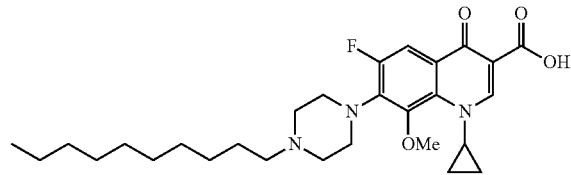 [SMILES: CCCCCCCCCCN1CCN(c2c(F)cc3c(=O)c(C(=O)O)cn(C4CC4)c3c2OC)CC1]

A mixture of 1-cyclopropyl-7-(4-decylpiperazin-1-yl)-6-fluoro-8-methoxy-4-oxo-1,4-dihydroquinoline-3-carboxylic acid and 1-cyclopropyl-6-fluoro-8-methoxy-4-oxo-7-(4-decylpiperazin-1-yl)-1,4-dihydroquinoline-3-carboxylate decyl ester (90 mg) were obtained according to reference Quin 17, starting from 1-cyclopropyl-6-fluoro-8-methoxy-4-oxo-7-(piperazin-1-yl)-1,4-dihydroquinoline-3-carboxylic acid (80 mg, 0.21 mmol), 1-iododecane (163 mg, 0.61 mmol) and $NaHCO_3$ (120 mg, 1.40 mmol) in dry DMF (20 mL). This product was sufficiently pure for the further reaction.

1-cyclopropyl-7-(4-decylpiperazin-1-yl)-6-fluoro-8-methoxy-4-oxo-1,4-dihydroquinoline-3-carboxylic acid (30 mg, 29% over two steps, white solid) was obtained according to reference Quin 17, starting from the later mixture (90 mg) and LiOH (40 mg, 1.67 mmol) in an $EtOH/H_2O$ (5/2) mixture (21 mL).

$^1H$ NMR (400 MHz, $CD_2Cl_2$, δ): 14.78 (broad s, 1H, $CO_2H$), 8.78 (s, 1H, $H_2$), 7.82 (d, $^3J_{H-F}$=12.4 Hz, 1H, $H_5$), 4.04 (m, 1H, CH(cPr)), 3.76 (s, 3H, $OCH_3$), 3.43 (broad s, 4H, $H_{2'}$ and $H_{3'}$), 2.57 (broad s, 4H, $H_{1'}$ and $H_{4'}$), 2.39 (m, 2H, $NCH_2CH_2CH_2$), 1.51 (m, 2H, $NCH_2CH_2CH_2$), 1.37-1.24 (m, 14H, $CH_2$), 1.20 (m, 2H, $CH_2$(cPr)), 1.02-0.95 (m, 2H, $CH_2$(cPr)), 0.89 (t, $^3J_{H-H}$=6.7 Hz, 3H, $CH_3$). $^{19}F$ NMR (376 MHz, $CD_2Cl_2$, δ): −120.1 (s, $F_6$). $^{13}C$ NMR (100 MHz, $CD_2Cl_2$, δ): 177.5 (d, J=3.1 Hz, $C_4$), 166.9 (s, $CO_2H$), 156.7 (d, J=250.9 Hz, $C_6$), 150.3 (s, $C_2$), 145.9 (d, J=5.8 Hz, $C_8$), 140.1 (d, J=11.8 Hz, $C_7$), 134.6 (s, $C_9$), 121.9 (d, J=9.1 Hz, $C_{10}$), 108.0 (s, $C_3$), 107.9 (d, J=23.2 Hz, $C_5$), 62.8 (s, $OCH_3$), 59.3 (s, $NCH_2CH_2CH_2$), 54.3 (s, $C_{1'}$ and $C_{4'}$), 51.2 (d, J=4.7 Hz, $C_{2'}$ and $C_{3'}$), 41.0 (s, CH(cPr)), 32.3 (s, $CH_2$), 30.1 (s, $CH_2$), 30.0 (s, $2CH_2$), 29.8 (s, $CH_2$), 27.9 (s, $CH_2$), 27.3 (s, $CH_2$), 23.1 (s, $CH_2$), 14.3 (s, $CH_3$), 9.8 (s, $2CH_2$(cPr)). IR (neat): v=3071; 2924, 2852, 2770, 1729, 1618, 1601, 1536, 1506, 1441, 1394, 1384, 1313, 1281, 1239, 1206, 1188, 1148, 1129, 1116, 1091, 1055, 1042, 1003, 959, 937, 888, 879, 831, 821, 805, 730, 710 $cm^{-1}$; HRMS (+ESI) m/z: $[M+H]^+$ calcd for $C_{28}H_{40}FN_3O_4$: 502.3082, found, 502.3077. Elemental Analysis: C=67.28%, H=8.21%, N=8.31%, calcd C=67.04%, H=8.04%, N=8.38%.

ylic acid and 1-cyclopropyl-6-fluoro-8-methoxy-7-(4-undecylpiperazin-1-yl)-4-oxo-1,4-dihydroquinoline-3-carboxylate undecyl ester were obtained according to reference Quin 17, starting from 1-cyclopropyl-6-fluoro-8-methoxy-4-oxo-7-(piperazin-1-yl)-1,4-dihydroquinoline-3-carboxylic acid (2.13 g, 5.60 mmol), 1-iodoundecane (4.94 g, 17.5 mmol) and $NaHCO_3$ (3.04 g, 36.2 mmol) in dry DMF (450 mL). This product was sufficiently pure for the further reaction.

1-cyclopropyl-6-fluoro-8-methoxy-7-(4-undecylpiperazin-1-yl)-4-oxo-1,4-dihydroquinoline-3-carboxylic acid (1.01 g, 1.96 mmol, 35% over two steps, yellow powder) was obtained according to reference Quin 17, starting from the later mixture and LiOH (580 mg, 24.2 mmol) in an $EtOH/H_2O$ (5/2) mixture (400 mL).

$^1H$ NMR (400 MHz, $CD_2Cl_2$, δ): 14.77 (broad s, 1H, $CO_2H$), 8.77 (s, 1H, $H_2$), 7.80 (d, $^3J_{H-F}$=12.4 Hz, 1H, $H_5$), 4.04 (m, 1H, CH(cPr)), 3.77 (s, 3H, $OCH_3$), 3.43 (broad s, 4H, $H_{2'}$ and $H_{3'}$), 2.58 (broad s, 4H, $H_{1'}$ and $H_{4'}$), 2.39 (m, 2H, $NCH_2CH_2CH_2$), 1.50 (m, 2H, $NCH_2CH_2CH_2$), 1.40-1.16 (m, 18H, $CH_2$, $CH_2$(cPr)), 1.02-0.95 (m, 2H, $CH_2$(cPr)), 0.89 (t, $^3J_{H-H}$=6.8 Hz, 3H, $CH_3$). $^{13}C$ NMR (100 MHz, $CD_2Cl_2$, δ): 177.2 (d, J=3.1 Hz, $C_4$), 166.9 (s, $CO_2H$), 157.9 (d, J=250.8 Hz, $C_6$), 154.6 (s, $C_2$), 145.3 (d, J=5.8 Hz, $C_8$), 139.6 (d, J=11.7 Hz, $C_7$), 134.1 (s, $C_9$), 121.8 (d, J=9.2 Hz, $C_{10}$), 108.2 (s, $C_3$), 107.9 (d, J=23.3 Hz, $C_5$), 62.6 (s, $OCH_3$), 59.1 (s, $NCH_2CH_2CH_2$), 54.0 (s, $C_{1'}$ and $C_{4'}$), 50.8 (d, J=4.6 Hz, $C_{2'}$ and $C_{3'}$), 40.7 (s, CH(cPr)), 32.1 (s, $CH_2$), 29.8 (s, $CH_2$), 29.7 (s, $CH_2$), 29.5 (s, $CH_2$), 27.7 (s, $CH_2$), 26.9 (s, $CH_2$), 25.5 (s, $CH_2$), 22.8 (s, $CH_2$), 14.3 (s, $CH_3$), 9.7 (s, $2CH_2$(cPr)). MP=136.3° C. Elemental Analysis: C=67.27%, H=8.14%, N=8.02%, calcd C=67.55%, H=8.21%, N=8.15%.

Preparation of 1-cyclopropyl-6-fluoro-8-methoxy-7-(4-dodecylpiperazin-1-yl)-4-oxo-1,4-dihydroquinoline-3-carboxylic acid (compound 20)

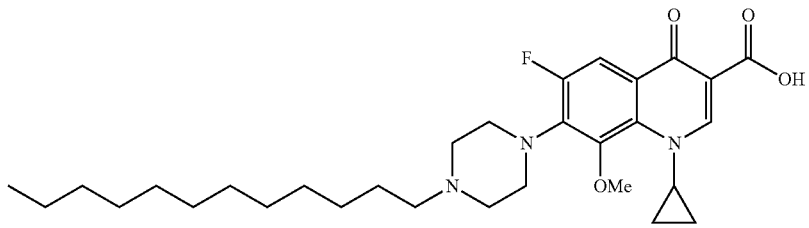

Preparation of 1-cyclopropyl-6-fluoro-8-methoxy-7-(4-undecylpiperazin-1-yl)-4-oxo-1,4-dihydroquinoline-3-carboxylic acid (compound 19)

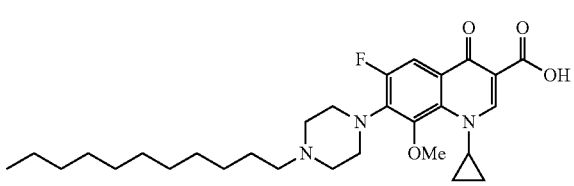 [SMILES: CCCCCCCCCCCN1CCN(c2c(F)cc3c(=O)c(C(=O)O)cn(C4CC4)c3c2OC)CC1]

A mixture of 1-cyclopropyl-6-fluoro-8-methoxy-7-(4-undecylpiperazin-1-yl)-4-oxo-1,4-dihydroquinoline-3-carbox- A mixture of 1-cyclopropyl-6-fluoro-8-methoxy-7-(4-dodecylpiperazin-1-yl)-4-oxo-1,4-dihydroquinoline-3-carboxylic acid and 1-cyclopropyl-6-fluoro-8-methoxy-7-(4-dodecylpiperazin-1-yl)-4-oxo-1,4-dihydroquinoline-3-carboxylate dodecyl ester were obtained according to reference Quin 17, starting from 1-cyclopropyl-6-fluoro-8-methoxy-4-oxo-7-(piperazin-1-yl)-1,4-dihydroquinoline-3-carboxylic acid (2.32 g, 6.08 mmol), 1-iodododecane (4.94 g, 17.5 mmol) and $NaHCO_3$ (3.04 g, 36.2 mmol) in dry DMF (450 mL). This product was sufficiently pure for the further reaction.

1-cyclopropyl-6-fluoro-8-methoxy-7-(4-dodecylpiperazin-1-yl)-4-oxo-1,4-dihydroquinoline-3-carboxylic acid (1.03 g, 1.94 mmol, 32% over two steps, yellow powder) was obtained according to reference Quin 17, starting from the later mixture and LiOH (580 mg, 24.2 mmol) in an $EtOH/H_2O$ (5/2) mixture (400 mL).

1H NMR (400 MHz, $CD_2Cl_2$, δ): 14.77 (broad s, 1H, $CO_2H$), 8.77 (s, 1H, $H_2$), 7.80 (d, $^3J_{H-F}$=12.4 Hz, 1H, $H_5$), 4.04 (m, 1H, CH(cPr)), 3.77 (s, 3H, $OCH_3$), 3.43 (broad s, 4H, $H_{2'}$ and $H_{3'}$), 2.58 (broad s, 4H, $H_{1'}$ and $H_{4'}$), 2.39 (m, 2H, $NCH_2CH_2CH_2$), 1.50 (m, 2H, $NCH_2CH_2CH_2$), 1.40-1.16 (m, 20H, $CH_2$, $CH_2$(cPr)), 1.02-0.95 (m, 2H, $CH_2$(cPr)), 0.89 (t, $^3J_{H-H}$=6.8 Hz, 3H, $CH_3$). $^{13}C$ NMR (100 MHz, $CD_2Cl_2$, δ): 177.1 (d, J=3.1 Hz, $C_4$), 166.9 (s, $CO_2H$), 157.8 (d, J=250.8 Hz, $C_6$), 154.5 (s, $C_2$), 145.4 (d, J=5.8 Hz, $C_8$), 139.7 (d, J=11.7 Hz, $C_7$), 134.0 (s, $C_9$), 121.6 (d, J=9.2 Hz, $C_{10}$), 108.2 (s, $C_3$), 107.8 (d, J=23.3 Hz, $C_5$), 62.6 (s, $OCH_3$), 59.1 (s, $NCH_2CH_2CH_2$), 53.9 (s, $C_{1'}$ and $C_{4'}$), 50.7 (d, J=4.6 Hz, $C_{2'}$ and $C_{3'}$), 40.6 (s, CH(cPr)), 32.0 (s, $CH_2$), 29.7 (s, $CH_2$), 29.6 (s, $CH_2$), 29.4 (s, $CH_2$), 27.7 (s, $CH_2$), 26.8 (s, $CH_2$), 22.8 (s, $CH_2$), 14.2 (s, $CH_3$), 9.6 (s, $2CH_2$(cPr)). MP=134.6° C. Elemental Analysis: C=67.89%, H=8.49%, N=7.82%, calcd C=68.03%, H=8.37%, N=7.93%.

Preparation of 1-cyclopropyl-6-fluoro-8-methoxy-7-(4-tetradecylpiperazin-1-yl)-4-oxo-1,4-dihydroquinoline-3-carboxylic acid (compound 22)

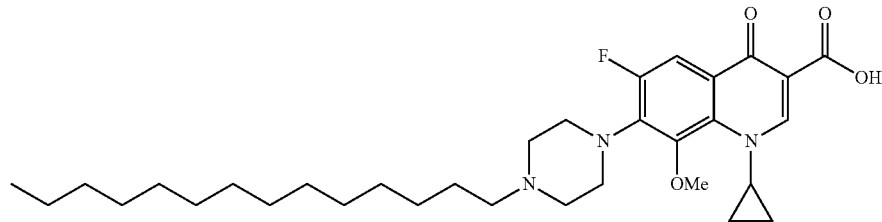 [SMILES: CCCCCCCCCCCCCCN1CCN(c2c(F)cc3c(=O)c(C(=O)O)cn(C4CC4)c3c2OC)CC1]

A mixture of 1-cyclopropyl-6-fluoro-8-methoxy-7-(4-tetradecylpiperazin-1-yl)-4-oxo-1,4-dihydroquinoline-3-carboxylic acid and 1-cyclopropyl-6-fluoro-8-methoxy-7-(4-tetradecylpiperazin-1-yl)-4-oxo-1,4-dihydroquinoline-3-carboxylate tetradecyl ester were obtained according to reference Quin 17, starting from 1-cyclopropyl-6-fluoro-8-methoxy-4-oxo-7-(piperazin-1-yl)-1,4-dihydroquinoline-3-carboxylic acid (2.18 g, 5.71 mmol), 1-bromotetradecane (4.714 g, 17.0 mmol) and $NaHCO_3$ (2.94 g, 35.0 mmol) in dry DMF (450 mL). This product was sufficiently pure for the further reaction.

1-cyclopropyl-6-fluoro-8-methoxy-7-(4-tetradecylpiperazin-1-yl)-4-oxo-1,4-dihydroquinoline-3-carboxylic acid (1.02 g, 1.83 mmol, 32% over two steps, yellow powder) was obtained according to reference Quin 17, starting from the later mixture and LiOH (580 mg, 24.2 mmol) in an $EtOH/H_2O$ (5/2) mixture (400 mL).

1H NMR (400 MHz, $CD_2Cl_2$, δ): 14.77 (broad s, 1H, $CO_2H$), 8.77 (s, 1H, $H_2$), 7.80 (d, $^3J_{H-F}$=12.4 Hz, 1H, $H_5$), 4.04 (m, 1H, CH(cPr)), 3.77 (s, 3H, $OCH_3$), 3.43 (broad s, 4H, $H_{2'}$ and $H_{3'}$), 2.58 (broad s, 4H, $H_{1'}$ and $H_{4'}$), 2.39 (m, 2H, $NCH_2CH_2CH_2$), 1.50 (m, 2H, $NCH_2CH_2CH_2$), 1.40-1.16 (m, 24H, $CH_2$, $CH_2$(cPr)), 1.02-0.95 (m, 2H, $CH_2$(cPr)), 0.89 (t, $^3J_{H-H}$=6.8 Hz, 3H, $CH_3$). $^{13}C$ NMR (100 MHz, $CD_2Cl_2$, δ): 177.1 (d, J=3.1 Hz, $C_4$), 166.8 (s, $CO_2H$), 157.8 (d, J=250.8 Hz, $C_6$), 154.5 (s, $C_2$), 145.5 (d, J=5.8 Hz, $C_8$), 139.7 (d, J=11.7 Hz, $C_7$), 134.0 (s, $C_9$), 121.7 (d, J=9.2 Hz, $C_{10}$), 107.9 (s, $C_3$), 107.8 (d, J=23.3 Hz, $C_5$), 62.5 (s, $OCH_3$), 59.1 (s, $NCH_2CH_2CH_2$), 54.0 (s, $C_{1'}$ and $C_{4'}$), 50.7 (d, J=4.6 Hz, $C_{2'}$ and $C_{3'}$), 40.6 (s, CH(cPr)), 32.0 (s, $CH_2$), 29.7 (s, $CH_2$), 29.6 (s, $CH_2$), 29.4 (s, $CH_2$), 27.7 (s, $CH_2$), 26.6 (s, $CH_2$), 22.8 (s, $CH_2$), 14.2 (s, $CH_3$), 9.6 (s, $2CH_2$(cPr)). MP=131.1° C. Elemental Analysis: C=69.10%, H=8.85%, N=7.44%, calcd C=68.91%, H=8.67%, N=7.53%.

Preparation of 1-cyclopropyl-6-fluoro-7-(4-hexadecylpiperazin-1-yl)-8-methoxy-4-oxo-1,4-dihydroquinoline-3-carboxylic acid (Quin 20)

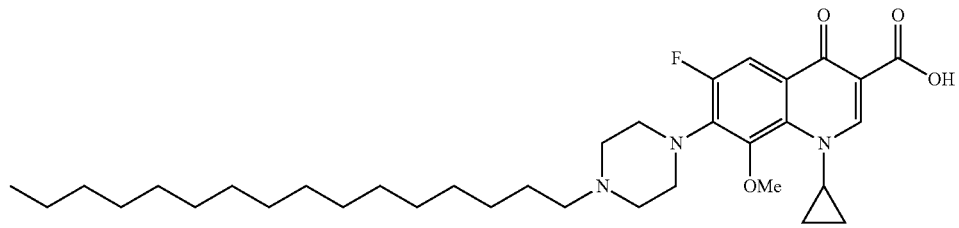 [SMILES: CCCCCCCCCCCCCCCCN1CCN(c2c(F)cc3c(=O)c(C(=O)O)cn(C4CC4)c3c2OC)CC1]

1-cyclopropyl-6-fluoro-7-(4-hexadecylpiperazin-1-yl)-8-methoxy-4-oxo-1,4-dihydroquinoline-3-carboxylate hexadecyl ester (100 mg, 68%) were obtained according to reference Quin 17, starting from 1-cyclopropyl-6-fluoro-8-methoxy-4-oxo-7-(piperazin-1-yl)-1,4-dihydroquinoline-3-carboxylic acid (70 mg, 0.18 mmol), 1-iodohexadecane (230 mg, 0.65 mmol) and $NaHCO_3$ (200 mg, 2.40 mmol) in dry DMF (18 mL). This product was sufficiently pure for the further reaction.

1-cyclopropyl-6-fluoro-7-(4-hexadecylpiperazin-1-yl)-8-methoxy-4-oxo-1,4-dihydroquinoline-3-carboxylic acid (50 mg, 47% over two steps, white solid) was obtained according to reference Quin 17, starting from the corresponding ester (100 mg, 0.123 mmol) and LiOH (40 mg, 1.67 mmol) in an EtOH/H$_2$O (5/2) mixture (21 mL).

$^1$H NMR (400 MHz, CD$_2$Cl$_2$, δ): 14.79 (broad s, 1H, CO$_2$H), 8.78 (s, 1H, H$_2$), 7.82 (d, $^3J_{H-F}$=12.4 Hz, 1H, H$_5$), 4.04 (m, 1H, CH(cPr)), 3.76 (s, 3H, OCH$_3$), 3.43 (broad s, 4H, H$_{2'}$ and H$_{3'}$), 2.58 (broad s, 4H, H$_{1'}$ and H$_{4'}$), 2.39 (m, 2H, NCH$_2$CH$_2$CH$_2$), 1.50 (m, 2H, NCH$_2$CH$_2$CH$_2$), 1.40-1.16 (m, 28H, CH$_2$, CH$_2$(cPr)), 1.01-0.95 (m, 2H, CH$_2$(cPr)), 0.88 (t, $^3J_{H-H}$=6.8 Hz, 3H, CH$_3$). $^{19}$F NMR (376 MHz, CD$_2$Cl$_2$, δ): −120.1 (s, F$_6$). $^{13}$C NMR (100 MHz, CD$_2$Cl$_2$, δ): 177.5 (d, J=3.0 Hz, C$_4$), 166.9 (s, CO$_2$H), 156.7 (d, J=250.8 Hz, C$_6$), 150.3 (s, C$_2$), 145.9 (d, J=5.8 Hz, C$_8$), 140.1 (d, J=11.7 Hz, C$_7$), 134.6 (s, C$_9$), 121.9 (d, J=9.2 Hz, C$_{10}$), 108.1 (s, C$_3$), 108.0 (d, J=23.3 Hz, C$_5$), 62.8 (s, OCH$_3$), 59.3 (s, NCH$_2$CH$_2$CH$_2$), 54.3 (s, C$_{1'}$ and C$_{4'}$), 51.2 (d, J=4.6 Hz, C$_{2'}$ and C$_{3'}$), 41.0 (s, CH(cPr)), 32.4 (s, CH$_2$), 30.11 (s, 5CH$_2$), 30.07 (s, 3CH$_2$), 30.03 (s, CH$_2$), 29.8 (s, CH$_2$), 27.9 (s, CH$_2$), 27.3 (s, CH$_2$), 23.1 (s, CH$_2$), 14.3 (s, CH$_3$), 9.8 (s, 2CH$_2$(cPr)). IR (neat): v=3078, 3004, 2917, 2850, 2770, 1733, 1620, 1601, 1511, 1443, 1393, 1384, 1370, 1328, 1312, 1281, 1239, 1208, 1187, 1149, 1130, 1115, 1090, 1053, 993, 959, 937, 889, 878, 831, 822, 805, 730, 719 cm$^{-1}$; HRMS (−ESI) m/z: [M−H]$^-$ calcd for C$_{34}$H$_{52}$FN$_3$O$_4$: 584.3863, found, 584.3843.

Preparation of 1-cyclopropyl-6-fluoro-7-(4-(2-ethylhexyl)piperazin-1-yl)-8-methoxy-4-oxo-1,4-dihydroquinoline-3-carboxylic acid (compound 25)

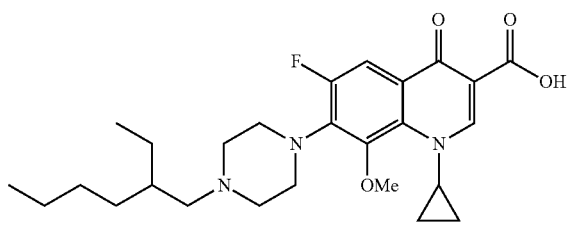 [SMILES: CCCCC(CC)CN1CCN(c2c(F)cc3c(=O)c(C(=O)O)cn(C4CC4)c3c2OC)CC1]

To compound 2 (1 eq.) in dichloromethane, 2-ethylhexanal (1.2 eq.) and acetic acid (6eq.) were added. NaBH(OAc)3 (1.3 eq.) was added portionwise and the mixture was stirred at room temperature overnight. Water (450 ml) was added and the mixture was filtered on celite. The cake was washed with dichloromethane and the phases were separated. The organic phase was washed with water, dried over magnesium sulfate, filtered and concentrated to dryness. Purification on silica gel (DCM/Methanol 90/10, 0.5% AcOH) afforded 1-cyclopropyl-6-fluoro-7-(4-(2-ethylhexyl)piperazin-1-yl)-8-methoxy-4-oxo-1,4-dihydroquinoline-3-carboxylic acid as a white solid (35%).

$^1$H NMR (400 MHz, CD$_2$Cl$_2$, δ): 8.85 (s, 1H, H$_2$), 7.90 (d, $^3J_{H-F}$=12.4 Hz, 1H, H$_5$), 4.06 (m, 1H, CH(cPr)), 3.89 (s, 3H, OCH$_3$), 3.56 (broad s, 4H, H$_{2'}$ and H$_{3'}$), 2.59 (broad s, 4H, H$_{1'}$ and H$_{4'}$), 2.28 (bs, 2H, NCH$_2$CH), 1.49-1.21 (m, 11H, CH$_2$, CH, CH$_2$(cPr)), 1.06-1.00 (m, 2H, CH$_2$(cPr)), 0.89 (m, 6H, 2CH$_3$). $^{13}$C NMR (100 MHz, CD$_2$Cl$_2$, δ): 177.4 (d, J=3.1 Hz, C$_4$), 167.3 (s, CO$_2$H), 156.5 (d, J=250.8 Hz, C$_6$), 150.2 (s, C$_2$), 145.6 (d, J=5.8 Hz, C$_8$), 140.1 (d, J=11.7 Hz, C$_7$), 134.4 (s, C$_9$), 121.8 (d, J=9.2 Hz, C$_{10}$), 117.2 (s, C$_3$), 108.4 (d, J=23.3 Hz, C$_5$), 63.6 (s, OCH$_3$), 62.7 (s, NCH$_2$CH), 54.7 (s, C$_{1'}$ and C$_{4'}$), 51.2 (d, J=4.6 Hz, C$_{2'}$ and C$_{3'}$), 41.0 (s, CH(cPr)), 36.5 (s, CH), 31.9 (s, CH$_2$), 29.4 (s, CH$_2$), 25.0 (s, CH$_2$), 23.6 (s, CH$_2$), 14.6 and 11.2 (s, CH$_3$), 9.8 (s, 2CH$_2$(cPr)). Elemental Analysis: C=65.66%, H=7.49%, N=8.57%, calcd C=65.94%, H=7.66%, N=8.87%.

Preparation of 1-cyclopropyl-6-fluoro-7-(4-octanoylpiperazin-1-yl)-8-methoxy-4-oxo-1,4-dihydroquinoline-3-carboxylic acid (compound 26)

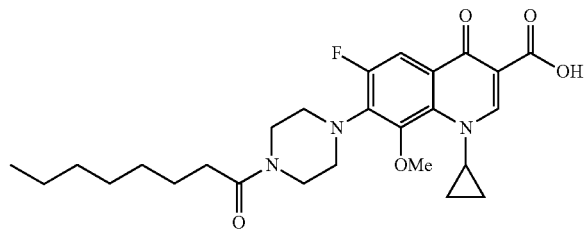 [SMILES: CCCCCCCC(=O)N1CCN(c2c(F)cc3c(=O)c(C(=O)O)cn(C4CC4)c3c2OC)CC1]

1-cyclopropyl-6-fluoro-7-piperazin-1-yl-8-methoxy-4-oxo-1,4-dihydroquinoline-3-carboxylic acid (1 eq.) was dissolved in dichloromethane. At 0° C., triethylamine (1.3 eq.) and acyl chloride (1.5 eq.) were added and the mixture was stirred at room temperature for 1 hour. Cyclo-hexane was added and the mixture was filtered. The filtrate was evaporated and the resulted solid was purified by column chromatography (silicagel, gradient DCM/Methanol 95/15) to afford 1-cyclopropyl-6-fluoro-7-(4-octanoylpiperazin-1-yl)-8-methoxy-4-oxo-1,4-dihydroquinoline-3-carboxylic acid as a white solid (40%).

$^1$H NMR (400 MHz, CD$_2$Cl$_2$, δ): 8.87 (s, 1H, H$_2$), 7.95 (d, $^3J_{H-F}$=12.4 Hz, 1H, H$_5$), 4.06 (m, 1H, CH(cPr)), 3.77 (s, 3H, OCH$_3$), 3.71 (broad s, 4H, H$_{1'}$ and H$_{4'}$), 3.44 (broad s, 4H, H$_{2'}$ and H$_{3'}$), 2.42 (m, 2H, NCH$_2$CH$_2$CH$_2$), 1.68 (m, 2H, NCH$_2$CH$_2$CH$_2$), 1.42-1.23 (m, 12H, CH$_2$), 1.02-0.95 (m, 2H, CH$_2$(cPr)), 0.94 (t, $^3J_{H-H}$=6.8 Hz, 3H, CH$_3$). $^{13}$C NMR (100 MHz, CD$_2$Cl$_2$, δ): 177.4 (d, J=3.1 Hz, C$_4$), 172.5 (s, CO), 167.0 (s, CO$_2$H), 156.4 (d, J=250.8 Hz, C$_6$), 150.5 (d, J=5.8 Hz, C$_8$), 146.0 (d, J=11.7 Hz, C$_7$), 139.4 (s, C$_9$), 134.3 (s, C$_3$), 122.9 (d, J=9.2 Hz, C$_{10}$), 108.7 (d, J=23.3 Hz, C$_5$), 63.0 (s, OCH$_3$), 51.3 (bs, C$_{1'}$, C$_{4'}$, C$_{2'}$ and C$_{3'}$), 40.9 (s, CH(cPr)), 33.9 (s, CH$_2$), 32.1 (s, CH$_2$), 29.9 (s, CH$_2$), 29.5 (s, CH$_2$), 25.8 (s, CH$_2$), 23.0 (s, CH$_2$), 14.5 (s, CH$_3$), 10.0 (s, 2CH$_2$(cPr)). Elemental Analysis: C=63.31%, H=7.10%, N=8.08%, calcd C=64.05%, H=7.03%, N=8.62%.

2. Biological Data 2.1. In Vitro Antimicrobial Activity on *M. tuberculosis* H37Rv Growth and DNA Supercoiling of DNA Gyrase A) For Compounds Quin 9 to Quin 20

Materials and Methods

Reagents

The following three quinolones were provided by their corresponding manufacturers: gatifloxacin (Grünenthal, Levallois-Perret, France); ciprofloxacin and moxifloxacin (Bayer Pharma, Puteaux, France).

In Vitro Antimicrobial Activity

*M. tuberculosis* H37Rv and mutants strains harbouring mutations in DNA gyrase commonly observed in clinical strains resistant to quinolones (GyrA A90V and GyrA D94G) were grown on Löwenstein-Jensen medium. MICs were determined by the proportion method as described previously (Guillemin, I.; Jarlier V.; Cambau E. *Antimicrob. Agents Chemother.* 1998, 42, 2084). Briefly, 10$^3$ and 10$^5$ CFU were spread onto 7H11 agar supplemented with 10% oleic acid-albumin-dextrose-catalase and containing serial twofold dilutions of the compound. Colonies were enumerated after 21 to 30 days of incubation at 37° C. The MIC was defined as the drug concentration at which the bacterial growth was reduced to 1% or less of that of the drug-free control culture (Inderlied, C. B.; Nash K. A. In Antibiotics in laboratory medicine, 4th ed.; M. D. V. Lorian, Eds; The Williams & Wilkins Co.; Baltimore, Md., 1996; pp 127-175).

The interference with the replication of M. tuberculosis within macrophages was measured by a phenotypic cell-based assay that uses automated confocal fluorescence microscopy for high throughput screening of chemicals (Christophe T. et al. High Content Screening Identifies Decaprenyl-Phosphoribose 29 Epimerase as a Target for Intracellular Antimycobacterial Inhibitors, PloS pathogens, 2009 October; 5(10):e1000645).

DNA Supercoiling Assay

M. tuberculosis DNA gyrase was purified as described previously (Aubry, A.; Pan, X.-S.; Fisher, L. M.; Jarlier, V.; Cambau, E. Antimicrob. Agents Chemother. 2004, 48, 1281). The reaction mixture (total volume, 30 μl) contained DNA gyrase assay buffer (40 mM Tris-HCl [pH 7.5], 25 mM KCl, 6 mM magnesium acetate, 2 mM spermidine, 4 mM dithiothreitol, bovine serum albumin [0.36 μg/mL], 10 mM potassium glutamate, 1 mM ATP [pH 8.0]) and relaxed pBR322 DNA (0.4 μg) as the substrate. Gyrase proteins (300 ng of GyrA and 250 ng of GyrB) were mixed in the presence of increasing concentrations of quinolones for 1 h at 37° C. for M. tuberculosis. Reactions were terminated by the addition of 50% glycerol containing 0.25% bromophenol blue, and the total reaction mixture was subjected to electrophoresis in a 1% agarose gel in 0.5×TBE (Tris-borate-EDTA, pH 8.3) buffer. After electrophoresis for 5.5 h at 50 V, the gel was stained with ethidium bromide (0.7 μg/mL). The inhibitory effect of quinolones on DNA gyrase was assessed by determining the concentration of drug required to inhibit the supercoiling activity of the enzyme by 50% ($IC_{50}$). Supercoiling activity was assessed by tracing the brightness of the bands corresponding to the supercoiled pBR322 DNA with Molecular Analyst software (Bio-Rad).

Results

All the fluoroquinolones synthesized exhibit antibacterial activity against wild-type M. tuberculosis strain, especially Quin 9, 16, 18, 19 and 20 (MICs<1 Surprisingly, none of them inhibit (or, at very high concentrations) the wild-type M. tuberculosis DNA gyrase. Moreover, two of these new quinolones (Quin 18 and Quin 19) are of particular interest. They exhibit high antibacterial activity against WT (H37Rv strain) but also against quinolone-resistant M. tuberculosis strains (D94V and A90V strains).

Altogether, these results suggest (i) a different (or additional) mode of action than those exhibited by quinolones, and (ii) an antibacterial activity against M. tuberculosis strains, including XDR-TB strains (i.e. strains resistant to quinolones).

B) For Compounds 15 to 20, Quin 18 and Quin 19

Materials and Methods

Reagents

Moxifloxacin (MOX), used a positive control, was provided by its corresponding manufacturer (Bayer Pharma, Puteaux, France).

In Vitro Antimicrobial Activity

M. tuberculosis H37Rv wild-type and mutants strains harbouring mutations in DNA gyrase commonly observed in clinical strains resistant to quinolones (GyrA A90V, GyrA D94G and GyrB D500N), and multidrug-resistant M. tuberculosis clinical strains (MDR; defined as resistance to the key antituberculous drugs isoniazid and rifampin; 2 of the 3 strains being also resistant to aminoglycosides and therefore classified as pre-XDR strains (eXtremely Drug Resistant); GV1503014223, KC1503006247, XCC1503082245) were grown on Löwenstein-Jensen medium. MICs were determined by the proportion method as described previously (Guillemin, I.; Jarlier V.; Cambau E. Antimicrob. Agents Chemother. 1998, 42, 2084). Briefly, $10^3$ and $10^5$ CFU were spread onto 7H11 agar supplemented with 10% oleic acid-albumin-dextrose-catalase and containing serial twofold dilutions of the compound. Colonies were enumerated after 3 to 30 days of incubation at 37° C. (depending on the mycobacterial species). The MIC was defined as the drug concentration at which the bacterial growth was reduced to

TABLE 2

Activities of eight compounds inhibiting M. tuberculosis H37Rv growth (MICs), and DNA supercoiling of DNA gyrase (IC50) in μM

| Cpd | $R^2$ | $R^1$ | clogP[a] | Intra mac. | DNA gyrase- $IC_{50}$ | MIC (M. tuberculosis) μM | | |
|---|---|---|---|---|---|---|---|---|
| | | | | | | WT | D94G | A90V |
| Gatifloxacin[c] | OMe | H | −0.27 | nd | 6.8 | 0.32 | 2.66 | 5.33 |
| Moxifloxacin[c] | OMe | —[b] | −1.50 | 4.16 | 5 | 0.63 | 10 | 5 |
| Ciprofloxacin[d] | H | H | −0.73 | nd | 15 | 1.5 | ≥24 | ≥24 |
| Quin 9 | H | $C_{10}$ | 4.61 | 1 | 120 | 0.5 | ≥4.8 | ≥4.8 |
| Quin 10 | H | $C_{16}$ | 7.78 | >25 | 105 | 57 | nd | nd |
| Quin 15 | H | $C_5$ | 1.97 | inactive | 76 | 6 | nd | nd |
| Quin 16 | H | $C_8$ | 3.55 | <0.05 | 135 | ≤0.2 | 13.5 | 6.7 |
| Quin 17 | OMe | $C_5$ | 1.91 | <0.02 | 60 | 3.5 | >18.5 | 18.5 |
| Quin 18 | OMe | $C_8$ | 3.49 | 0.65 | 195 | ≤0.12 | 2 | 0.5 |
| Quin 19 | OMe | $C_{10}$ | 4.55 | 10 | 150 | 0.25 | 1 | 0.5 |
| Quin 20 | OMe | $C_{16}$ | 7.73 | 0.65 | 121 | 0.2 | >13.7 | 13.7 | nd = not determined

Intra mac. = activity inside macrophages

MIC = Maximum inhibitory concentration

[a]clogP was calculated using ChemdrawUltra 12.0 software

[b]moxifloxacin presents a different substitution in R7 and no alkyl chain on the terminal nitrogen atom

[c]gatifloxacin and moxifloxacin biological activities indicated here are those published previously (Poissy et al., Antimicrob. Agents Chemother., 2010, p4765-71)

[d] ciprofloxacin biological activities indicated here are unpublished data performed against the same strains than in the above publication (Poissy, Antimicrob. Agents Chemother., 2010, p4765-71)

1% or less of that of the drug-free control culture (Inderlied, C. B.; Nash K. A. In Antibiotics in laboratory medicine, 4th ed.; M. D. V. Lorian, Eds; The Williams & Wilkins Co.; Baltimore, Md., 1996; pp 127-175).

Results

The results are presented in Table 3.

TABLE 3

| Compound | MIC ($\mu$M) | | | | | | |
|---|---|---|---|---|---|---|---|
| | MOX | 15 | Quin 18 | Quin 19 | 17 | 19 | 20 |
| M. tuberculosis H37Rv | 1.2 | 2.2 | 0.12 | <0.12 | 0.12 | 0.25 | 0.47 |
| M. tuberculosis H37Rv GyrB D500N | 12.5 | 2.2 | <0.12 | 0.5 | 0.5 | 2 | 0.23 |
| M. tuberculosis H37Rv GyrA A90V | 12.5 | 2.2 | 2 | 1 | 2 | 10 | 1.9 |
| M. tuberculosis H37Rv GyrA D94G | 12.5 | 0.5 | 2 | 2 | 2 | 10 | 1.9 |
| GV1503014223 | 0.6 | 1 | <0.12 | <0.12 | <0.12 | 0.5 | 0.47 |
| KC1503006247 | 0.6 | 1 | <0.12 | <0.12 | <0.12 | 0.12 | 0.47 |
| XCC1503082245 | 0.6 | 1 | 0.12 | 0.5 | 1 | 0.5 | 0.47 |

MIC = Maximum inhibitory concentration

All the new compounds synthesized demonstrated antibacterial activity against wild-type M. tuberculosis strain. Especially, Quin18, Quin19, compounds 17, 19 and 20, have MICs which are below moxifloxacin MIC's (1.2 Interestingly, they also exhibited high antibacterial activity against quinolone-resistant M. tuberculosis strains (GyrB D500N, GyrA D94G and GyrA A90V strains). It should be noticed that for Quin18, Quin19, compounds 17, 19 and 20, MICs are similar or increased in FQ-resistant strains, depending on the mutation, but they are still ≤2 $\mu$M for Quin18, Quin19, compounds 17 and 20, i.e. similar to this of moxifloxacin against wild-type strain. Very interestingly MICs of the most potent compounds were similar between MDR strains and wild-type M. tuberculosis H37Rv strain.

2.2. Determination of the Minimal Effective Dosage (MED) of Quin18 and Quin19 in the Murine TB Model Materials and Methods Four-week-old Balb/C/J female mice were infected intravenously with $10^6$ CFU of M. tuberculosis H37Rv strain. On the day following the infection (D1), 10 mice were sacrificed to determine the exact baseline values of spleen weight and CFU counts in the lungs. The remaining mice were allocated to the following treatment groups: an untreated negative control group for survival monitoring, a positive control group treated for 1 month with isoniazid (INH) 25 mg/kg/d, ten test groups were treated with Quin18 and Quin19 at increasing dosages (25 mg/kg/d; 50 mg/kg/d; 100 mg/kg/d; 150 mg/kg/d) given by oral gavage, and two additional test groups were treated intravenously with Quin18 25 mg/kg/d and 100 mg/kg/d. All the groups contained 10 mice and were treated from D1 to D28, 5 days a week. The parameters used for assessing the severity of infection and the effectiveness of treatments were survival rate, spleen weight, gross lung lesions and CFU counts in the lungs.

The minimal effective dosage was defined as the minimal dosage able to prevent mortality of the mice, spleen enlargement and the occurrence of gross lung lesions. CFU counts were considered to be a more precise way of determining the dose-ranging efficacy of Quin18 and Quin19.

Survival rates between groups were plotted on a Kaplan-Meier curve and compared using the log-rank test.

Results

Figure 2:
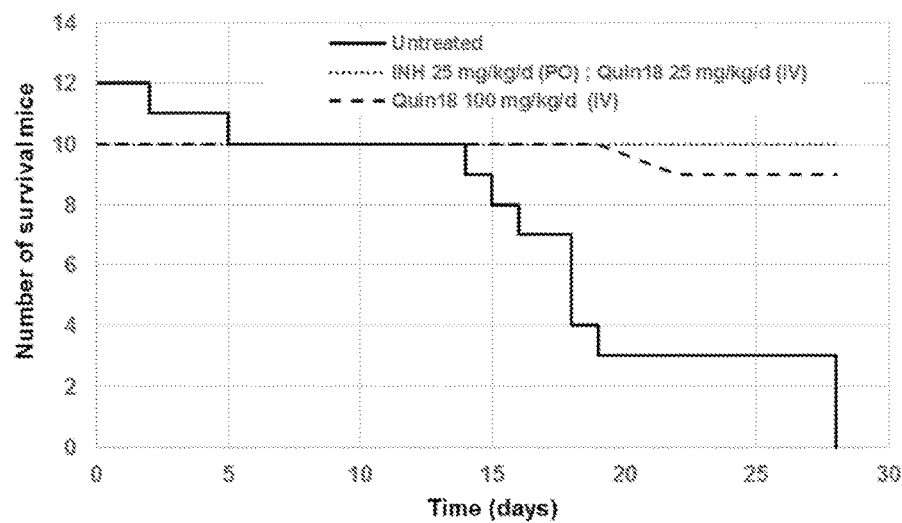
FIG. 2 is a graph showing the evolution of survival mice infected with wild-type *M. tuberculosis* strain H37rv and treated intravenously with Quin18.

The results are presented in Table 4, FIGS. 1 and 2.

Survival among mice infected with wild-type M. tuberculosis strain H37Rv and treated with either Quin18 and Quin19, whatever the dosage (25, 50, 100 and 150 mg/kg/d) and the administration route (by gavage (FIG. 1) or intravenously (FIG. 2) for Quin18) was statistically superior to untreated group and similar to the group treated by the reference drug, i.e. isoniazid 25 mg/kg/d (curves can be superimposed).

Mice weights were lower in untreated groups than in tests groups, where mice weights were similar between groups treated by the new compounds or by isoniazid. Spleen weights which are an indirect sign of infection, were higher in the untreated group than in groups treated by the two compounds given by gavage and the group treated by isoniazid, whereas the groups treated intravenously by Quin18 have spleen weights similar than the untreated group.

Survival rates over time by dose are shown in FIGS. 1 and 2. Survival did not differed between tests groups where survival were significantly different from the survival of the untreated group and comparable to the survival of the positive control group treated by isoniazid, even at the same dosage, i.e. 25 mg/kg/j.

CFU counts, considered to be a more precise way of determining the dose-ranging efficacy of Quin18 and Quin19, are pending.

CONCLUSION

These results show that Quin18 and Quin19, given orally, have outstanding efficacy in a mouse model of tuberculosis. An oral drug for tuberculosis, especially MDR ad XDR TB, is a well-recognized clinical need and Quin18 and Quin19 have tremendous promise in this regard.

TABLE 4

| Compound | Dosage (mg/kg/j) | Administration | Survival | | p* | Mice weight (mg) | Spleen weight (mg) |
|---|---|---|---|---|---|---|---|
| | | | No. mice | No. death | | | |
| No treatment | na | na | 12 | 9 | | 13.6 ± 3.9 | 364.2 ± 172.5 |
| Isoniazid | 25 | Gavage | 10 | 0 | 0.0005 | 20.2 ± 1 | 237 ± 73.8 |
| Quin 18 | 25 | Gavage | 10 | 0 | 0.0005 | 19.4 ± 0.9 | 258.6 ± 155 |
| | 50 | Gavage | 10 | 0 | 0.0005 | 20 ± 1.6 | 231 ± 63.3 |
| | 100 | Gavage | 10 | 0 | 0.0005 | 19.4 ± 1.5 | 210 ± 104.1 |
| | 150 | Gavage | 10 | 0 | 0.0005 | 20.3 ± 0.8 | 239.8 ± 129.3 |
| | 25 | Intravenously | 10 | 0 | 0.0005 | 20 ± 1 | 391 ± 89.7 |
| | 100 | Intravenously | 10 | 1 | 0.0015 | 20 ± 1.1 | 400 ± 7.7 |
| Quin 19 | 25 | Gavage | 10 | 1 | 0.00048 | 19.3 ± 2.6 | 332 ± 141.1 |
| | 50 | Gavage | 10 | 2 | 0.0248 | 18 ± 3.4 | 305.6 ± 181.5 |

TABLE 4-continued

| Compound | Dosage (mg/kg/j) | Administration | Survival No. mice | Survival No. death | p* | Mice weight (mg) | Spleen weight (mg) |
|---|---|---|---|---|---|---|---|
| | 100 | Gavage | 10 | 0 | 0.0005 | 20.2 ± 1.3 | 253 ± 127.2 |
| | 150 | Gavage | 10 | 0 | 0.0005 | 20.7 ± 0.8 | 222 ± 106.2 |

*p value of survival comparing to untreated mice, log rank survival test 2.3. Evaluation of Acute Toxicity of Quin 18 and Quin 19 in Healthy Female CD-1 Mice after a Single Treatment The aim of this study was to evaluate the acute toxicity of two new compounds (Quin 18 and Quin 19) in healthy female CD-1 after a single oral treatment at D0.

A solubility assay was performed on both Quin 18 and Quin 19 in appropriated vehicles for per os injection into mice to obtain a fine suspension at maximal concentration (MC) of each compound. The solubility of each compound in each vehicle was evaluated by observation of potential precipitate. Nine common excipients (Ethanol 5%, Glycerin 15%, Polyethylene glycol 300 50%, Polyethylene glycol 400 9%, Polysorbate 80 0.4%, Propylene glycol 68%, 2-hydroxypropyl-cyclodextrin 20%, Methyl cellulose 0.5% and corn oil) were assayed during this study.

The followings results are presented for polysorbate 80 0.4% and corn oil, the excipients allowing the best solubilisation of Quin 18 and Quin 19, respectively.

The first dose (MC) was the maximal concentration to obtain a fine suspension of the Test Substances in adapted solvent for animals. According to the results obtained with the highest dose of each molecule, concentrations for each compound could be decreased or increased.

Toxicity of treatment was evaluated by monitoring of animals (general signs of pharmacologic and toxicity effects, morbidity, mortality and evident signs of toxicity, as well as twice-weekly monitoring for clinical signs and body weight) until the end of the experiment (D14). At the end of the experiment, animals were sacrificed and macroscopic autopsy was performed.

Materials and Methods

Test Substances

Two Test Substances Quin 18 (MW: 472.13.6 g/mole, purity>99%) and Quin 19 (MW: 501.70 g/mole, purity>99%), were provided to C.RIS Pharma and stored at room temperature.

Animal Purchasing and Caging

Thirty-six (36) females CD-1 mice (RjOrl:SWISS), 7 weeks old were obtained from Janvier (Le Genest-Saint-Isle, France). Animals were maintained for at least 5 days in our conventional animal care unit before the beginning of the study, The animal care unit is authorized by the French Ministries of Agriculture and Research (agreement No. B 35 288-1). Animal experiments will be performed according to ethical guidelines of animal experimentations.

Environment

The animals were maintained in rooms under controlled conditions of temperature (22±3° C.), humidity (50±20%), photoperiod (12 h light/12 h dark) and air exchange. The air handling system is programmed for 14 air changes an hour, with no recirculation. Fresh outside air passes through filters, before being diffused evenly into each room. All personnel working under conventional conditions follow specific guidelines regarding hygiene and clothing when they enter in the animal husbandry area, according to the standard operating procedure No GEN-006.

Animal Husbandry and Caging

Animals are housed in makrolon cages (Ref 03120133, Genestil, France) that are equipped to provide food and water. The standard size cages used are 820 $cm^2$ with a maximum of 10 mice per cage according to the standard operating procedure No. TEC-106. Bedding for animals is wood shavings (Ref. Toplit select fine, SAFE, Augy, France), replaced once a week.

In order to increase the animal welfare, some enrichment material of living environment was included in cage: strip of poplar wood (Ref. TOP WOODWOOL, Safe, France).

Food and Drink

Animal food was purchased from SAFE France. The type of controlled granules was A04. The food was provided ad libitum, being placed in the metal lid on top of the cage. Water was also provided ad libitum from water bottles equipped with rubber stoppers and sipper tubes. Water bottles were cleaned and replaced once a week.

Animal and Cage Identification

Mice were identified with one ISO transponder 8 mm (Genestil, France), according to the standard operating procedure No. TEC-167. Transponders were detected by the GES reader 2S (Rumitag, Spain). In the case of dysfunction of a transponder at any time, a new one was injected to the mouse. Each cage was labeled with a specific code corresponding to the number of the study and the number of the group.

Randomization of Mice

After acclimation period, mice were weighted and randomized according to body weight criteria in 12 groups (3 mice/group), according to the standard operating procedure No. TEC-086. The mean body weight of groups will not be statistically different.

Preparation of Test Substances and Vehicles

The vehicle A (VA) was a solution of polysorbate 80 0.4%. It was prepared by weighing polysorbate 80 and diluted in NaCl 0.9%.

The vehicle B (VB) was corn oil ready to use.

Quin 18 was prepared at a concentration of 10 mg/ml or 20 mg/ml by dissolving the proper content of Quin18 in polysorbate 80 0.4% with or without sonication. Quin 18 was used pure or diluted in polysorbate 80 0.4% to obtain working concentrations. Quin 18 was kept at room temperature during treatment time and injected at room temperature.

Quin 19 was prepared at a concentration of 10 mg/ml or 20 mg/ml by dissolving the proper content of the Quin 19 in corn oil with or without sonication. Quin 19 was used pure or diluted in corn oil to obtain working concentrations. Quin 19 was kept at room temperature during treatment time and injected at room temperature.

Treatment and Experimental Design

Mice of each group were administered by per os (PO) injection at 10 ml/kg according to the standard operating procedure No. TEC-078. The recommended volume for per os (PO) administration in mice is 10 ml/kg.

The experimental groups were defined as described below and as in Table 5:
Test Substance (Quin18):

The Group $V_{A1}$ was treated with polysorbate 80 0.4% (Vehicle A) at 10 ml/kg according to the treatment schedule Q1Dx1.

The Group A1 was treated at 100 mg/kg with Quin18 at 10 mg/ml (with sonication) according to the treatment schedule Q1Dx1.

The Group A2 was treated at 200 mg/kg with Quin18 at 20 mg/ml (with sonication) according to the treatment schedule Q1Dx1.

The Group A3 was treated at 100 mg/kg with Quin18 at 10 mg/ml (without sonication) according to the treatment schedule Q1Dx1.

The Group $V_{A4}$ was treated with polysorbate 80 0.4% (Vehicle A) at 10 ml/kg according to the treatment schedule 2Q1Dx1 (with 2 hours between the 2 injections).

The Group A4 was treated at 200 mg/kg with Quin18 at 10 mg/ml (without sonication) according to the treatment schedule 2Q1Dx1 (with 2 hours between the 2 injections).
Test Substance (Quin19):

The Group $V_{B1}$ was treated with corn oil (Vehicle B) at 10 ml/kg according to the treatment schedule Q1Dx1.

The Group B1 was treated at 100 mg/kg with the Test Substance at 10 mg/ml (with sonication) according to the treatment schedule Q1Dx1.

The Group B2 was treated at 200 mg/kg with the Test Substance at 20 mg/ml (with sonication) according to the treatment schedule Q1Dx1.

The Group B3 was treated at 200 mg/kg with the Test Substance at 20 mg/ml (without sonication) according to the treatment schedule Q1Dx1.

The Group $V_{B4}$ was treated with corn oil (Vehicle B) at 10 ml/kg according to the treatment schedule 2Q1Dx1 (with 2 hours between the 2 injections).

The Group B4 was treated at 400 mg/kg with the Test Substance at 20 mg/ml (without sonication) according to the treatment schedule 2Q1Dx1 (with 2 hours between the 2 injections).

At D0, the mice were treated by PO administration.
Monitoring of Mice

Morbidity, mortality and evident signs of toxicity of mice were considered daily from D0 until the end of the experiment (D14 or D15).

Monitoring of mice for detailed behavioral and clinical observations was performed twice a week from D0 until the end of the experiment (D14 or D15) according to the standard operating procedures No. TEC-192.

Body weight of mice was monitored at D1, D2 and then twice a week until the end of the experiment (D14 or D15) according to the standard operating procedures No. TEC-108. Weight loss was assessed against the starting weight of each mouse at D0.

During the course of the experiment, animals were sacrificed if any of the following occurs:
- Signs of suffering (cachexia, weakening, difficulty to move or to eat),
- Compound toxicity (hunching, convulsions),
- 25% body weight loss on any day.

Sacrifice of Animals

Figure 3:
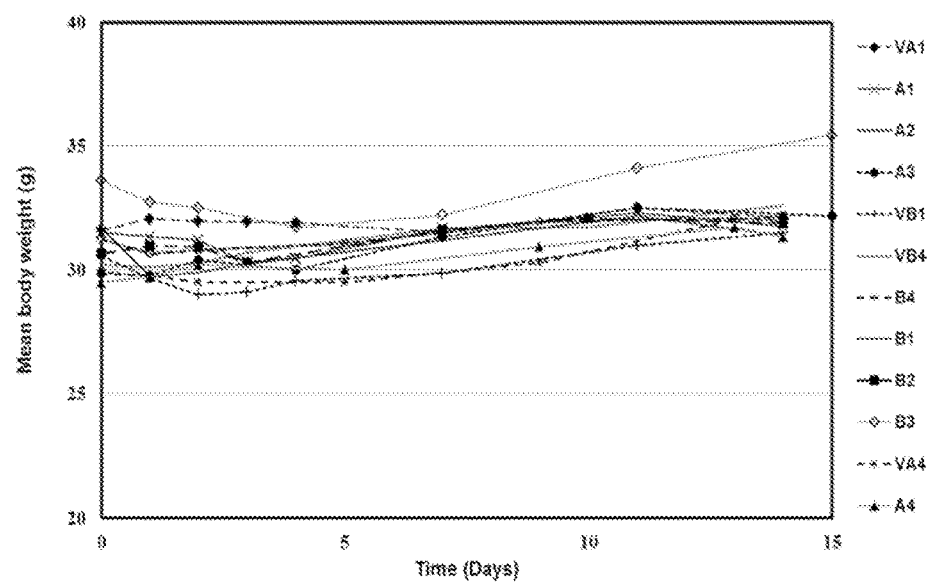
FIG. 3 is a graph showing the body weight of mice treated from D0 to D14 with Quin 18 or Quin 19 at different doses.

At D14 or D15, animals were be sacrificed by $CO_2$ inhalation and a macroscopic autopsy was performed.
Results
Study of Body Weight The results of mean body weight (MBW) curves are presented FIG. 3.

The mice of the Group $V_{A1}$ treated with vehicle A, polysorbate 80 0.4% (10 ml/kg, PO, Q1Dx1) did not exhibited any loss of body weight. The MBW from D0 to D14 was respectively of 31.6±1.23 g and 32.13±1.79 g. The Test Substance vehicle A, polysorbate 80 0.4% (10 ml/kg, PO, Q1Dx1) was well tolerated.

The mice of the Group A1 treated with Quin 18/polysorbate 80 0.4% (10 mg/ml, with sonication, 10 ml/kg, 100 mg/kg, PO, Q1Dx1) did not exhibited any loss of body

TABLE 5

| Group | Number of Animals | Treatment | Dose | Volume of adm. | Adm. Route | Treatment schedule | Sacrifice |
|---|---|---|---|---|---|---|---|
| $V_{A1}$ | 3 | Vehicle A (Polysorbate 80 0.4%) | NA | 10 ml/kg | PO | Q1Dx1 | D14 |
| A1 | 3 | Quin 18 | 100 mg/kg (with sonication) | 10 ml/kg | PO | Q1Dx1 | D14 |
| A2 | 3 | Quin 18 | 200 mg/kg (with sonication) | 10 ml/kg | PO | Q1Dx1 | D14 |
| A3 | 3 | Quin 18 | 100 mg/kg (without sonication) | 10 ml/kg | PO | Q1Dx1 | D15 |
| $V_{A4}$ | 3 | Vehicle A (Polysorbate 80 0.4%) | NA | 10 ml/kg | PO | 2Q1Dx1 | D14 |
| A4 | 3 | Quin 18 | 200 mg/kg (without sonication) | 10 ml/kg | PO | 2Q1Dx1 | D14 |
| $V_{B1}$ | 3 | Vehicle B (Corn oil) | NA | 10 ml/kg | PO | Q1Dx1 | D14 |
| B1 | 3 | Quin 19 | 100 mg/kg (with sonication) | 10 ml/kg | PO | Q1Dx1 | D14 |
| B2 | 3 | Quin 19 | 200 mg/kg (with sonication) | 10 ml/kg | PO | Q1Dx1 | D14 |
| B3 | 3 | Quin 19 | 200 mg/kg (without sonication) | 10 ml/kg | PO | Q1Dx1 | D15 |
| $V_{B4}$ | 3 | Vehicle B (Corn oil) | NA | 10 ml/kg | PO | 2Q1Dx1 | D14 |
| B4 | 3 | Quin 19 | 400 mg/kg (without sonication) | 10 ml/kg | PO | 2Q1Dx1 | D14 | weight. The MBW from D0 to D14 was respectively of 31.5±1.48 g and 31.77±0.76 g. The Test Substance Quin 18/polysorbate 80 0.4% (10 mg/ml, with sonication, 10 ml/kg, 100 mg/kg, PO, Q1Dx1) was well tolerated.

The mice of the Group A2 treated with Quin 18/polysorbate 80 0.4% (20 mg/ml, with sonication, 10 ml/kg, 200 mg/kg, PO, Q1Dx1) did not exhibited any loss of body weight. The MBW from D0 to D14 was respectively of 30.2±1.15 g and 32.6±1.35 g. The Test Substance Quin 18/polysorbate 80 0.4% (20 mg/ml, with sonication, 10 ml/kg, 200 mg/kg, PO, Q1Dx1) was well tolerated.

The mice of the Group A3 treated with Quin 18/polysorbate 80 0.4% (10 mg/ml, with sonication, 10 ml/kg, 100 mg/kg, PO, Q1Dx1) did not exhibited any loss of body weight. The MBW from D0 to D15 was respectively of 29.9±1.25 g and 32.17±1.94 g. The Test Substance Quin 18/polysorbate 80 0.4% (10 mg/ml, with sonication, 10 ml/kg, 100 mg/kg, PO, Q1Dx1) was well tolerated.

The mice of the Group $V_{A4}$ treated with vehicle A, polysorbate 80 0.4% (10 ml/kg, PO, 2Q1Dx1, 2 hours between the 2 injections) did not exhibited any loss of body weight. The MBW from D0 to D14 was respectively of 29.83±1.56 g and 32.17±2.91 g. The Test Substance vehicle A, polysorbate 80 0.4% (10 ml/kg, PO, 2Q1Dx1, 2 hours between the 2 injections) was well tolerated.

The mice of the Group A4 treated with Quin 18/polysorbate 80 0.4% (20 mg/ml, with sonication, 10 ml/kg, 200 mg/kg, PO, Q1Dx1) did not exhibited any loss of body weight. The MBW from D0 to D14 was respectively of 29.5±0.89 g and 31.33±1.63 g. The Test Substance Quin 18/polysorbate 80 0.4% (20 mg/ml, with sonication, 10 ml/kg, 200 mg/kg, PO, Q1Dx1) was well tolerated.

The mice of the Group $V_{B1}$ treated with vehicle B, corn oil (10 ml/kg, PO, Q1Dx1) did not exhibited any loss of body weight. The MBW from D0 to D14 was respectively of 30.57±1.32 g and 31.5±1.64 g. The Test Substance vehicle B, corn oil (10 ml/kg, PO, Q1Dx1) was well tolerated.

The mice of the Group B1 treated with Quin 19/corn oil (10 mg/ml, with sonication, 10 ml/kg, 100 mg/kg, PO, Q1Dx1) did not exhibited any loss of body weight. The MBW from D0 to D14 was respectively of 31.67±2.25 g and 31.4±0.44 g. The Test Substance Quin 19/corn oil (10 mg/ml, with sonication, 10 ml/kg, 100 mg/kg, PO, Q1Dx1) was well tolerated.

The mice of the Group B2 treated with Quin 19/corn oil (20 mg/ml, with sonication, 10 ml/kg, 200 mg/kg, PO, Q1Dx1) did not exhibited any loss of body weight. The MBW from D0 to D14 was respectively of 30.67±0.21 g and 31.9±1.15 g. The Test Substance Quin 190/corn oil (20 mg/ml, with sonication, 10 ml/kg, 200 mg/kg, PO, Q1Dx1) was well tolerated.

The mice of the Group B3 treated with Quin 19/corn oil (20 mg/ml, without sonication, 10 ml/kg, 200 mg/kg, PO, Q1Dx1) did not exhibited any loss of body weight. The MBW from D0 to D15 was respectively of 33.6±2.11 g and 35.43±1.99 g. The Test Substance Quin 19/corn oil (20 mg/ml, without sonication, 10 ml/kg, 200 mg/kg, PO, Q1Dx1) was well tolerated.

The mice of the Group $V_{B4}$ treated with vehicle B, corn oil (10 ml/kg, PO, 2Q1Dx1, 2 hours between the 2 injections) did not exhibited any loss of body weight. The MBW from D0 to D14 was respectively of 31.23±1.23 g and 32±0.7 g. The Test Substance vehicle B, corn oil (10 ml/kg, PO, 2Q1Dx1, 2 hours between the 2 injections) was well tolerated.

The mice of the Group B4 treated with Quin 19/corn oil (20 mg/ml, without sonication, 10 ml/kg, PO, 2Q1Dx1, 2 hours between the 2 injections, 400 mg/kg) did not exhibited any loss of body weight. The MBW from D0 to D14 was respectively of 31.03±1.86 g and 32.53±1 g. The Test Substance Quin 19/corn oil (20 mg/ml, without sonication, 10 ml/kg, PO, 2Q1Dx1, 2 hours between the 2 injections, 400 mg/kg) was well tolerated.

Monitoring of Mice

The monitoring of mice (observation of mobility, mortality and evident sign of toxicity) was performed twice a week and was summarized in Table 6. No particular sign was observed.

TABLE 6

| Group | Treatment schedule | D0 | D1 | D2 | D3 | D4 | D5 | D7 |
|---|---|---|---|---|---|---|---|---|
| VA1 | Q1Dx1 | 31.6 ± 1.23 | 32.07 ± 2.02 | 31.97 ± 1.95 | 31.93 ± 2.45 | 31.9 ± 2.72 | NA | 31.5 ± 1.55 |
| A1 | Q1Dx1 | 31.5 ± 1.48 | 31.33 ± 0.8 | 31.2 ± 0.7 | 30.3 ± 0.53 | 30.47 ± 0.78 | NA | 31.63 ± 0.49 |
| A2 | Q1Dx1 | 30.2 ± 1.15 | 31.13 ± 1.01 | 30.27 ± 0.74 | 30.7 ± 0.44 | NA | NA | 31.67 ± 0.49 |
| A3 | Q1Dx1 | 29.9 ± 1.25 | 29.8 ± 1.05 | 30.4 ± 1.25 | NA | 30 ± 1.01 | NA | 31.33 ± 0.74 |
| VA4 | 2Q1Dx1 | 29.83 ± 1.56 | 29.8 ± 1.61 | 29.5 ± 2.21 | NA | NA | 29.5 ± 1.71 | NA |
| A4 | 2Q1Dx1 | 29.5 ± 0.89 | 29.73 ± 1.22 | 30.2 ± 1.31 | NA | NA | 30 ± 1.45 | NA |
| VB1 | Q1Dx1 | 30.57 ± 1.32 | 29.67 ± 0.81 | 29 ± 0.62 | 29.1 ± 0.75 | 29.57 ± 1.26 | NA | 29.87 ± 0.35 |
| B1 | Q1Dx1 | 31.67 ± 2.25 | 29.73 ± 0.83 | 29.9 ± 0.2 | 30.23 ± 0.4 | 30.5 ± 0.98 | NA | 31.2 ± 0.1 |
| B2 | Q1Dx1 | 30.67 ± 0.21 | 30.97 ± 0.4 | 30.93 ± 0.25 | 30.3 ± 0.85 | NA | NA | 31.6 ± 1.97 |
| B3 | Q1Dx1 | 33.6 ± 2.11 | 32.73 ± 1.46 | 32.5 ± 0.62 | NA | 31.73 ± 0.9 | NA | 32.2 ± 0.5 |
| VB4 | 2Q1Dx1 | 31.23 ± 1.23 | 30.67 ± 1.24 | 30.8 ± 1.73 | NA | NA | 31.07 ± 0.47 | NA |
| B4 | 2Q1Dx1 | 31.03 ± 1.86 | 30.47 ± 2.2 | 30.47 ± 1.3 | NA | NA | 31.03 ± 1.55 | NA |

| Group | Treatment schedule | D9 | D10 | D11 | D13 | D14 | D15 |
|---|---|---|---|---|---|---|---|
| VA1 | Q1Dx1 | NA | NA | 32.47 ± 1.46 | NA | 32.13 ± 1.79 | NA |
| A1 | Q1Dx1 | NA | NA | 32.3 ± 1.37 | NA | 31.77 ± 0.76 | NA |
| A2 | Q1Dx1 | NA | 31.73 ± 0.95 | NA | NA | 32.6 ± 1.35 | NA |
| A3 | Q1Dx1 | NA | NA | 32.3 ± 2.02 | NA | NA | 32.17 ± 1.94 |
| VA4 | 2Q1Dx1 | 30.3 ± 0.95 | NA | NA | 32.03 ± 2.58 | 32.17 ± 2.91 | NA |
| A4 | 2Q1Dx1 | 30.93 ± 3.04 | NA | NA | 31.73 ± 2.64 | 31.33 ± 1.63 | NA |
| VB1 | Q1Dx1 | NA | NA | 31 ± 0.66 | NA | 31.5 ± 1.64 | NA |
| B1 | Q1Dx1 | NA | NA | 32.17 ± 1.36 | NA | 31.4 ± 0.44 | NA |
| B2 | Q1Dx1 | NA | 32.1 ± 3.2 | NA | NA | 31.9 ± 1.15 | NA |

TABLE 6-continued

| | | | | | | | |
|---|---|---|---|---|---|---|---|
| B3 | Q1Dx1 | NA | NA | 34.1 ± 1.51 | NA | NA | 35.43 ± 1.99 |
| VB4 | 2Q1Dx1 | 31.93 ± 2.06 | NA | NA | 32.1 ± 0.26 | 32 ± 0.7 | NA |
| B4 | 2Q1Dx1 | 31.77 ± 2.32 | NA | NA | 31.7 ± 1.18 | 32.53 ± 1 | NA |

Autopsy

Table 7 summarized the cause of the death of each mouse, and macroscopic observations. No particular sign was observed in the mice treated with Quin 18 or Quin 19 and/or vehicles.

TABLE 7

Female mice

| Group | Number of mice | Day | Action | Reason | Observations |
|---|---|---|---|---|---|
| VA1 | 3 | 14 | Sacrifice | End of study | NTR |
| A1 | 3 | 14 | Sacrifice | End of study | NTR |
| A2 | 3 | 14 | Sacrifice | End of study | NTR |
| A3 | 3 | 15 | Sacrifice | End of study | NTR |
| VA4 | 3 | 14 | Sacrifice | End of study | NTR* |
| A4 | 3 | 15 | Sacrifice | End of study | NTR |
| VB1 | 3 | 14 | Sacrifice | End of study | NTR* |
| B1 | 3 | 14 | Sacrifice | End of study | NTR* |
| B2 | 3 | 14 | Sacrifice | End of study | NTR |
| B3 | 3 | 15 | Sacrifice | End of study | NTR |
| VB4 | 3 | 14 | Sacrifice | End of study | NTR |
| B4 | 3 | 14 | Sacrifice | End of study | NTR |

*For the group VA4, 2 mice had air bubble in the colon and for the groups VB1 and B1, one mouse of each group had air bubble in the caecum.

CONCLUSION

The Test Substance Quin18/polysorbate 80 0.4% was well tolerated up to 200 mg/kg (maximal solubility; no observation was noted for the body weight clinical signs and macroscopic analysis in female mice).

The Test Substance Quin19/corn oil was well tolerated up to 400 mg/kg (maximal solubility; no observation was noted for the body weight clinical signs and macroscopic analysis in female mice).

Thus, these results show that Quin18 and Quin19 are extremely well tolerated in mice, with no signs of toxicity at the dose levels tested.

The invention claimed is:

1. A compound of general Formula I:

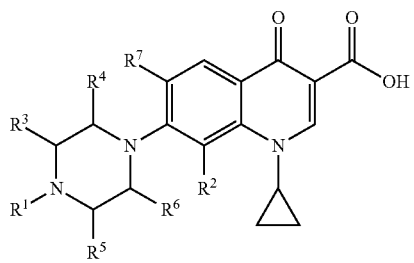

and pharmaceutically acceptable salts thereof, wherein:
$R^1$ represents a saturated or unsaturated, substituted or unsubstituted, branched or unbranched alkyl group comprising 4 to 20 carbons atoms, when the alkyl group is substituted, the substituent is selected in the group comprising halo, hydroxyl, nitro, amido, carboxy, amino, cyano, alkoxy, haloalkoxy, or haloalkyl, $R^2$ represents a substituent selected from the group comprising hydrogen, alkyl, alkene, alkyne, cycloalkyl, aryl, halo, hydroxyl, oxo, nitro, amido, carboxy, amino, cyano, alkoxy, haloalkoxy, or haloalkyl, $R^3$, $R^4$, $R^5$ and $R^6$ may be identical or different and each represents a substituent selected from hydrogen, alkyl, alkene, alkyne, cycloalkyl, aryl, halo, hydroxyl, oxo, nitro, amido, carboxy, amino, cyano, alkoxy, haloalkoxy, or haloalkyl, $R^7$ represents a substituent selected from hydrogen, alkyl, alkene, alkyne, cycloalkyl, aryl, halo, hydroxyl, oxo, nitro, amido, carboxy, amino, cyano, alkoxy, haloalkoxy, or haloalkyl, with the condition that the compounds of formula I are not:
7-(4-butylpiperazin-l-yl)-1-cyclopropyl-6-fluoro-4-oxo-1,4-dihydroquinoline-3-carboxylic acid,
1-cyclopropyl-6-fluoro-7-(4-heptylpiperazin-l-yl)-4-oxo-1,4-dihydroquinoline-3-carboxylic acid,
7-(4-butyl-3-methylpiperazin-1-yl)-1-cyclopropyl-6-fluoro-4-oxo-1,4-dihydroquinoline-3-carboxylic acid,
1-cyclopropyl-6-fluoro-7-(4-hexyl-3-methylpiperazin-1-yl)-4-oxo-1,4-dihydroquinoline-3-carboxylic acid,
1-cyclopropyl-6-fluoro-7-(4-(4-hydroxybuty)piperazin-1-yl)-4-oxo-1,4-dihydroquinoline-3-carboxylic acid,
with the condition that when $R^2$ is a hydrogen and $R^7$ is a fluorine, $R^3$, $R^4$, $R^5$ and $R^6$ are not a methyl group.

2. The compound according to claim 1, wherein $R^1$ represents a saturated or unsaturated, substituted or unsubstituted, branched or unbranched alkyl group comprising 5 to 16 carbons atoms.

3. The compound according to claim 1, wherein $R^2$ represents a substituent selected from the group comprising hydrogen, methyl, methoxy, ethoxy, chloro and fluoro.

4. The compound according to claim 1, wherein $R^3$, $R^4$, $R^5$ and $R^6$ are identical and represent each a hydrogen.

5. The compound according to claim 1, wherein $R^7$ represents a hydrogen, $NH_2$ or fluoro.

6. The compound according to claim 1, having the general formula II corresponding to the general formula I wherein $R^7$ is a fluorine:

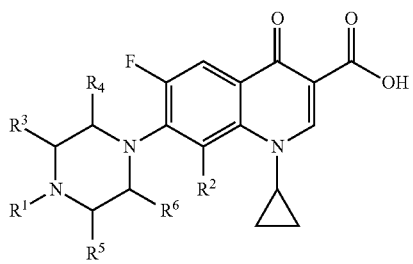

and pharmaceutically acceptable salts thereof.

7. The compound according to claim 1, having the general formula III corresponding to compounds of general formula II wherein $R^3$, $R^4$, $R^5$ and $R^6$ are identical and represent a hydrogen atom:

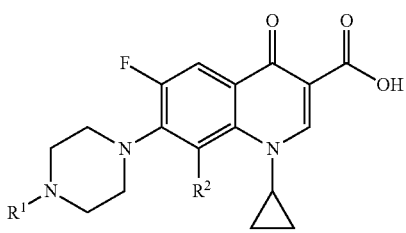

and pharmaceutically acceptable salts thereof.

8. The compound according to claim 1, selected from the group comprising:
- 1-cyclopropyl-6-fluoro-4-oxo-7-(4-pentylpiperazin-1-yl)-1,4-dihydroquinoline-3-carboxylic acid,
- 1-cyclopropyl-6-fluoro-7-(4-hexylpiperazin-1-yl)-4-oxo-1,4-dihydroquinoline-3-carboxylic acid,
- 1-cyclopropyl-6-fluoro-7-(4-octylpiperazin-1-yl)-4-oxo-1,4-dihydroquinoline-3-carboxylic acid,
- 1-cyclopropyl-6-fluoro-7-(4-nonylpiperazin-1-yl)-4-oxo-1,4-dihydroquinoline-3-carboxylic acid,
- 1-cyclopropyl-7-(4-decylpiperazin-1-yl)-6-fluoro-4-oxo-1,4-dihydroquinoline-3-carboxylic acid,
- 1-cyclopropyl-6-fluoro-4-oxo-7-(4-undecylpiperazin-1-yl)-1,4-dihydroquinoline-3-carboxylic acid,
- 1-cyclopropyl-7-(4-dodecylpiperazin-1-yl)-6-fluoro-4-oxo-1,4-dihydroquinoline-3-carboxylic acid,
- 1-cyclopropyl-6-fluoro-4-oxo-7-(4-tridecylpiperazin-1-yl)-1,4-dihydroquinoline-3-carboxylic acid,
- 1-cyclopropyl-6-fluoro-4-oxo-7-(4-tetradecylpiperazin-1-yl)-1,4-dihydroquinoline-3-carboxylic acid,
- 1-cyclopropyl-6-fluoro-4-oxo-7-(4-pentadecylpiperazin-1-yl)-1,4-dihydroquinoline-3-carboxylic acid,
- 1-cyclopropyl-6-fluoro-7-(4-hexadecylpiperazin-1-yl)-4-oxo-1,4-dihydroquinoline-3-carboxylic acid,
- 1-cyclopropyl-6-fluoro-8-methoxy-4-oxo-7-(4-pentylpiperazin-1-yl)-1,4-dihydroquinoline-3-carboxylic acid,
- 1-cyclopropyl-6-fluoro-7-(4-hexylpiperazin-1-yl)-8-methoxy-4-oxo-1,4-dihydroquinoline-3-carboxylic acid,
- 1-cyclopropyl-6-fluoro-7-(4-heptylpiperazin-1-yl)-8-methoxy-4-oxo-1,4-dihydroquinoline-3-carboxylic acid,
- 1-cyclopropyl-6-fluoro-8-methoxy-7-(4-octylpiperazin-1-yl)-4-oxo-1,4-dihydroquinoline-3-carboxylic acid,
- 1-cyclopropyl-6-fluoro-8-methoxy-7-(4-nonylpiperazin-1-yl)-4-oxo-1,4-dihydroquinoline-3-carboxylic acid,
- 1-cyclopropyl-7-(4-decylpiperazin-1-yl)-6-fluoro-8-methoxy-4-oxo-1,4-dihydroquinoline-3-carboxylic acid,
- 1-cyclopropyl-6-fluoro-8-methoxy-4-oxo-7-(4-undecylpiperazin-1- yl)-1,4-dihydroquinoline-3-carboxylic acid,
- 1-cyclopropyl-7-(4-dodecylpiperazin-1-yl)-6-fluoro-8-methoxy-4-oxo-1,4-dihydroquinoline-3-carboxylic acid,
- 1-cyclopropyl-6-fluoro-8-methoxy-4-oxo-7-(4-tridecylpiperazin-1-yl)-1,4-dihydroquinoline-3-carboxylic acid,
- 1-cyclopropyl-6-fluoro-8-methoxy-4-oxo-7-(4-tetradecylpiperazin-1-yl)-1,4-dihydroquinoline-3-carboxylic acid,
- 1-cyclopropyl-6-fluoro-8-methoxy-4-oxo-7-(4-pentadecylpiperazin-1-yl)-1,4-dihydroquinoline-3-carboxylic acid,
- 1-cyclopropyl-6-fluoro-7-(4-hexadecylpiperazin-1-yl)-8-methoxy-4-oxo-1,4-dihydroquinoline-3-carboxylic acid, and pharmaceutically acceptable salts thereof.

9. A pharmaceutical composition comprising at least one compound according to claim 1, or a pharmaceutically acceptable salt, and at least one pharmaceutically acceptable carrier, diluent, excipient and /or adjuvant.

10. The pharmaceutical composition according to claim 9, further comprising a therapeutic agent and/or active ingredient.

11. A medicament comprising a compound according to claim 1.

12. The medicament according to claim 11, further comprising a therapeutic agent and/or active ingredient.

* * * * *